(12) United States Patent
Handique

(10) Patent No.: US 11,453,906 B2
(45) Date of Patent: Sep. 27, 2022

(54) MULTIPLEXED DIAGNOSTIC DETECTION APPARATUS AND METHODS

(71) Applicant: HANDYLAB, INC., Franklin Lakes, NJ (US)

(72) Inventor: Kalyan Handique, Ypsilanti, MI (US)

(73) Assignee: HANDYLAB, INC., Franklin Lakes, NJ (US)

( * ) Notice: Subject to any disclaimer, the term of this patent is extended or adjusted under 35 U.S.C. 154(b) by 134 days.

(21) Appl. No.: 14/267,232

(22) Filed: May 1, 2014

(65) Prior Publication Data

US 2014/0329301 A1 Nov. 6, 2014

Related U.S. Application Data

(63) Continuation of application No. PCT/US2012/063091, filed on Nov. 1, 2012.
(Continued)

(51) Int. Cl.
*C12M 1/00* (2006.01)
*C12Q 1/6806* (2018.01)
(Continued)

(52) U.S. Cl.
CPC .......... *C12Q 1/6806* (2013.01); *B01L 3/5027* (2013.01); *B01L 3/502723* (2013.01);
(Continued)

(58) Field of Classification Search
CPC ................ C12Q 1/6806; B01L 3/5027; B01L 3/502723; B01L 3/502738; B01L 7/52;
(Continued)

(56) References Cited

U.S. PATENT DOCUMENTS 1,434,314 A 10/1922 Raich
1,616,419 A 2/1927 Wilson
(Continued)

FOREIGN PATENT DOCUMENTS

AU 1357102 3/2002
AU 3557502 7/2002
(Continued)

OTHER PUBLICATIONS

Kuo et al., "Remnant cationic dendrimers block RNA migration in electrophoresis after monophasic lysis", J Biotech. (2007) 129: 383-390.
(Continued)

*Primary Examiner* — Liban M Hassan
(74) *Attorney, Agent, or Firm* — Knobbe, Martens, Olson & Bear, LLP

(57) ABSTRACT

Disclosed herein are devices configured for the amplification and detection of multiple targets from a sample, and methods of using the same. The devices disclosed herein comprise microfluidic cartridges have a first stage (amplification) and a second (detection) stage. The two-stage design of the cartridges enables testing for multiple targets within a sample, i.e., from a single nucleic acid amplification reaction. Methods for the amplification and detection of a plurality of target nucleic acids from a sample are also disclosed herein.

23 Claims, 22 Drawing Sheets

Related U.S. Application Data

(60) Provisional application No. 61/556,032, filed on Nov. 4, 2011.

(51) Int. Cl.
 B01L 3/00 (2006.01)
 B01L 7/00 (2006.01)
 F16K 99/00 (2006.01)

(52) U.S. Cl.
 CPC ............ *B01L 3/502738* (2013.01); *B01L 7/52* (2013.01); *B01L 2200/027* (2013.01); *B01L 2200/0684* (2013.01); *B01L 2200/10* (2013.01); *B01L 2300/0816* (2013.01); *B01L 2400/06* (2013.01); *B01L 2400/0677* (2013.01); *F16K 99/0036* (2013.01); *F16K 2099/0084* (2013.01)

(58) Field of Classification Search
 CPC ....... B01L 2200/027; B01L 2200/0684; B01L 2200/10; B01L 2300/0816; B01L 2400/06; B01L 2400/0677; F16K 99/0036; F16K 2099/0084
 USPC .......................................... 435/287.2, 287.1
 See application file for complete search history.

(56) References Cited

U.S. PATENT DOCUMENTS

| | | |
|---|---|---|
| 1,733,401 A | 8/1930 | Lovekin |
| D189,404 S | 12/1960 | Nicolle |
| 3,050,239 A | 8/1962 | Williams |
| 3,528,449 A | 9/1970 | Witte et al. |
| 3,813,316 A | 5/1974 | Chakrabarty et al. |
| 3,905,772 A | 9/1975 | Hartnett et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,472,357 A | 9/1984 | Levy et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| 4,698,302 A | 10/1987 | Whitehead et al. |
| D292,735 S | 11/1987 | Lovborg |
| 4,720,374 A | 1/1988 | Ramachandran |
| 4,724,207 A | 2/1988 | Hou et al. |
| 4,795,698 A | 1/1989 | Owen et al. |
| 4,798,693 A | 1/1989 | Mase et al. |
| 4,800,022 A | 1/1989 | Leonard |
| 4,827,944 A | 5/1989 | Nugent |
| 4,841,786 A | 6/1989 | Schulz |
| D302,294 S | 7/1989 | Hillman |
| 4,855,110 A | 8/1989 | Marker et al. |
| 4,871,779 A | 10/1989 | Killat et al. |
| 4,889,818 A | 12/1989 | Gelfand et al. |
| 4,895,650 A | 1/1990 | Wang |
| 4,902,624 A | 2/1990 | Columbus et al. |
| 4,914,710 A | 4/1990 | Ward et al. |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,948,561 A | 8/1990 | Hinckley et al. |
| 4,949,742 A | 8/1990 | Rando et al. |
| D310,413 S | 9/1990 | Bigler |
| 4,963,498 A | 10/1990 | Hillman |
| 4,965,188 A | 10/1990 | Mullis et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 4,994,373 A | 2/1991 | Stavrianopoulos et al. |
| 4,997,772 A | 3/1991 | Sutton et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,089,233 A | 2/1992 | DeVaney, Jr. et al. |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,147,777 A | 9/1992 | Sutton et al. |
| 5,155,166 A | 10/1992 | Danielson et al. |
| 5,169,512 A | 12/1992 | Wiedenmann et al. |
| 5,173,269 A | 12/1992 | Mon et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| 5,229,297 A | 7/1993 | Schnipelsky et al. |
| 5,231,015 A | 7/1993 | Cummins et al. |
| D338,275 S | 8/1993 | Fischer et al. |
| 5,234,809 A | 8/1993 | Boom et al. |
| 5,250,263 A | 10/1993 | Manz |
| 5,252,743 A | 10/1993 | Barrett et al. |
| 5,256,376 A | 10/1993 | Callan et al. |
| 5,273,716 A | 12/1993 | Northrup et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,334,499 A | 8/1994 | Burdick et al. |
| 5,338,671 A | 8/1994 | Scalice et al. |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |

(56) References Cited

U.S. PATENT DOCUMENTS

| | | |
|---|---|---|
| 5,372,946 A | 12/1994 | Cusak et al. |
| 5,374,395 A | 12/1994 | Robinson |
| 5,384,499 A | 1/1995 | Pedersen et al. |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,466,574 A | 11/1995 | Liberti et al. |
| 5,474,796 A | 12/1995 | Brennan |
| 5,475,487 A | 12/1995 | Mariella, Jr. et al. |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,576,218 A | 11/1996 | Zurek et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,582,988 A | 12/1996 | Backus et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold et al. |
| 5,601,727 A | 2/1997 | Bormann et al. |
| 5,603,351 A | 2/1997 | Cherukuri et al. |
| 5,605,662 A | 2/1997 | Heller et al. |
| 5,609,910 A | 3/1997 | Hackleman |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,639,428 A | 6/1997 | Cottingham |
| 5,643,738 A | 7/1997 | Zanzucchi et al. |
| 5,645,801 A | 7/1997 | Bouma et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,654,141 A | 8/1997 | Mariani et al. |
| 5,658,515 A | 8/1997 | Lee et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,683,659 A | 11/1997 | Hovatter |
| 5,699,157 A | 12/1997 | Parce et al. |
| 5,700,637 A | 12/1997 | Southern |
| 5,705,813 A | 1/1998 | Apffel et al. |
| 5,720,923 A | 2/1998 | Haff et al. |
| 5,721,136 A | 2/1998 | Finney et al. |
| 5,725,831 A | 3/1998 | Reichler et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,746,978 A | 5/1998 | Bienhaus et al. |
| 5,747,666 A | 5/1998 | Willis |
| 5,750,015 A | 5/1998 | Soane et al. |
| 5,755,942 A | 5/1998 | Zanzucchi et al. |
| 5,762,874 A | 6/1998 | Seaton et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,783,148 A | 7/1998 | Cottingham et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,819,749 A | 10/1998 | Lee et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,911,737 A | 6/1999 | Lee et al. |
| 5,912,124 A | 6/1999 | Kumar |
| 5,912,134 A | 6/1999 | Shartle |
| 5,914,229 A | 6/1999 | Loewy |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,161 A | 7/1999 | Krulevitch et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |

(56) References Cited

U.S. PATENT DOCUMENTS

| | | |
|---|---|---|
| 5,935,401 A | 8/1999 | Amigo |
| 5,939,291 A | 8/1999 | Loewy et al. |
| 5,939,312 A | 8/1999 | Baier et al. |
| 5,942,443 A | 8/1999 | Parce et al. |
| 5,944,717 A | 8/1999 | Lee et al. |
| D413,677 S | 9/1999 | Dumitrescu et al. |
| D414,271 S | 9/1999 | Mendoza |
| 5,948,227 A | 9/1999 | Dubrow |
| 5,948,363 A | 9/1999 | Gaillard |
| 5,948,673 A | 9/1999 | Cottingham |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,349 A | 9/1999 | Petersen et al. |
| 5,958,694 A | 9/1999 | Nikiforov |
| 5,959,221 A | 9/1999 | Boyd et al. |
| 5,959,291 A | 9/1999 | Jensen |
| 5,935,522 A | 10/1999 | Swerdlow et al. |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,985,651 A | 11/1999 | Hunicke-Smith |
| 5,989,402 A | 11/1999 | Chow et al. |
| 5,992,820 A | 11/1999 | Fare et al. |
| 5,993,611 A | 11/1999 | Moroney et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,450 A | 12/1999 | Northrup et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,033,880 A | 3/2000 | Haff et al. |
| 6,043,080 A | 3/2000 | Lipshutz et al. |
| 6,043,880 A | 3/2000 | Andrews et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,751 A | 5/2000 | Neukermans |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,143,547 A | 11/2000 | Hsu |
| 6,149,787 A | 11/2000 | Chow et al. |
| 6,149,872 A | 11/2000 | Mack et al. |
| 6,156,199 A | 12/2000 | Zuk |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| 6,194,563 B1 | 2/2001 | Cruickshank |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,203,759 B1 | 3/2001 | Pelc et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Kikiforov |
| 6,291,248 B1 | 9/2001 | Haj-Ahmad |
| 6,294,063 B1 | 9/2001 | Becker et al. |
| 6,300,124 B1 | 10/2001 | Blumenfeld et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,310,199 B1 | 10/2001 | Smith et al. |
| 6,316,774 B1 | 11/2001 | Giebeler et al. |
| 6,319,469 B1 | 11/2001 | Mian et al. |
| 6,319,474 B1 | 11/2001 | Krulevitch et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |

(56) References Cited

U.S. PATENT DOCUMENTS

| | | |
|---|---|---|
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,047 B2 | 9/2002 | Dattagupta et al. |
| 6,448,064 B1 | 9/2002 | Vo-Dinh et al. |
| 6,453,928 B1 | 9/2002 | Kaplan et al. |
| 6,458,259 B1 | 10/2002 | Parce et al. |
| 6,465,257 B1 | 10/2002 | Parce et al. |
| 6,468,761 B2 | 10/2002 | Yang et al. |
| 6,472,141 B2 | 10/2002 | Nikiforov |
| D466,219 S | 11/2002 | Wynschenk et al. |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,186 B1 | 1/2003 | Zou et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,181 B1 | 2/2003 | Northrup et al. |
| 6,521,188 B1 | 2/2003 | Webster |
| 6,524,456 B1 | 2/2003 | Ramsey et al. |
| 6,524,532 B1 | 2/2003 | Northrup |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,432 B1 | 3/2003 | Schneider et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,565,815 B1 | 5/2003 | Chang et al. |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,605,475 B1 | 8/2003 | Taylor et al. |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,133 B2 | 12/2003 | Knapp et al. |
| 6,670,153 B2 | 12/2003 | Stern |
| D484,989 S | 1/2004 | Gebrian |
| 6,672,458 B2 | 1/2004 | Hansen et al. |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,699,713 B2 | 3/2004 | Benett et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,762,049 B2 | 7/2004 | Zou et al. |
| 6,764,859 B1 | 7/2004 | Kreuwel et al. |
| 6,766,817 B2 | 7/2004 | Dias da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| D500,363 S | 12/2004 | Fanning et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |

(56) References Cited

U.S. PATENT DOCUMENTS

| | | |
|---|---|---|
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,940,598 B2 | 9/2005 | Christel et al. |
| 6,942,771 B1 | 9/2005 | Kayyem |
| 6,951,632 B2 | 10/2005 | Unger et al. |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,979,424 B2 | 12/2005 | Northrup et al. |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,041,258 B2 | 5/2006 | Desmond et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | Dias da Silva |
| 7,069,952 B1 | 7/2006 | McReynolds et al. |
| 7,072,036 B2 | 7/2006 | Jones et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,892 B2 | 10/2006 | Ammann et al. |
| 7,118,910 B2 | 10/2006 | Unger et al. |
| 7,122,799 B2 | 10/2006 | Hsieh et al. |
| 7,135,144 B2 | 11/2006 | Christel et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,601 B1 | 1/2007 | Northrup et al. |
| 7,169,618 B2 | 1/2007 | Skold |
| D537,951 S | 3/2007 | Okamoto et al. |
| D538,436 S | 3/2007 | Patadia et al. |
| 7,188,001 B2 | 3/2007 | Young et al. |
| 7,192,557 B2 | 3/2007 | Wu et al. |
| 7,195,986 B1 | 3/2007 | Bousse et al. |
| 7,205,154 B2 | 4/2007 | Corson |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,255,833 B2 | 8/2007 | Chang et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| 7,297,313 B1 | 11/2007 | Northrup et al. |
| D556,914 S | 12/2007 | Okamoto et al. |
| 7,303,727 B1 | 12/2007 | Dubrow et al. |
| D559,995 S | 1/2008 | Handique et al. |
| 7,315,376 B2 | 1/2008 | Bickmore et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,480,042 B1 | 1/2009 | Phillips et al. |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |
| D598,566 S | 8/2009 | Allaer |
| 7,578,976 B1 | 8/2009 | Northrup et al. |
| D599,234 S | 9/2009 | Ito |
| 7,595,197 B2 | 9/2009 | Brasseur |
| 7,604,938 B2 | 10/2009 | Takahashi et al. |
| 7,622,296 B2 | 11/2009 | Joseph et al. |
| 7,628,902 B2 | 12/2009 | Knowlton et al. |
| 7,633,606 B2 | 12/2009 | Northrup et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,689,022 B2 | 3/2010 | Weiner et al. |
| 7,704,735 B2 | 4/2010 | Facer et al. |
| 7,705,739 B2 | 4/2010 | Northrup et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,785,868 B2 | 8/2010 | Yuan et al. |
| D628,305 S | 11/2010 | Gorrec et al. |
| 7,829,025 B2 | 11/2010 | Ganesan et al. |
| 7,858,366 B2 | 12/2010 | Northrup et al. |
| 7,867,776 B2 | 1/2011 | Kennedy et al. |
| D632,799 S | 2/2011 | Canner et al. |
| 7,892,819 B2 | 2/2011 | Wilding et al. |
| D637,737 S | 5/2011 | Wilson et al. |
| 7,955,864 B2 | 6/2011 | Cox et al. |
| 7,987,022 B2 | 7/2011 | Handique et al. |
| 7,998,708 B2 | 8/2011 | Handique et al. |
| 8,053,214 B2 | 11/2011 | Northrup |
| 8,071,056 B2 | 12/2011 | Burns et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,246,919 B2 | 8/2012 | Herchenbach et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |

(56) References Cited

U.S. PATENT DOCUMENTS

| | | |
|---|---|---|
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D686,749 S | 7/2013 | Trump |
| D687,567 S | 8/2013 | Jungheim et al. |
| D692,162 S | 10/2013 | Lentz et al. |
| 8,592,157 B2 | 11/2013 | Petersen et al. |
| 8,679,831 B2 | 3/2014 | Handique et al. |
| D702,854 S | 4/2014 | Nakahana et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| D710,024 S | 7/2014 | Guo |
| 8,765,076 B2 | 7/2014 | Handique et al. |
| 8,765,454 B2 | 7/2014 | Zhou et al. |
| 8,768,517 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| D729,404 S | 5/2015 | Teich et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |
| D742,027 S | 10/2015 | Lentz et al. |
| 9,186,677 B2 | 11/2015 | Williams et al. |
| 9,217,143 B2 | 12/2015 | Brahmasandra et al. |
| 9,222,954 B2 | 12/2015 | Lentz et al. |
| 9,234,236 B2 | 1/2016 | Thomas et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 9,480,983 B2 | 11/2016 | Lentz et al. |
| 9,528,142 B2 | 12/2016 | Handique |
| 9,618,139 B2 | 4/2017 | Handique |
| D787,087 S | 6/2017 | Duffy et al. |
| 9,670,528 B2 | 6/2017 | Handique et al. |
| 9,677,121 B2 | 6/2017 | Ganesan et al. |
| 9,701,957 B2 | 7/2017 | Wilson et al. |
| 9,745,623 B2 | 8/2017 | Steel |
| 9,765,389 B2 | 9/2017 | Gubatayao et al. |
| 9,789,481 B2 | 10/2017 | Petersen et al. |
| 9,802,199 B2 | 10/2017 | Handique et al. |
| 9,815,057 B2 | 11/2017 | Handique |
| 9,958,466 B2 | 5/2018 | Dalbert et al. |
| 10,065,185 B2 | 9/2018 | Handique |
| 10,071,376 B2 | 9/2018 | Williams et al. |
| 10,076,754 B2 | 9/2018 | Lentz et al. |
| 10,100,302 B2 | 10/2018 | Brahmasandra et al. |
| 10,139,012 B2 | 11/2018 | Handique |
| 10,179,910 B2 | 1/2019 | Duffy et al. |
| 10,234,474 B2 | 3/2019 | Williams et al. |
| 10,351,901 B2 | 7/2019 | Ganesan et al. |
| 10,364,456 B2 | 7/2019 | Wu et al. |
| 10,443,088 B1 | 10/2019 | Wu et al. |
| 10,494,663 B1 | 12/2019 | Wu et al. |
| 10,571,935 B2 | 2/2020 | Handique et al. |
| 10,590,410 B2 | 3/2020 | Brahmasandra et al. |
| 10,604,788 B2 | 3/2020 | Wu et al. |
| 10,619,191 B2 | 4/2020 | Ganesan et al. |
| 10,625,261 B2 | 4/2020 | Williams et al. |
| 10,625,262 B2 | 4/2020 | Williams et al. |
| 10,632,466 B1 | 4/2020 | Williams et al. |
| 10,695,764 B2 | 6/2020 | Handique et al. |
| 10,710,069 B2 | 7/2020 | Handique et al. |
| 10,717,085 B2 | 7/2020 | Williams et al. |
| 10,731,201 B2 | 8/2020 | Handique et al. |
| 10,781,482 B2 | 9/2020 | Gubatayao et al. |
| 10,799,862 B2 | 10/2020 | Handique et al. |
| 10,821,436 B2 | 11/2020 | Handique et al. |
| 10,821,446 B1 | 11/2020 | Handique et al. |
| 10,822,644 B2 | 11/2020 | Steel et al. |
| 10,843,188 B2 | 11/2020 | Handique et al. |
| 10,844,368 B2 | 11/2020 | Duffy et al. |
| 10,857,535 B2 | 12/2020 | Handique et al. |
| 10,865,437 B2 | 12/2020 | Handique et al. |
| 10,875,022 B2 | 12/2020 | Williams et al. |
| 10,900,066 B2 | 1/2021 | Handique et al. |
| 10,913,061 B2 | 2/2021 | Handique et al. |
| 11,060,082 B2 | 7/2021 | Brahmasandra et al. |
| 11,078,523 B2 | 8/2021 | Handique et al. |
| 11,085,069 B2 | 8/2021 | Handique et al. |
| 11,141,734 B2 | 10/2021 | Handique et al. |
| 11,142,785 B2 | 10/2021 | Handique et al. |
| 11,254,927 B2 | 2/2022 | Brahmasandra et al. |
| 11,266,987 B2 | 3/2022 | Handique |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0018513 A1 | 8/2001 | Baker |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0045358 A1 | 11/2001 | Kopf-Sill et al. |
| 2001/0046702 A1 | 11/2001 | Schembri |
| 2001/0048899 A1 | 12/2001 | Marouiss et al. |
| 2001/0051340 A1 | 12/2001 | Singh et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0022261 A1 | 2/2002 | Anderson et al. |
| 2002/0037499 A1 | 3/2002 | Quake et al. |
| 2002/0039783 A1 | 4/2002 | McMillan et al. |
| 2002/0047003 A1 | 4/2002 | Bedingham et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0086443 A1 | 7/2002 | Bamdad |
| 2002/0090320 A1 | 7/2002 | Burow et al. |
| 2002/0092767 A1 | 7/2002 | Bjornson et al. |
| 2002/0094303 A1 | 7/2002 | Yamamoto et al. |
| 2002/0131903 A1 | 9/2002 | Ingenhoven et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155010 A1 | 10/2002 | Karp et al. |
| 2002/0155477 A1 | 10/2002 | Ito |
| 2002/0169518 A1 | 11/2002 | Luoma et al. |
| 2002/0173032 A1 | 11/2002 | Zou et al. |
| 2002/0176804 A1 | 11/2002 | Strand et al. |
| 2002/0187557 A1 | 12/2002 | Hobbs et al. |
| 2002/0192808 A1 | 12/2002 | Gambini et al. |
| 2003/0008308 A1 | 1/2003 | Enzelberger et al. |
| 2003/0008320 A1 | 1/2003 | Baker |
| 2003/0019522 A1 | 1/2003 | Parunak |
| 2003/0022392 A1 | 1/2003 | Hudak |
| 2003/0036067 A1 | 2/2003 | Schwartz |
| 2003/0049174 A1 | 3/2003 | Ganesan |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0070677 A1 | 4/2003 | Handique et al. |
| 2003/0072683 A1 | 4/2003 | Stewart et al. |
| 2003/0073106 A1 | 4/2003 | Johansen et al. |
| 2003/0073110 A1 | 4/2003 | Aritomi et al. |
| 2003/0083686 A1 | 5/2003 | Freeman et al. |
| 2003/0087300 A1 | 5/2003 | Knapp et al. |
| 2003/0088657 A1 | 5/2003 | Eggers |
| 2003/0096310 A1 | 5/2003 | Hansen et al. |
| 2003/0099954 A1 | 5/2003 | Miltenyi et al. |

(56) References Cited

U.S. PATENT DOCUMENTS

| | | |
|---|---|---|
| 2003/0124611 A1 | 7/2003 | Schwartz |
| 2003/0127327 A1 | 7/2003 | Kurnik |
| 2003/0134333 A1 | 7/2003 | Dehlinger et al. |
| 2003/0136679 A1 | 7/2003 | Bohn et al. |
| 2003/0156991 A1 | 8/2003 | Halas et al. |
| 2003/0180192 A1 | 9/2003 | Seippel |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0043479 A1 | 3/2004 | Briscoe et al. |
| 2004/0053290 A1 | 3/2004 | Terbrueggen et al. |
| 2004/0063217 A1 | 4/2004 | Webster et al. |
| 2004/0065655 A1 | 4/2004 | Brown |
| 2004/0072278 A1 | 4/2004 | Chou et al. |
| 2004/0072375 A1 | 4/2004 | Gjerde et al. |
| 2004/0076996 A1 | 4/2004 | Kondo et al. |
| 2004/0086427 A1 | 5/2004 | Childers et al. |
| 2004/0086956 A1 | 5/2004 | Bachur |
| 2004/0132059 A1 | 7/2004 | Scurati et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0171515 A1 | 9/2004 | Hamers et al. |
| 2004/0189311 A1 | 9/2004 | Glezer et al. |
| 2004/0197810 A1 | 10/2004 | Takenaka et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0019902 A1 | 1/2005 | Mathies et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0112754 A1 | 5/2005 | Yoon et al. |
| 2005/0121324 A1 | 6/2005 | Park et al. |
| 2005/0129580 A1 | 6/2005 | Swinehart et al. |
| 2005/0130198 A1 | 6/2005 | Ammann et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0152808 A1 | 7/2005 | Ganesan |
| 2005/0158781 A1* | 7/2005 | Woudenberg ......... B01L 3/5027 435/6.11 |
| 2005/0170362 A1 | 8/2005 | Wada et al. |
| 2005/0186585 A1 | 8/2005 | Juncosa et al. |
| 2005/0196321 A1 | 9/2005 | Huang |
| 2005/0202470 A1 | 9/2005 | Sundberg et al. |
| 2005/0202489 A1 | 9/2005 | Cho et al. |
| 2005/0202504 A1 | 9/2005 | Anderson et al. |
| 2005/0205788 A1 | 9/2005 | Itoh |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0239127 A1 | 10/2005 | Ammann et al. |
| 2005/0266489 A1 | 12/2005 | Ammann et al. |
| 2005/0272079 A1 | 12/2005 | Burns et al. |
| 2005/0276728 A1 | 12/2005 | Muller-Cohn et al. |
| 2006/0002817 A1 | 1/2006 | Bohm et al. |
| 2006/0003373 A1 | 1/2006 | Ammann et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0058519 A1 | 3/2006 | Deggerdal et al. |
| 2006/0062696 A1 | 3/2006 | Chow et al. |
| 2006/0081539 A1 | 4/2006 | Safar et al. |
| 2006/0094004 A1* | 5/2006 | Nakajima ............. B01F 5/0647 435/5 |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0154341 A1 | 7/2006 | Chen |
| 2006/0165558 A1 | 7/2006 | Witty et al. |
| 2006/0165559 A1 | 7/2006 | Greenstein et al. |
| 2006/0166233 A1* | 7/2006 | Wu .................. B01L 3/502707 435/6.16 |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0205085 A1* | 9/2006 | Handique ............. C12Q 1/6806 435/287.2 |
| 2006/0207944 A1 | 9/2006 | Siddiqi |
| 2006/0210435 A1 | 9/2006 | Alavie et al. |
| 2006/0223169 A1 | 10/2006 | Bedingham et al. |
| 2006/0228734 A1 | 10/2006 | Vann et al. |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0014695 A1 | 1/2007 | Yue et al. |
| 2007/0020699 A1 | 1/2007 | Carpenter et al. |
| 2007/0020764 A1 | 1/2007 | Miller et al. |
| 2007/0026421 A1 | 2/2007 | Sundberg et al. |
| 2007/0042441 A1 | 2/2007 | Masters et al. |
| 2007/0048188 A1 | 3/2007 | Bigus |
| 2007/0054413 A1 | 3/2007 | Aviles et al. |
| 2007/0077643 A1 | 4/2007 | Nakamura et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1 | 7/2007 | Spaid et al. |
| 2007/0177147 A1 | 8/2007 | Parce |
| 2007/0178603 A1 | 8/2007 | Takii et al. |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0248958 A1 | 10/2007 | Jovanovich et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1 | 1/2008 | Maltezos et al. |
| 2008/0017306 A1 | 1/2008 | Liu et al. |
| 2008/0050804 A1 | 2/2008 | Handique et al. |
| 2008/0056948 A1 | 3/2008 | Dale et al. |

(56) References Cited

U.S. PATENT DOCUMENTS

| | | |
|---|---|---|
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0176230 A1 | 7/2008 | Owen et al. |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0240898 A1 | 10/2008 | Manz et al. |
| 2008/0247914 A1 | 10/2008 | Edens et al. |
| 2008/0257882 A1 | 10/2008 | Turner |
| 2008/0262213 A1 | 10/2008 | Wu et al. |
| 2008/0280285 A1* | 11/2008 | Chen ............ B01L 3/502715 435/5 |
| 2008/0308500 A1 | 12/2008 | Brassard |
| 2009/0047180 A1 | 2/2009 | Kawahara |
| 2009/0047713 A1 | 2/2009 | Handique |
| 2009/0066339 A1* | 3/2009 | Glezer ............... B01L 3/5027 324/444 |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0148933 A1* | 6/2009 | Battrell ............... B01F 11/0071 435/287.2 |
| 2009/0155123 A1 | 6/2009 | Williams et al. |
| 2009/0189089 A1 | 7/2009 | Bedingham et al. |
| 2009/0221059 A1 | 9/2009 | Williams et al. |
| 2009/0223925 A1 | 9/2009 | Morse et al. |
| 2009/0325164 A1 | 12/2009 | Vossenaar et al. |
| 2009/0325276 A1* | 12/2009 | Battrell ............... B01F 11/0071 435/287.2 |
| 2010/0009343 A1 | 1/2010 | Fischer et al. |
| 2010/0009351 A1 | 1/2010 | Brahmasandra et al. |
| 2010/0120129 A1 | 5/2010 | Amshey et al. |
| 2010/0173393 A1 | 7/2010 | Handique et al. |
| 2010/0233763 A1 | 9/2010 | Shigeura et al. |
| 2010/0284864 A1 | 11/2010 | Holenstein et al. |
| 2011/0008825 A1 | 1/2011 | Ingber et al. |
| 2011/0027151 A1 | 2/2011 | Handique et al. |
| 2011/0060136 A1 | 3/2011 | Matsunaga et al. |
| 2011/0097493 A1 | 4/2011 | Kerr et al. |
| 2011/0127292 A1 | 6/2011 | Sarofim et al. |
| 2011/0158865 A1 | 6/2011 | Miller et al. |
| 2011/0207140 A1 | 8/2011 | Handique et al. |
| 2011/0210257 A9 | 9/2011 | Handique et al. |
| 2011/0287447 A1 | 11/2011 | Norderhaug |
| 2011/0300033 A1 | 12/2011 | Battisti |
| 2012/0022695 A1 | 1/2012 | Handique et al. |
| 2012/0085416 A1 | 4/2012 | Ganesan |
| 2012/0122108 A1 | 5/2012 | Handique |
| 2012/0122231 A1 | 5/2012 | Tajima |
| 2012/0160826 A1 | 6/2012 | Handique |
| 2012/0171678 A1 | 7/2012 | Maltezos et al. |
| 2012/0171759 A1 | 7/2012 | Williams et al. |
| 2012/0183454 A1 | 7/2012 | Handique |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0101990 A1 | 4/2013 | Handique et al. |
| 2013/0164832 A1 | 6/2013 | Ganesan et al. |
| 2013/0183769 A1 | 7/2013 | Tajima |
| 2013/0210127 A1 | 8/2013 | Williams et al. |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |
| 2013/0288358 A1 | 10/2013 | Handique et al. |
| 2013/0315800 A1 | 11/2013 | Yin et al. |
| 2014/0120544 A1 | 5/2014 | Brahmasandra et al. |
| 2014/0206088 A1 | 7/2014 | Lentz et al. |
| 2014/0212882 A1 | 7/2014 | Handique et al. |
| 2014/0227710 A1 | 8/2014 | Handique et al. |
| 2014/0297047 A1 | 10/2014 | Ganesan et al. |
| 2014/0323357 A1 | 10/2014 | Handique et al. |
| 2014/0323711 A1 | 10/2014 | Brahmasandra et al. |
| 2014/0329301 A1 | 11/2014 | Handique et al. |
| 2014/0342352 A1 | 11/2014 | Handique et al. |
| 2014/0377850 A1 | 12/2014 | Handique et al. |
| 2015/0045234 A1 | 2/2015 | Stone et al. |
| 2015/0064702 A1 | 3/2015 | Handique et al. |
| 2015/0118684 A1 | 4/2015 | Wu et al. |
| 2015/0133345 A1 | 5/2015 | Handique et al. |
| 2015/0142186 A1 | 5/2015 | Handique et al. |
| 2015/0152477 A1 | 6/2015 | Ganesan et al. |
| 2015/0174579 A1 | 6/2015 | Iten et al. |
| 2015/0315631 A1 | 11/2015 | Handique et al. |
| 2015/0328638 A1 | 11/2015 | Handique et al. |
| 2015/0376682 A1 | 12/2015 | Handique |
| 2016/0038942 A1 | 2/2016 | Roberts |
| 2016/0102305 A1 | 4/2016 | Brahmasandra et al. |
| 2016/0107161 A1 | 4/2016 | Lentz et al. |
| 2016/0250635 A1 | 9/2016 | Handique |
| 2016/0250640 A1 | 9/2016 | Williams et al. |
| 2016/0333337 A1 | 11/2016 | Duffy et al. |
| 2017/0097373 A1 | 4/2017 | Williams et al. |
| 2017/0266666 A1 | 9/2017 | Lentz et al. |
| 2017/0275702 A1 | 9/2017 | Dahiya et al. |
| 2018/0017184 A1 | 1/2018 | Handique |
| 2018/0112252 A1 | 4/2018 | Handique |
| 2018/0119204 A1 | 5/2018 | Ganesan et al. |
| 2018/0135102 A1 | 5/2018 | Gubatayao et al. |
| 2018/0154364 A1 | 6/2018 | Handique et al. |
| 2018/0333722 A1 | 11/2018 | Handique |
| 2019/0054467 A1 | 2/2019 | Handique |
| 2019/0054471 A1 | 2/2019 | Williams et al. |
| 2019/0106692 A1 | 4/2019 | Brahmasandra et al. |
| 2019/0144849 A1 | 5/2019 | Duffy et al. |
| 2019/0145546 A1 | 5/2019 | Handique |
| 2019/0151854 A1 | 5/2019 | Baum et al. |
| 2019/0154719 A1 | 5/2019 | LaChance et al. |
| 2019/0284606 A1 | 9/2019 | Wu et al. |
| 2019/0324050 A1 | 10/2019 | Williams et al. |
| 2019/0390255 A1 | 12/2019 | Wu et al. |
| 2020/0010872 A1 | 1/2020 | Ganesan et al. |
| 2020/0139363 A1 | 5/2020 | Handique et al. |
| 2020/0291388 A1 | 9/2020 | Brahmasandra et al. |
| 2021/0001334 A1 | 1/2021 | Handique et al. |
| 2021/0047676 A1 | 2/2021 | Wu et al. |
| 2021/0071234 A1 | 3/2021 | Gubatayao et al. |
| 2021/0121887 A1 | 4/2021 | Handique et al. |
| 2021/0123090 A1 | 4/2021 | Handique et al. |
| 2021/0147923 A1 | 5/2021 | Steel et al. |
| 2021/0276008 A1 | 9/2021 | Handique et al. |
| 2021/0299663 A1 | 9/2021 | Handique |
| 2021/0317437 A1 | 10/2021 | Duffy et al. |
| 2021/0362155 A1 | 11/2021 | Williams et al. |
| 2022/0010364 A1 | 1/2022 | Handique et al. |
| 2022/0136034 A1 | 5/2022 | Handique et al. |

FOREIGN PATENT DOCUMENTS

| | | |
|---|---|---|
| AU | 4437602 | 7/2002 |
| AU | 4437702 | 7/2002 |
| AU | 764319 B2 | 8/2003 |
| CA | 2574107 | 9/1998 |
| CA | 2294819 | 1/1999 |
| CN | 1934451 | 3/2007 |
| CN | 1312287 C | 4/2007 |
| CN | 1942590 A | 4/2007 |
| CN | 1968754 A | 5/2007 |
| CN | 101466848 | 6/2009 |
| CN | 101522909 | 9/2009 |
| CN | 103540518 | 1/2014 |
| DE | 19755479 A1 | 6/1999 |
| DE | 19929734 | 12/1999 |

(56) References Cited

FOREIGN PATENT DOCUMENTS

| | | |
|---|---|---|
| DE | 19833293 C1 | 1/2000 |
| EP | 0136126 A2 | 4/1985 |
| EP | 0365828 A2 | 5/1990 |
| EP | 0483620 A2 | 5/1992 |
| EP | 0402994 B1 | 11/1994 |
| EP | 0393744 B1 | 1/1995 |
| EP | 0688602 A2 | 12/1995 |
| EP | 0707077 A2 | 4/1996 |
| EP | 0698046 B1 | 3/1997 |
| EP | 0766256 | 4/1997 |
| EP | 0772494 B1 | 5/1997 |
| EP | 0810030 A1 | 12/1997 |
| EP | 1059458 A2 | 12/2000 |
| EP | 1064090 A1 | 1/2001 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1621890 A1 | 2/2006 |
| EP | 1780290 A2 | 5/2007 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |
| JP | 58212921 A | 12/1983 |
| JP | S62-119460 | 5/1987 |
| JP | H01-502319 | 8/1989 |
| JP | 03-054470 | 3/1991 |
| JP | H 03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-173194 | 7/1996 |
| JP | H08-211071 | 8/1996 |
| JP | H08-285859 | 11/1996 |
| JP | H08-337116 | 12/1996 |
| JP | H09-304385 | 11/1997 |
| JP | H09-325151 | 12/1997 |
| JP | 2001-502790 | 1/1998 |
| JP | H01-219669 | 9/1998 |
| JP | H10-327515 | 12/1998 |
| JP | H 11-501504 | 2/1999 |
| JP | H 11503315 | 3/1999 |
| JP | 2000-514928 | 4/1999 |
| JP | H 11316226 | 11/1999 |
| JP | H11-515106 | 12/1999 |
| JP | 2000-180455 | 6/2000 |
| JP | 2000-266760 | 9/2000 |
| JP | 2000-275255 | 10/2000 |
| JP | 2001-502319 | 2/2001 |
| JP | 2001-204462 | 7/2001 |
| JP | 2001-509437 | 7/2001 |
| JP | 3191150 B2 | 7/2001 |
| JP | 2001-515216 | 9/2001 |
| JP | 2001-523812 | 11/2001 |
| JP | 2001-527220 | 12/2001 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-164279 | 6/2003 |
| JP | 2003-185584 | 7/2003 |
| JP | 2003-299485 | 10/2003 |
| JP | 2003-329693 | 11/2003 |
| JP | 2003-329696 | 11/2003 |
| JP | 2003-532382 A | 11/2003 |
| JP | 2004-003989 | 1/2004 |
| JP | 2004-506179 A | 2/2004 |
| JP | 2004-150797 A | 5/2004 |
| JP | 2004-283728 A | 10/2004 |
| JP | 2004-531360 A | 10/2004 |
| JP | 2004-533838 | 11/2004 |
| JP | 2004-534157 | 11/2004 |
| JP | 2004-361421 | 12/2004 |
| JP | 2004-536291 | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-176613 A | 7/2005 |
| JP | 2005-192439 | 7/2005 |
| JP | 2005-192554 | 7/2005 |
| JP | 2005-519751 | 7/2005 |
| JP | 2005-204661 | 8/2005 |
| JP | 2005-525816 | 9/2005 |
| JP | 2005-291954 A | 10/2005 |
| JP | 2005-323519 | 11/2005 |
| JP | 2005-533652 | 11/2005 |
| JP | 2005-535904 | 11/2005 |
| JP | 2006-021156 A | 1/2006 |
| JP | 2006-055837 A | 3/2006 |
| JP | 2006-094866 A | 4/2006 |
| JP | 2006-145458 | 6/2006 |
| JP | 2006-167569 | 6/2006 |
| JP | 2006-284409 | 10/2006 |
| JP | 2007-024742 A | 2/2007 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-514405 A | 6/2007 |
| JP | 2007-178328 | 7/2007 |
| JP | 2009-542207 | 12/2009 |
| JP | 3193848 U | 10/2014 |
| KR | 1020060044489 A | 5/2006 |
| RU | 2418633 | 5/2011 |
| WO | WO 88/06633 | 9/1988 |
| WO | WO 90/12350 | 10/1990 |
| WO | WO 92/05443 | 4/1992 |
| WO | WO 1994/005414 | 3/1994 |
| WO | WO 94/11103 | 5/1994 |
| WO | WO 1995/033846 | 12/1995 |
| WO | WO 1996/000228 | 1/1996 |
| WO | WO 96/04547 | 2/1996 |
| WO | WO 1996/018731 | 6/1996 |
| WO | WO 1996/039547 | 12/1996 |
| WO | WO 97/05492 | 2/1997 |
| WO | WO 1997/016835 | 5/1997 |
| WO | WO 97/21090 | 6/1997 |
| WO | WO 1997/022825 | 6/1997 |
| WO | WO 1997/027324 | 7/1997 |
| WO | WO 98/00231 | 1/1998 |
| WO | WO 1998/007019 | 2/1998 |
| WO | WO 98/22625 | 5/1998 |
| WO | WO 1998/35013 A1 | 8/1998 |
| WO | WO 1998/038487 | 9/1998 |
| WO | WO 98/49548 | 11/1998 |
| WO | WO 98/53311 | 11/1998 |
| WO | WO 1998/050147 | 11/1998 |
| WO | WO 99/01688 | 1/1999 |
| WO | WO 99/09042 | 2/1999 |
| WO | WO 99/12016 | 3/1999 |
| WO | WO 1999/017093 | 4/1999 |
| WO | WO 1999/029703 | 6/1999 |
| WO | WO 99/33559 | 7/1999 |
| WO | WO 1999/060397 | 11/1999 |
| WO | WO 2000/022436 | 4/2000 |
| WO | WO 2000/066783 | 11/2000 |
| WO | WO 2000/073412 | 12/2000 |
| WO | WO 2000/075623 | 12/2000 |
| WO | WO 2000/078455 | 12/2000 |
| WO | WO 01/005510 | 1/2001 |

(56) References Cited

FOREIGN PATENT DOCUMENTS

| | | |
|---|---|---|
| WO | WO 01/014931 | 3/2001 |
| WO | WO 01/027614 | 4/2001 |
| WO | WO 01/028684 | 4/2001 |
| WO | WO 2001/030995 | 5/2001 |
| WO | WO 01/041931 | 6/2001 |
| WO | WO 2001/046474 | 6/2001 |
| WO | WO 01/054813 | 8/2001 |
| WO | WO 01/089681 | 11/2001 |
| WO | WO 2001/089705 | 11/2001 |
| WO | WO 2001/092569 | 12/2001 |
| WO | WO 2002/043864 | 6/2002 |
| WO | WO 2002/048164 | 6/2002 |
| WO | WO 2002/052002 | 7/2002 |
| WO | WO 02/072264 | 9/2002 |
| WO | WO 02/078845 | 10/2002 |
| WO | WO 2002/086454 | 10/2002 |
| WO | WO 2002/094185 | 11/2002 |
| WO | WO 2003/007677 | 1/2003 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 03/076661 | 9/2003 |
| WO | WO 2003/078065 | 9/2003 |
| WO | WO 03/087410 | 10/2003 |
| WO | WO 2003/080868 | 10/2003 |
| WO | WO 04/007081 | 1/2004 |
| WO | WO 2004/010760 | 2/2004 |
| WO | WO 2004/048545 | 6/2004 |
| WO | WO 04/055522 | 7/2004 |
| WO | WO 2004/056485 A1 | 7/2004 |
| WO | WO 04/074848 | 9/2004 |
| WO | WO 2004/094986 | 11/2004 |
| WO | WO 2005/008255 | 1/2005 |
| WO | WO 05/011867 | 2/2005 |
| WO | WO 2005/030984 | 4/2005 |
| WO | WO 2005/072353 | 8/2005 |
| WO | WO 2005/094981 | 10/2005 |
| WO | WO 05/108620 | 11/2005 |
| WO | WO 2005/107947 | 11/2005 |
| WO | WO 2005/108571 | 11/2005 |
| WO | WO 2005/116202 | 12/2005 |
| WO | WO 2005/118867 | 12/2005 |
| WO | WO 2005/120710 | 12/2005 |
| WO | WO 06/010584 | 2/2006 |
| WO | WO 2006/032044 | 3/2006 |
| WO | WO 2006/035800 | 4/2006 |
| WO | WO 2006/043642 | 4/2006 |
| WO | WO 06/066001 | 6/2006 |
| WO | WO 06/079082 | 7/2006 |
| WO | WO 2006/081995 | 8/2006 |
| WO | WO 2006/113198 | 10/2006 |
| WO | WO 06/119280 | 11/2006 |
| WO | WO 2006/118420 | 11/2006 |
| WO | WO 07/044917 | 4/2007 |
| WO | WO 07/050327 | 5/2007 |
| WO | WO 07/064117 | 6/2007 |
| WO | WO 2007/075919 | 7/2007 |
| WO | WO 2007/091530 | 8/2007 |
| WO | WO 2007/112114 | 10/2007 |
| WO | WO 2007/120240 | 10/2007 |
| WO | WO 2007/120241 | 10/2007 |
| WO | WO 2008/005321 | 1/2008 |
| WO | WO 08/030914 | 3/2008 |
| WO | WO 08/060604 | 5/2008 |
| WO | WO 2008/134470 | 11/2008 |
| WO | WO 2008/149282 | 12/2008 |
| WO | WO 09/012185 | 1/2009 |
| WO | WO 2009/054870 A2 | 4/2009 |
| WO | WO 10/118541 | 10/2010 |
| WO | WO 2010/130310 | 11/2010 |
| WO | WO 2010/140680 | 12/2010 |
| WO | WO 2011/009073 | 1/2011 |
| WO | WO 2011/101467 | 8/2011 |

OTHER PUBLICATIONS

Tanaka et al., "Modification of DNA extraction from maize using polyamidoamine-dendrimer modified magnetic particles", Proceedings of the 74th Annual Meeting of the Electrochemical Society of Japan, Mar. 29, 2007; Faculty of Engineering, Science University of Tokyo; 2 pages.

Wu et al., "Polycationic dendrimers interact with RNA molecules: polyamine dendrimers inhibit the catalytic activity of Candida ribozymes", Chem Commun. (2005) 3: 313-315.

Zhou et al., "Cooperative binding and self-assembling behavior of cationic low molecular-weight dendrons with RNA molecules", Org Biomol Chem. (2006) 4(3): 581-585.

Zhou et al., "PANAM dendrimers for efficient siRNA delivery and potent gene silencing", Chem Comm.(Camb.) (2006) 22: 2362-2364.

Bollet, C. et al., "A simple method for the isolation of chromosomal DNA from Gram positive or acid-fast bacteria", Nucleic Acids Research, vol. 19, No. 8 (1991), p. 1955.

Brahmasandra et al., On-chip DNA detection in microfabricated separation systems, SPIE Conference on Microfluidic Devices and Systems, 1998, vol. 3515, pp. 242-251, Santa Clara, CA.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles et al., "Sample Filtration, Concentration, and Separation Integrated on Microfluidic Devices" Analytical Chemistry (American Chemical Society), (2003) 75(11): 2761-2767.

Burns et al., "An Integrated Nanoliter DNA Analysis Device", Science 282:484-487 (1998).

Chung et al., "Microfluidic chip for high efficiency DNA extraction", Miniaturisation for Chemistry, Biology & Bioengineering, vol. 4, No. 2 (Apr. 2004), pp. 141-147.

Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.

Handique et al, "Microfluidic flow control using selective hydrophobic patterning", SPIE, (1997) 3224: 185-194.

Handique et al., On-Chip Thermopneumatic Pressure for Discrete Drop Pumping, Analytical Chemistry, American Chemical Society, Apr. 15, 2001, vol. 73, No. 8, 1831-1838.

Handique, K. et al., "Nanoliter-volume discrete drop injection and pumping in microfabricated chemical analysis systems", Solid-State Sensor and ActuatorWorkshop (Hilton Head, South Carolina, Jun. 8-11, 1998) pp. 346-349.

Handique, K. et al., "Mathematical Modeling of Drop Mixing in a Slit-Type Microchannel", J. Micromech. Microeng., 11:548-554 (2001).

Handique, K. et al., "Nanoliter Liquid Metering in Microchannels Using Hydrophobic Patterns", Anal. Chem., 72(17):4100-4109 (2000).

He et al., Microfabricated Filters for Microfluidic Analytical Systems, Analytical Chemistry, American Chemical Society, 1999, vol. 71, No. 7, pp. 1464-1468.

Ibrahim et al., Real-Time Microchip PCR for Detecting Single-Base Differences in Viral and Human DNA, Analytical Chemistry, American Chemical Society, 1998, 70(9): 2013-2017.

Khandurina et al., Microfabricated Porous Membrane Structure for Sample Concentration and Electrophoretic Analysis, Analytical Chemistry American Chemical Society, 1999, 71(9): 1815-1819.

Kopp et al., Chemical Amplification: Continuous-Flow PCR on a Chip, www.sciencemag.org, 1998, vol. 280, pp. 1046-1048.

Kutter et al., Solid Phase Extraction on Microfluidic Devices, J. Microcolumn Separations, John Wiley & Sons, Inc., 2000, 12(2): 93-97.

Lagally et al., Single-Molecule DNA Amplification and Analysis in an Integrated Microfluidic Device, Analytical Chemistry, American Chemical Society, 2001, 73(3): 565-570.

(56) References Cited

OTHER PUBLICATIONS

Livache et al., "Polypyrrole DNA chip on a Silicon Device: Example of Hepatitis C Virus Genotyping", Analytical Biochemistry, (1998) 255: 188-194.
Mascini et al., "DNA electrochemical biosensors", Fresenius J. Anal. Chem., 369: 15-22, (2001).
Meyers, R.A., Molecular Biology and Biotechnology: A Comprehensive Desk Reference; VCH Publishers, Inc. New York, NY; (1995) pp. 418-419.
Nakagawa et al., Fabrication of amino silane-coated microchip for DNA extraction from whole blood, J of Biotechnology, Mar. 2, 2005, vol. 116, pp. 105-111.
Northrup et al., A Miniature Analytical Instrument for Nucleic Acids Based on Micromachined Silicon Reaction Chambers, Analytical Chemistry, American Chemical Society, 1998, 70(5): 918-922.
Oleschuk et al., Trapping of Bead-Based Reagents within Microfluidic Systems,: On-Chip Solid-Phase Extraction and Electrochromatography, Analytical Chemistry, American Chemical Society, 2000, 72(3): 585-590.
Plambeck et al., "Electrochemical Studies of Antitumor Antibiotics", J. Electrochem Soc.: Electrochemical Science and Technology (1984), 131(11): 2556-2563.
Roche et al. "Ectodermal commitment of insulin-producing cells derived from mouse embryonic stem cells" Faseb J (2005) 19: 1341-1343.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Shoffner et al., Chip PCR.I. Surface Passivation of Microfabricated Silicon-Glass Chips for PCR, Nucleic Acids Research, Oxford University Press, (1996) 24(2): 375-379.
Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Wang, "Survey and Summary, from DNA Biosensors to Gene Chips", Nucleic Acids Research, 28(16):3011-3016, (2000).
Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Yoza et al., "Fully Automated DNA Extraction from Blood Using Magnetic Particles Modified with a Hyperbranched Polyamidoamine Dendrimer", Journal of Bioscience and Bioengineering, 2003, 95(1): 21-26.
Yoza et al., DNA extraction using bacterial magnetic particles modified with hyperbranched polyamidoamine dendrimer, Mar. 20, 2003, 101(3): 219-228.
International Search Report and Written Opinion dated Feb. 4, 2013 for Application No. PCT/US2012/063091, filed Nov. 1, 2012.
Written Opinion (Rule 66) dated Oct. 24, 2013 for Application No. PCT/US2012/063091, filed Nov. 1, 2012.
International Preliminary Report on Patentability dated Jan. 23, 2014 for Application No. PCT/US2012/063091, filed Nov. 1, 2012.
Allemand et al., "pH-Dependent Specific Binding and Combing of DNA", Biophys J. (1997) 73(4): 2064-2070.
Harding et al., "DNA isolation using Methidium-Spermine-Sepharose", Meth Enzymol. (1992) 216: 29-39.
Harding et al., "Rapid isolation of DNA from complex biological samples using a novel capture reagent—methidium-spermine-sepharose", Nucl Acids Res. (1989) 17(17): 6947-6958.
Labchem; Sodium Hydroxide, 0,5N (0.5M); Safety Data Sheet, 2015; 8 pages.
Oh K.W. et al., "A Review of Microvalves", J Micromech Microeng. (2006) 16:R13-R39.
Cooley et al., "Applications of Ink-Jet Printing Technology to BioMEMS and Microfluidic Systems", Proceedings, SPIE Conference on Microfluids and BioMEMS, (Oct. 2001), 12 pages.
Kim et al., "Electrohydrodynamic Generation and Delivery of Monodisperse Picoliter Droplets Using a Poly(dimethylsiloxane) Microchip", Anal Chem. (2006) 78: 8011-8019.
Pal et al., "Phase Change Microvalve for Integrated Devices", Anal Chem. (2004) 76: 3740-3748.
Edwards, "Silicon (Si)," in "Handbook of Optical Constants of Solids" (Ghosh & Palik eds., 1997) in 24 pages.
Hale et al., "Optical constants of Water in the 200-nm to 200-µm Wavelength Region", Applied Optics, 12(3): 555-563 (1973).
Malitson, "Interspecimen Comparison of the Refractive Index of Fused Silica," J Optical Society of America, 55:1205-1209 (1965).
Palina et al., "Laser Assisted Boron Doping of Silicon Wafer Solar Cells Using Nanosecond and Picosecond Laser Pulses," 2011 37th IEEE Photovoltaic Specialists Conference, pp. 002193-002197, IEEE (2011).
Paulson et al., "Optical dispersion control in surfactant-free DNA thin films by vitamin B2 doping," Nature, Scientific Reports 8:9358 (2018) published at www.nature.com/scientificreports, Jun. 19, 2018.
Zhang et al., "PCR Microfluidic Devices for DNA Amplification," Biotechnology Advances, 24:243-284 (2006).
Zou et al., "A Micromachined Integratable Thermal Reactor," technical digest from International Electron Devices Meeting, IEEE, Washington, D.C., Dec. 2-5, 2001 (6 pages).
Petition for Inter Partes Review of U.S. Pat. No. 7,998,708 (Paper 1 in IPR2019-00488) dated Dec. 20, 2018 (94 pages).
Patent Owner Preliminary Response to Petition for Inter Partes Review of U.S. Pat. No. 7,998,708 and Exhibit List (Papers 5 and 6 in IPR2019-00488) dated Apr. 18, 2019 (79 pages).
Petition for Inter Partes Review of U.S. Pat. No. 8,323,900 (Paper 1 in IPR2019-00490) dated Dec. 20, 2018 (85 pages).
Patent Owner Preliminary Response to Petition for Inter Partes Review of U.S. Pat. No. 8,323,900 and Exhibit List (Papers 5 and 6 in IPR2019-00490) dated Apr. 18, 2019 (73 pages).
Declaration of Bruce K. Gale, Ph.D. (Exhibit 1001 in IPR2019-00488 and IPR2019-00490) dated Dec. 20, 2018 (235 pages).
Declaration of Michael G. Mauk, Ph.D. in Support of Patent Owner Preliminary Responses in IPR2019-00488 and IPR2019-00490 dated Apr. 18, 2019 (43 pages).
Mastrangelo et al., Microfabricated Devices for Genetic Diagnostics. Proceedings of the IEEE (1998) 86(8):1769-1787.
Sanchez et al., "Linear-After-The-Exponential (LATE)-PCR: An advanced method of asymmetric PCR and its uses in quantitative real-time analysis", PNAS (2004) 101(7): 1933-1938.
Decision instituting Inter Partes Review of U.S. Pat. No. 7,998,708 (Paper 8 in IPR2019-00488) dated Jul. 16, 2019 (20 pages).
Decision instituting Inter Partes Review of U.S. Pat. No. 8,323,900 (Paper 8 in IPR2019-00490) dated Jul. 16, 2019 (23 pages).
Becker H., "Hype, hope and hubris: the quest for the killer application in microfluidics", Lab on a Chip, The Royal Society of Chemistry (2009) 9:2119-2122.
Becker H., "Collective Wisdom", Lab on a Chip, The Royal Society of Chemistry (2010) 10:1351-1354.
Chaudhari et al., "Transient Liquid Crystal Thermometry of Microfabricated PCR Vessel Arrays", J Microelectro Sys., (1998) 7(4):345-355.
Chang-Yen et al., "Design, fabrication, and packaging of a practical multianalyte-capable optical biosensor," J Microlith Microfab Microsyst. (2006) 5(2):021105 in 8 pages.
Chen et al., "Total nucleic acid analysis integrated on microfluidic devices," Lab on a Chip. (2007) 7:1413-1423.
Cui et al., "Design and Experiment of Silicon PCR Chips," Proc. SPIE 4755, Design, Test, Integration, and Packaging of MEMS/MOEMS 2002, (Apr. 19, 2002) pp. 71-76.
Grunenwald H., "Optimization of Polymerase Chain Reactions," in Methods in Molecular Biology, PCR Protocols., Second Edition by Bartlett et al. [Eds.] Humana Press (2003) vol. 226, pp. 89-99.
Handal et al., "DNA mutation detection and analysis using miniaturized microfluidic systems", Expert Rev Mol Diagn. (2006) 6(1):29-38.
Irawan et al., "Cross-Talk Problem on a Fluorescence Multi-Channel Microfluidic Chip System," Biomed Micro. (2005) 7(3):205-211.

(56) References Cited

OTHER PUBLICATIONS

Khandurina et al., "Bioanalysis in microfluidic devices," J Chromatography A, (2002) 943:159-183.
Liao et al., "Miniature RT-PCR system for diagnosis of RNA-based viruses," Nucl Acids Res. (2005) 33(18):e156 in 7 pages.
Lin et al., "Thermal Uniformity of 12-in Silicon Wafer During Rapid Thermal Processing by Inverse Heat Transfer Method," IEEE Transactions on Semiconductor Manufacturing, (2000) 13(4):448-456.
Manz et al., "Miniaturized Total Chemical Analysis Systems: a Novel Concept for Chemical Sensing," Sensors and Actuators B1, (1990) 244-248.
Minco, "Conductive Heating Technologies for Medical Diagnostic Equipment," (2006) in 13 pages.
Picard et al., Laboratory Detection of Group B *Streptococcus* for Prevention of Perinatal Disease, Eur. J. Clin. Microbiol. Infect. Dis., Jul. 16, 2004, 23: 665-671.
Rohsenow et al. [Eds.], Handbook of Heat Transfer, 3rd Edition McGraw-Hill Publishers (1998) Chapters 1 & 3; p. 108.
Shen et al., "A microchip-based PCR device using flexible printed circuit technology," Sensors and Actuators B (2005), 105:251-258.
Spitzack et al., "Polymerase Chain Reaction in Miniaturized Systems: Big Progress in Little Devices", in Methods in Molecular Biology—Microfluidic Techniques, Minteer S.D. [Ed.] Humana Press (2006), pp. 97-129.
Squires et al., "Microfluidics: Fluid physics at the nanoliter scale", Rev Modern Phys. (2005) 77:977-1026.
Velten et al., "Packaging of Bio-MEMS: Strategies, Technologies, and Applications," IEEE Transactions on Advanced Packaging, (2005) 28(4):533-546.
Zhang et al., "Miniaturized PCR chips for nucleic acid amplification and analysis: latest advances and future trends," Nucl Acids Res., (2007) 35(13):4223-4237.
Patent Owner's Response in Inter Partes Review of U.S. Pat. No. 8,323,900 and Exhibit List (Paper 25 in IPR2019-00490) dated Oct. 16, 2019 (80 pages).
Patent Owner's Response in Inter Partes Review of U.S. Pat. No. 7,998,708 and Exhibit List (Paper 25 in IPR 2019-00488) dated Oct. 16, 2019 (93 pages).
Transcript of Deposition of Bruce K. Gale, Ph.D., in Support of Patent Owner's Responses (Exhibit 2012 in IPR2019-00488 and IPR2019-00490), taken Sep. 24, 2019 (124 pages).
Declaration of M. Allen Northrup, Ph.D. in Support of Patent Owner's Responses (Exhibit 2036 in IPR2019-00488 and IPR2019-00490) dated Oct. 16, 2019 (365 pages).
Complaint filed by *Becton, Dickinson and Company et al.*, v. *NeuModx Molecular, Inc*. on Jun. 18, 2019 in U.S. District Court, Delaware, Case #1:19-cv-01126-LPS, Infringement Action involving U.S. Patent Nos. 7,998,708; 8,273,308; 8,323,900; 8,415,103; 8,703,069; and U.S. Pat. No. 8,709,787 (29 pages).
Answer to Complaint filed by NeuModx Molecular, Inc. on Aug. 9, 2019 in U.S. District Court, Delaware, Case #1:19-cv-01126-LPS (24 pages).
Amended Answer to Complaint filed by NeuModx Molecular, Inc. on Oct. 4, 2019 in U.S. District Court, Delaware, Case #1:19-cv-01126-LPS (31 pages).
Altet et al., [Eds.] "Thermal Transfer and Thermal Coupling in IC's", Thermal Testing of Integrated Circuits; Chapter 2 (2002) Springer Science pp. 23-51.
Ateya et al., "The good, the bad, and the tiny: a review of microflow cytometry", Anal Bioanal Chem. (2008) 391(5):1485-1498.
Auroux et al., "Miniaturised nucleic acid analysis", Lab Chip. (2004) 4(6):534-546.
Baechi et al., "High-density microvalve arrays for sample processing in PCR chips", Biomed Microdevices. (2001) 3(3):183-190.
Baker M., "Clever PCR: more genotyping, smaller volumes." Nature Methods (May 2010) 70(5):351-356.
Becker H. "Fabrication of Polymer Microfluidic Devices", in Biochip Technology (2001), Chapter 4, pp. 63-96.

Becker H., "Microfluidic Devices Fabricated by Polymer Hot Embossing," in Integrated Microfabricated Biodevices: Advanced Technologies for Genomics, Drug Discovery, Bioanalysis, and Clinical Diagnostics (2002), Chapter 13, 32 pages.
Becker H., "Microfluidics: A Technology Coming of Age", Med Device Technol. (2008) 19(3):21-24.
Becker et al., "Portable CE system with contactless conductivity detection in an injection molded polymer chip for on-site food analysis", SPIE Proceedings MOEMS-MEMS 2008 Micro and Nanofabrication (2008) vol. 6886 in 8 pages.
Belgrader et al., "Rapid PCR for Identity Testing Using a Battery-Powered Miniature Thermal Cycler", J Forensic Sci. (1998) 43(2):315-319.
Belgrader et al., "A minisonicator to rapidly disrupt bacterial spores for DNA analysis.", Anal Chem. (1999) 71(19):4232-4236.
Belgrader et al., "Real-time PCR Analysis on Nucleic Acids Purified from Plasma Using a Silicon Chip", Micro Total Analysis Systems 2000 (pp. 525-528). Springer, Dordrecht.
Belgrader et al., "A microfluidic cartridge to prepare spores for PCR analysis", Biosens Bioelectron. (2000) 14(10-11):849-852.
Belgrader et al., "A Battery-Powered Notebook Thermal Cycler for Rapid Multiplex Real-Time PCR Analysis", Anal Chem. (2001) 73(2):286-289.
Belgrader et al., "Rapid and Automated Cartridge-based Extraction of Leukocytes from Whole Blood for Microsatellite DNA Analysis by Capillary Electrophoresis", Clin Chem. (2001) 47(10):1917-1933.
Belgrader et al., "A Rapid, Flow-through, DNA Extraction Module for Integration into Microfluidic Systems", Micro Total Analysis Systems (2002) pp. 697-699). Springer, Dordrecht.
Belgrader et al., "Development of a Battery-Powered Portable Instrumentation for Rapid PCR Analysis", in Integrated Microfabicated Devices, (2002) Ch. 8, pp. 183-206, CRC Press.
Bell M., "Integrated Microsystems in Clinical Chemistry", in Integrated Microfabicated Devices, (2002) Ch. 16, pp. 415-435, CRC Press.
Berthier et al., "Managing evaporation for more robust microscale assays Part 1. Volume loss in high throughput assays", Lab Chip (2008) 8(6):852-859.
Berthier et al., "Managing evaporation for more robust microscale assays Part 2. Characterization of convection and diffusion for cell biology", Lab Chip (2008) 8(6):860-864.
Berthier et al., "Microdrops", in Microfluidics for Biotechnology (2006), Chapter 2, pp. 51-88.
Biomerieux Press Release: "bioMérieux—2018 Financial Results," dated Feb. 27, 2019, accessed at www.biomerieux.com, pp. 13.
Blanchard et al., "Micro structure mechanical failure characterization using rotating Couette flow in a small gap", J Micromech Microengin. (2005) 15(4):792-801.
Blanchard et al., "Single-disk and double-disk viscous micropumps", Sensors and Actuators A (2005) 122:149-158.
Blanchard et al., "Performance and Development of a Miniature Rotary Shaft Pump", J Fluids Eng. (2005) 127(4):752-760.
Blanchard et al., "Single-disk and double-disk viscous micropump", ASME 2004 Inter'l Mechanical Engineering Congress & Exposition, Nov. 13-20, 2004, Anaheim, CA, IMECE2004-61705:411-417.
Blanchard et al., "Miniature Single-Disk Viscous Pump (Single-DVP), Performance Characterization", J Fluids Eng. (2006) 128(3):602-610.
Brahmasandra et al., "Microfabricated Devices for Integrated DNA Analysis", in Biochip Technology by Cheng et al., [Eds.] (2001) pp. 229-250.
Bu et al., "Design and theoretical evaluation of a novel microfluidic device to be used for PCR", J Micromech Microengin. (2003) 13(4):S125-S130.
Cady et al., "Real-time PCR detection of Listeria monocytogenes using an integrated microfluidics platform", Sensors Actuat B. (2005) 107:332-341.
Carlen et al., "Paraffin Actuated Surface Micromachined Valve," in IEEE MEMS 2000 Conference, Miyazaki, Japan, (Jan. 2000) pp. 381-385.

(56) References Cited

OTHER PUBLICATIONS

Carles et al., "Polymerase Chain Reaction on Microchips" in Methods in Molecular Biology—Microfluidic Techniques, Reviews & Protocols by Minteer S.D. [Ed.] Humana Press (2006), vol. 321; Chapter 11, pp. 131-140.
Chang-Yen et al., "A novel integrated optical dissolved oxygen sensor for cell culture and micro total analysis systems", IEEE Technical Digest MEMS International Conference Jan. 24, 2002, 4 pages.
Chang-Yen et al., "A PDMS microfluidic spotter for fabrication of lipid microarrays", IEEE 3rd EMBS Special Topic Conference May 12-15, 2005; 2 pages.
Chang-Yen et al., "Design and fabrication of a multianalyte-capable optical biosensor using a multiphysics approach", IEEE 3rd EMBS Special Topic Conference May 12-15, 2005; 2 pages.
Chang-Yen et al., "A Novel PDMS Microfluidic Spotter for Fabrication of Protein Chips and Microarrays", IEEE J of Microelectromech Sys. (2006) 15(5): 1145-1151.
Chang-Yen et al., "Spin-assembled nanofilms for gaseous oxygen sensing." Sens Actuators B: Chemical (2007), 120(2):426-433.
Chen P-C., "Accelerating micro-scale PCR (polymerase chain reactor) for modular lab-on-a-chip system", LSU Master's Theses—Digital Commons, (2006) 111 pages.
Cheng et al., "Biochip-Based Portable Laboratory", Biochip Tech. (2001):296-289.
Cho et al., "A facility for characterizing the steady-state and dynamic thermal performance of microelectromechanical system thermal switches", Rev Sci Instrum. (2008) 79(3):034901-1 to -8.
Chong et al., "Disposable Polydimethylsioxane Package for 'Bio-Microfluidic System'", IEEE Proceedings Electronic Components and Technology (2005); 5 pages.
Chou et al., "A miniaturized cyclic PCR device—modeling and experiments", Microelec Eng. (2002) 61-62:921-925.
Christel et al., "Nucleic Acid Concentration and PCR for Diagnostic Applications", in Micro Total Analysis Systems. (1998) D.J. Harrison et al. [Eds.] pp. 277-280.
Christel et al., "Rapid, Automated Nucleic Acid Probe Assays Using Silicon Microstructures for Nucleic Acid Concentration", J Biomech Eng. (1999) 121(1):22-27.
Christensen et al., "Characterization of interconnects used in PDMS microfluidic systems", J Micromech Microeng. (2005) 15:928 in 8 pages.
Crews et al., "Rapid Prototyping of a Continuous-Flow PCR Microchip", Proceedings of the AiChE Annual Meeting(Nov. 15, 2006) (335a) 3 pages.
Crews et al., Thermal gradient PCR in a continuous-flow microchip. In Microfluidics, BioMEMS, and Medical Microsystems V; Jan. 2007; vol. 6465, p. 646504; 12 pages.
Crews et al., "Continuous-flow thermal gradient PCR", Biomed Microdevices. (2008) 10(2):187-195.
Cui et al., "Electrothermal modeling of silicon PCR chips", In MEMS Design, Fabrication, Characterization, and Packaging, (Apr. 2001) (vol. 4407, pp. 275-280.
Danaher Press Release: "Danaher to Acquire Cepheid for $53.00 per share, or approximately $4 Billion," dated Sep. 6, 2016, accessed at www.danaher.com, pp. 3.
Demchenko A.P., "The problem of self-calibration of fluorescence signal in microscale sensor systems", Lab Chip. (2005) 5(11):1210-1223.
Dineva et al., "Sample preparation: a challenge in the development of point-of-care nucleic acid-based assays for resource-limited settings", Analyst. (2007) 132(12):1193-1199.
Dishinger et al., "Multiplexed Detection and Applications for Separations on Parallel Microchips", Electophoresis. (2008) 29(16):3296-3305.
Dittrich et al., "Single-molecule fluorescence detection in microfluidic channels—the Holy Grail in muTAS?", Anal Bioanal Chem. (2005) 382(8):1771-1782.
Dittrich et al., "Lab-on-a-chip: microfluidics in drug discovery", Nat Rev Drug Discov. (2006) 5(3):210-208.
Dunnington et al., "Approaches to Miniaturized High-Throughput Screening of Chemical Libraries", in Integrated Microfabricated Devices, (2002) Ch. 15, pp. 371-414, CRC Press.
Eddings et al., "A PDMS-based gas permeation pump for on-chip fluid handling in microfluidic devices", J Micromech Microengin. (2006) 16(11):2396-2402.
Edwards et al., "Micro Scale Purification Systems for Biological Sample Preparation", Biomed Microdevices (2001) 3(3):211-218.
Edwards et al., "A microfabricated thermal field-flow fractionation system", Anal Chem. (2002) 74(6):1211-1216.
Ehrlich et al., "Microfluidic devices for DNA analysis", Trends Biotechnol. (1999) 17(8):315-319.
El-Ali et al., "Simulation and experimental validation of a SU-8 based PCR thermocycler chip with integrated heaters and temperature sensor", Sens Actuators A: Physical (2004) 110(1-3):3-10.
Erickson et al., "Joule heating and heat transfer in poly(dimethylsiloxane) microfluidic systems", Lab Chip (2003) 3(3):141-149.
Erickson et al., "Integrated Microfluidic Devices", Analytica Chim Acta. (2004) 507:11-26.
Erill et al., "Development of a CMOS-compatible PCR chip: comparison of design and system strategies", J Micromech Microengin. (2004) 14(11):1-11.
Fair R.B., Digital microfluidics: is a true lab-on-a-chip possible? Microfluidics Nanofluid. (2007) 3:245-281.
Fan et al., "Integrated Plastic Microfluidic Devices for Bacterial Detection", in Integrated Biochips for DNA Analysis by Liu et al. [Eds], (2007) Chapter 6, pp. 78-89.
Fiorini et al., "Disposable microfluidic devices: fabrication, function, and application", Biotechniques (2005) 38(3):429-446.
Frazier et al., "Integrated micromachined components for biological analysis systems", J Micromech. (2000) 1(1):67-83.
Gale et al., "Micromachined electrical field-flow fractionation (mu-EFFF) system", IEEE Trans Biomed Eng. (1998) 45(12):1459-1469.
Gale et al., "Geometric scaling effects in electrical field flow fractionation. 1. Theoretical analysis", Anal Chem. (2001) 73(10):2345-2352.
Gale et al., "BioMEMS Education at Louisiana Tech University", Biomed Microdevices, (2002) 4:223-230.
Gale et al., "Geometric scaling effects in electrical field flow fractionation. 2. Experimental results", Anal Chem. (2002) 74(5):1024-1030.
Gale et al., "Cyclical electrical field flow fractionation", Electrophoresis. (2005) 26(9):1623-1632.
Gale et al., "Low-Cost MEMS Technologies", Elsevier B.V. (2008), Chapter 1.12; pp. 342-372.
Garst et al., "Fabrication of Multilayered Microfluidic 3D Polymer Packages", IEEE Proceedings Electronic Components & Tech, Conference May/Jun. 2005, pp. 603-610.
Gärtner et al., "Methods and instruments for continuous-flow PCR on a chip", Proc. SPIE 6465, Microfluidics, BioMEMS, and Medical Microsystems V, (2007) 646502; 8 pages.
Giordano et al., "Toward an Integrated Electrophoretic Microdevice for Clinical Diagnostics", in Integrated Microfabricated Biodevices: Advanced Technologies for Genomics, Drug Discovery, Bioanalysis, and Clinical Diagnostics (2002) Chapter 1; pp. 1-34.
Graff et al., "Nanoparticle Separations Using Miniaturized Field-flow Fractionation Systems", Proc. Nanotechnology Conference and Trade Show (NSTI) (2005); pp. 8-12.
Greer et al., "Comparison of glass etching to xurography prototyping of microfluidic channels for DNA melting analysis", J Micromech Microengin. (2007) 17(12):2407-2413.
Guijt et al., "Chemical and physical processes for integrated temperature control in microfluidic devices", Lab Chip. (2003) 3(1):1-4.
Gulliksen A., "Microchips for Isothermal Amplification of RNA", Doctoral Thesis (2007); Department of Mol. Biosciences—University of Oslo; 94 pages.
Guttenberg et al., "Planar chip device for PCR and hybridization with surface acoustic wave pump", Lab Chip. (2005) 5(3):308-317.
Haeberle et al., "Microfluidic platforms for lab-on-a-chip applications", Lab Chip. (2007) 7(9):1094-1110.

(56) References Cited

OTHER PUBLICATIONS

Hansen et al., "Microfluidics in structural biology: smaller, faster . . . better", Curr Opin Struct Biol. (2003) 13(5):538-544.
Heid et al., "Genome Methods—Real Time Quantitative PCR", Genome Res. (1996) 6(10):986-994.
Henry C.S. [Ed], "Microchip Capillary electrophoresis", Methods in Molecular Biology, Humana Press 339 (2006) Parts I-IV in 250 pages.
Herr et al., "Investigation of a miniaturized capillary isoelectric focusing (cIEF) system using a full-field detection approach", Solid State Sensor and Actuator Workshop, Hilton Head Island (2000), pp. 4-8.
Herr et al., "Miniaturized Isoelectric Focusing (µIEF) As a Component of a Multi-Dimensional Microfluidic System", Micro Total Analysis Systems (2001) pp. 51-53.
Herr et al., Miniaturized Capillary Isoelectric Focusing (cIEF): Towards a Portable High-Speed Separation Method. In Micro Total Analysis Systems (2000) Springer, Dordrecht; pp. 367-370.
Holland et al., "Point-of-care molecular diagnostic systems—past, present and future", Curr Opin Microbiol. (2005) 8(5):504-509.
Hong et al., "Integrated nanoliter systems", Nat Biotechnol. (2003) 21(10):1179-1183.
Hong et al., "Molecular biology on a microfluidic chip", J Phys.: Condens Matter (2006) 18(18):S691-S701.
Hong et al., "Integrated Nucleic Acid Analysis in Parallel Matrix Architecture", in Integrated Biochips for DNA Analysis by Liu et al. [Eds], (2007) Chapter 8, pp. 107-116.
Horsman et al., "Forensic DNA Analysis on Microfluidic Devices: A Review", J Forensic Sci. (2007) 52(4):784-799.
Hsieh et al., "Enhancement of thermal uniformity for a microthermal cycler and its application for polymerase chain reaction", Sens Actuators B: Chemical. (2008) 130(2):848-856.
Huang et al., "Temperature Uniformity and DNA Amplification Efficiency in Micromachined Glass PCR Chip", TechConnect Briefs; Tech Proc. of the 2005 NSTI Nanotechnology Conference and Trade Show. (2005) vol. 1:452-455.
Huebner et al., "Microdroplets: A sea of applications?", Lab Chip. (2008) 8(8):1244-1254.
Iordanov et al., "PCT Array on Chip—Thermal Characterization", IEEE Sensors (2003) Conference Oct. 22-24, 2003; pp. 1045-1048.
Ji et al., "DNA Purification Silicon Chip", Sensors and Actuators A: Physical (2007) 139(1-2):139-144.
Jia et al., "A low-cost, disposable card for rapid polymerase chain reaction", Colloids Surfaces B: Biointerfaces (2007) 58:52-60.
Kaigala et al., "An inexpensive and portable microchip-based platform for integrated RT-PCR and capillary electophoresis", The Analyst (2008) 133(3):331-338.
Kajiyama et al., "Genotyping on a Thermal Gradient DNA Chip", Genome Res. (2003) 13(3):467-475.
Kang et al., "Simulation and Optimization of a Flow-Through Micro PCR Chip", NSTI—Nanotech (2006) vol. 2, pp. 585-588.
Kantak et al.,"Microfluidic platelet function analyzer for shear-induced platelet activation studies", 2nd Annual International IEEE-EMBS Special Topic Conference on Microtechnologies in Med and Biol. (May 2002) 5 pages.
Kantak et al., "Microfabricated cyclical electrical field flow fractionation", 7th International Conference on Miniaturized Chomical and Biochem Analysis Sys. (2003) pp. 1199-1202.
Kantak et al., "Platelet function analyzer: Shear activation of platelets in microchannels", Biomedical Microdevices (2003) 5(3):207-215.
Kantak et al., "Characterization of a microscale cyclical electrical field flow fractionation system", Lab Chip. (2006) 6(5):645-654.
Kantak et al., "Effect of carrier ionic strength in microscale cyclical electrical field-flow fractionation", Anal Chem. (2006) 78(8):2557-2564.
Kantak et al., "Improved theory of cyclical electrical field flow fractions", Electrophoresis (2006) 27(14):2833-2843.
Karunasiri et al.,"Extraction of thermal parameters of microbolometer infrared detectors using electrical measurement", SPIE's Inter'l Symposium on Optical Science, Engineering, and Instrumentation; Proceedings (1998) vol. 3436, Infrared Technology and Applications XXIV; (1998) 8 pages.
Kelly et al., "Microfluidic Systems for Integrated, High-Throughput DNA Analysis," Analytical Chemistry, (2005), 97A-102A, Mar. 1, 2005, in 7 pages.
Kim et al., "Reduction of Microfluidic End Effects In Micro-Field Flow Fractionation Channels", Proc. MicroTAS 2003, pp. 5-9.
Kim et al., "Multi-DNA extraction chip based on an aluminum oxide membrane integrated into a PDMS microfluidic structure", 3rd IEEE/EMBS Special Topic Conference on Microtechnology in Med and Biol. (May 2005).
Kim et al., "Geometric optimization of a thin film ITO heater to generate a uniform temperature distribution", (2006), Tokyo, Japan; pp. 293-295; Abstract.
Kim et al., "Micro-Raman thermometry for measuring the temperature distribution inside the microchannel of a polymerase chain reaction chip", J Micromech Microeng. (2006) 16(3):526-530.
Kim et al., "Patterning of a Nanoporous Membrane for Multi-sample DNA Extraction", J Micromech Microeng. (2006) 16:33-39.
Kim et al., "Performance evaluation of thermal cyclers for PCR in a rapid cycling condition", Biotechniques. (2008) 44(4):495-505.
Kim et al., "Quantitative and qualitative analysis of a microfluidic DNA extraction system using a nanoporous AlO(x) membrane", Lab Chip. (2008) 8(9):1516-1523.
Kogi et al., "Microinjection-microspectroscopy of single oil droplets in water: an application to liquid/liquid extraction under solution-flow conditions", Anal Chim Acta. (2000) 418(2):129-135.
Kopf-Sill et al., "Creating a Lab-on-a-Chip with Microfluidic Technologies", in Integrated Microfabricated Biodevices: Advanced Technologies for Genomics, Drug Discovery, Bioanalysis, and Clinical Diagnostics (2002) Chapter 2; pp. 35-54.
Kricka L.J., "Microchips, Bioelectronic Chips, and Gene Chips—Microanalyzers for the Next Century", in Biochip Technology by Cheng et al. [Eds]; (2006) Chapter 1, pp. 1-16.
Krishnan et al., "Polymerase chain reaction in high surface-to-volume ratio SiO2 microstructures", Anal Chem. (2004) 76(22):6588-6593.
Kuswandi et al., "Optical sensing systems for microfluidic devices: a review", Anal Chim Acta. (2007) 601(2):141-155.
Lagally et al., "Genetic Analysis Using Portable PCR-CE Microsystem", Proceedings 7th International Conference on Miniaturized Chemical and Biochemical Analysis Systems (2003) pp. 1283-1286.
Lagally et al., "Integrated portable genetic analysis microsystem for pathogen/infectious disease detection", Anal Chem. (2004) 76(11):3152-3170.
Lauerman L.H., "Advances in PCR technology", Anim Health Res Rev. (2004) 5(2):247-248.
Lawyer et al., "High-level Expression, Purification, and Enzymatic Characterization of Full-length Thermus aquaticus DNA Polymerase and a Truncated Form Deficient in 5'to 3'Exonuclease Activity." Genome research (1993) 2(4):275-287.
Lee et al., "Submicroliter-volume PCR chip with fast thermal response and very power consumption", 7th International Conference on Miniaturized Chemical and Biochemical Analysis Systems, (2003) pp. 187-190.
Lee et al., "Bulk-micromachined submicroliter-volume PCR chip with very rapid thermal response and low power consumption", Lab Chip. (2004) 4(4):401-407.
Lewin et al., "Use of Real-Time PCR and Molecular Beacons to Detect Virus Replication in Human Immunodeficiency Virus Type 1-infected Individuals on Prolonged Effective Antiretroviral Therapy". J Virol. (1999) 73(7), 6099-6103.
Li et al., "Effect of high-aspect-ratio microstructures on cell growth and attachment", 1st Annual Inter'l IEEE-EMBS Special Topic Conference on Microtechnologies in Med and Biol. Proceedings Cat. No. 00EX451; (Oct. 2000) Poster 66, pp. 531-536.
Li PCH., "Micromachining Methods et al." in Microfluidic Lab-on-a-Chip for Chemical and Biological Analysis and Discovery, CRC Press (2005), Chapter 2-3 to 2-5; pp. 10-49.
Li PCH., "Microfluidic Flow" in Microfluidic Lab-on-a-Chip for Chemical and Biological Analysis and Discovery, CRC Press (2005), Chapter 3, pp. 55-99.

(56) References Cited

OTHER PUBLICATIONS

Li PCH., "Detection Methods" in Microfluidic Lab-on-a-Chip for Chemical and Biological Analysis and Discovery, CRC Press (2005), Chapter 7, pp. 187-249.

Li PCH., "Applications to Nucleic Acids Analysis" in Microfluidic Lab-on-a-Chip for Chemical and Biological Analysis and Discovery, CRC Press (2005), Chapter 9; pp. 293-325.

Li et al., "A Continuous-Flow Polymerase Chain Reaction Microchip With Regional Velocity Control", J Microelectromech Syst. (2006) 15(1):223-236.

Lien et al., "Integrated reverse transcription polymerase chain reaction systems for virus detection", Biosens Bioelectron. (2007) 22(8):1739-1748.

Lien et al., "Microfluidic Systems Integrated with a Sample Pretreatment Device for Fast Nucleic-Acid Amplification", J Microelectro Sys. (2008) 17(2):288-301.

Lifesciences et al., "Microfluidics in commercial applications; an industry perspective." Lab Chip (2006) 6:1118-1121.

Lin et al., "Simulation and experimental validation of micro polymerase chain reaction chips", Sens Actuators B: Chemical. (2000) 71(1-2):127-133.

Linder et al., "Microfluidics at the Crossroad with Point-of-care Diagnostics", Analyst (2007) 132:1186-1192.

Liu et al., "Integrated portable polymerase chain reaction-capillary electrophoresis microsystem for rapid forensic short tandem repeat typing", Anal Chem. (2007) 79(5):1881-1889.

Liu et al. [Eds], Integrated Biochips for DNA Analysis—Biotechnology Intelligence Unit; Springer/Landes Bioscience (2007) ISBN:978-0-387-76758-1; 216 pages.

Locascio et al., "ANYL 67 Award Address—Microfluidics as a tool to enable research and discovery in the life sciences", Abstract; The 236th ACS National Meeting (Aug. 2008); 2 pages.

Mahjoob et al., "Rapid microfluidic thermal cycler for polymerase chain reaction nucleic acid amplification", Inter'l J Heat Mass Transfer. (2008) 51(9-10):2109-2122.

Marcus et al., "Parallel picoliter rt-PCR assays using microfluidics", Anal Chem. (2006) 78(3):956-958.

Mariella R.P. Jr., "Microtechnology", Thrust Area Report FY 96 UCRL-ID-125472; Lawrence Livermore National Lab., CA (Feb. 1997) Chapter 3 in 44 pages.

Mariella R., "Sample preparation: the weak link in microfluidics-based biodetection", Biomed Microdevices. (2008) 10(6):777-784.

McMillan et al., "Application of advanced microfluidics and rapid PCR to analysis of microbial targets", In Proceedings of the 8th international symposium on microbial ecology (1999), in 13 pages.

Melin et al., "Microfluidic large-scale integration: the evolution of design rules for biological automation", Annu Rev Biophys Biomol Struct. (2007) 36:213-231.

Merugu et al., "High Throughput Separations Using a Microfabricated Serial Electric Split Ssystem" (2003), Proceedings of µTAS 2003, 7th International Conference on Miniaturized Chemical and Biochemical Analysis Systems, Oct. 5-9, 2003, Squaw Valley, California; 1191-1194, in 3 pages.

Miao et al., "Low cost micro-PCR array and micro-fluidic integration on single silicon chip", Int'l J Comput Eng Science (2003) 4(2):231-234.

Miao et al., "Flip-Chip packaged micro-plate for low cost thermal multiplexing", Int'l J Comput Eng Science. (2003) 4(2):235-238.

Micheletti et al., "Microscale Bioprocess Optimisation", Curr Opin Biotech. (2006) 17:611-618.

MicroTAS 2005., "Micro Total Analysis Systems", Proceedings 9th Int. Conference on Miniaturized Systems for Chemistry and Life Sciences; Presentations/Posters/Articles for Conference; Boston, MA in Oct. 10-12, 2005 in 1667 pages.

MicroTAS 2007., "Micro Total Analysis Systems", Proceedings 11th Int. Conference on Miniaturized Systems for Chemistry and Life Sciences; Presentations/Posters/Articles for Conference; Paris, France in Oct. 7-11, 2007 in 1948 pages.

MicroTAS 2007., "Micro Total Analysis Systems", Advance Program for the Proceedings 11th Int. Conference on Miniaturized Systems for Chemistry and Life Sciences; Presentations/Posters/Articles for Conference; Paris, France in Oct. 7-11, 2007 in 42 pages.

Mitchell et al., "Modeling and validation of a molded polycarbonate continuous-flow polymerase chain reaction device," Microfluidics, BioMEMS, and Medical Microsystems, Proc. SPIE (2003) 4982:83-98.

Myers et al., "Innovations in optical microfluidic technologies for point-of-care diagnostics", Lab Chip (2008) 8:2015-2031.

Namasivayam et al., "Advances in on-chip photodetection for applications in miniaturized genetic analysis systems", J Micromech Microeng. (2004) 14:81-90.

Narayanan et al., "A microfabricated electrical SPLITT system," Lab Chip, (2006) 6:105-114.

Neuzil et al., "Disposable real-time microPCR device: lab-on-a-chip at a low cost," Mol. Biosyst., (2006) 2:292-298.

Neuzil et al., "Ultra fast miniaturized real-time PCR: 40 cycles in less than six minutes," Nucleic Acids Research, (2006) 34(11)e77, in 9 pages.

Nguyen et al. [Eds], "Microfluidics for Internal Flow Control: Microfluidics" in Fundamentals and Applications of Microfluidics; 2nd Edition (2006) Introduction Chapter 1, pp. 1-9.

Nguyen et al. [Eds], "Microfluidics for Internal Flow Control: Microvalves" in Fundamentals and Applications of Microfluidics; (2006) 2nd Edition, Chapter 6, pp. 211-254.

Nguyen et al. [Eds], "Microfluidics for Internal Flow Control: Micropumps" in Fundamentals and Applications of Microfluidics; (2006) 2nd Edition, Chapter 7, pp. 255-309.

Nguyen et al. [Eds], "Microfluidics for Life Sciences and Chemistry: Microdispensers" in Fundamentals and Applications of Microfluidics; (2006), Chapter 11, pp. 395-418.

Nguyen et al. [Eds], "Microfluidics for Life Sciences and Chemistry: Microreactors" in Fundamentals and Applications of Microfluidics; (2006) 2nd Edition, Chapter 13, pp. 443-477.

Ning et al., "Microfabrication Processes for Silicon and Glass Chips", in Biochip Technology, CRC-Press (2006) Chapter 2, pp. 17-38.

Northrup et al., "A MEMs-based Miniature DNA Analysis System," Lawrence Livermore National Laboratory, (1995), submitted to Transducers '95, Stockholm, Sweden, Jun. 25-29, 1995, in 7 pages.

Northrup et al., "Advantages Afforded by Miniaturization and Integration of DNA Analysis Instrumentation," Microreaction Technology, (1998) 278-288.

Northrup et al., "A New Generation of PCR Instruments and Nucleic Acid Concentration Systems," in PCR Applications: Protocols for Functional Genomics, (1999), Chapter 8, pp. 105-125.

Northrup, "Microfluidics, A few good tricks," Nature materials (2004), 3:282-283.

Northrup et al., "Microfluidics-based integrated airborne pathogen detection systems," Abstract, Proceedings of the SPIE, (2006), vol. 6398, Abstract in 2 pages.

Oh et al., "World-to-chip microfluidic interface with built-in valves for multichamber chip-based PCR assays," Lab Chip, (2005), 5:845-850.

Ohno et al., "Microfluidics: Applications for analytical purposes in chemistry and biochemistry," Electrophoresis (2008), 29:4443-4453.

Pal et al., "Phase Change Microvalve for Integrated Devices," Anal. Chem. (2004), 76(13):3740-3748, Jul. 1, 2004, in 9 pages.

Pal et al., "An integrated microfluidic for influenza and other genetic analyses," Lab Chip, (2005), 5:1024-1032, in 9 pages.

Pamme, "Continuous flow separations in microfluidic devices," Lab Chip, (2007), 7:1644-1659.

Pang et al., "A novel single-chip fabrication technique for three-dimensional MEMS structures," Institute of Microelectronics, Tsinghua University, Beijing, P.R. China, (1998), IEEE, 936-938.

Pang et al., "The Study of Single-Chip Integrated Microfluidic System," Tsinghua University, Beijing, P.R. China, (1998), IEEE, 895-898.

Papautsky et al., "Effects of rectangular microchannel aspect ratio on laminar friction constant", in Microfluidic Devices and Systems II (1999) 3877:147-158.

(56) References Cited

OTHER PUBLICATIONS

Petersen, Kurt E., "Silicon as a Mechanical Material." Proceedings of the IEEE, (May 1982) 70(5):420-457.
Petersen et al., "Toward Next Generation Clinical Diagnostic Instruments: Scaling and New Processing Paradigms," Biomedical Microdevices (1998) 1(1):71-79.
Poser et al., "Chip elements for fast thermocycling," Sensors and Actuators A, (1997), 62:672-675.
Pourahmadi et al., "Toward a Rapid, Integrated, and Fully Automated DNA Diagnostic Assay for Chlamydia trachomatis and Neisseria gonorrhea," Clinical Chemistry, (2000), 46(9):1511-1513.
Pourahmadi et al., "Versatile, Adaptable and Programmable Microfluidic Platforms for DNA Diagnostics and Drug Discovery Assays," Micro Total Analysis Systems, (2000), 243-248.
Raisi et al., "Microchip isoelectric focusing using a miniature scanning detection system," Electrophoresis, (2001), 22:2291-2295.
Raja et al., "Technology for Automated, Rapid, and Quantitative PCR or Reverse Transcriptin-PCR Clinical Testing," Clinical Chemistry, (2005), 51(5):882-890.
Reyes et al., "Micro Total Analysis Systems. 1. Introduction, Theory, and Technology", Anal Chem (2002) 74:2623-2636.
Rodriguez et al., "Practical integration of polymerase chain reaction amplification and electrophoretic analysis in microfluidic devices for genetic analysis," Electrophoresis, (2003), 24:172-178.
Roper et al., "Advances in Polymer Chain Reaction on Microfluidic Chips," Anal. Chem., (2005), 77:3887-3894.
Ross et al., "Scanning Temperature Gradient Focusing for Simultaneous Concentration and Separation of Complex Samples," Micro Total Analysis Systems 2005, vol. 2, (2005), Proceedings of µTAS 2005, Ninth International Conference on Miniaturized Systems for Chemistry and Life Sciences, Oct. 9-13, 2005, Boston, Massachusetts; 1022-1024.
Ross et al., "Simple Device for Multiplexed Electrophoretic Separations Using Gradient Elution Moving Boundary Electrophoresis with Channel Current Detection," Anal. Chem., (2008), 80(24):9467-9474.
Sadler et al., "Thermal Management of BioMEMS: Temperature Control for Ceramic-Based PCR and DNA Detection Devices," IEEE Transactions on Components and Packaging Technologies, (2003) 26(2):309-316.
Sant et al., "An Integrated Optical Detector for Microfabricated Electrical Field Flow Fractionation System," Proceedings of µTAS 2003, 7th International Conference on Miniaturized Chemical and Biochemical Analysis Systems, Oct. 5-9, 2003, Squaw Valley, California; pp. 1259-1262.
Sant et al., "Geometric scaling effects on instrumental plate height in field flow fractionation", J Chromatography A (2006) 1104:282-290.
Sant H.J., "Reduction of End Effect-Induced Zone Broadening in Field-Flow Fractionation Channels", Anl Chem. (2006) 78:7978-7985.
Sant et al., "Microscale Field-Flow Fractionation: Theory and Practice", in Microfluidic Technologies for Miniaturized Analysis Systems. (2007) Chapter 12, pp. 4710521.
Schäferling et al., "Optical technologies for the read out and quality control of DNA and protein microarrays," Anal Bioanal Chem, (2006), 385: 500-517.
Serpengüzel et al., "Microdroplet identification and size measurement in sprays with lasing images", Optics express (2002) 10(20):1118-1132.
Shackman et al., "Gradient Elution Moving Boundary Electrophoresis for High-Throughput Multiplexed Microfluidic Devices," Anal. Chem. (2007), 79(2), 565-571.
Shackman et al., "Temperature gradient focusing for microchannel separations," Anal Bioanal Chem, (2007), 387:155-158.
Shadpour et al., "Multichannel Microchip Electrophoresis Device Fabricated in Polycarbonate with an Integrated Contact Conductivity Sensor Array," Anal Chem., (2007), 79(3), 870-878.
Sia et al., "Microfluidic devices fabricated in poly(dimethylsiloxane) for biological studies," Electrophoresis, (2003), 24:3563-3576.

Sigurdson M., "AC Electrokinetic Enhancement for Assay Enhancement", ProQuest LLC (2008) Doctoral Thesis UMI Microform 3319791 in 24 pages.
Singh et al., "PCR thermal management in an integrated Lab on Chip," Journal of Physics: Conference Series, (2006), 34:222-227.
Situma et al., "Merging microfluidics with microarray-based bioassays", Biomol Engin. (2006) 23:213-231.
Smith et al., "(576d) Micropatterned fluid lipid bilayers created using a continuous flow microspotter for multi-analyte assays," (2007), Biosensors II, 2007 AIChE Annual Meeting, Nov. 8, 2007, Abstract in 2 pages.
Sommer et al., "Introduction to Microfluidics", in Microfluidics for Biological Applications by Tian et al. [Eds] (2008) Chapter 1, pp. 1-34.
Squires et al., "Microfluidics: Fluid physics at the nanoliter scale," Reviews of Modern Physics, (2005), 77(3):977-1026.
Sundberg et al., "Solution-phase DNA mutation scanning and SNP genotyping by nanoliter melting analysis," Biomed Microdevices, (2007), 9:159-166, in 8 pages.
Tabeling, P. [Ed.], "Physics at the micrometric scale," in Introduction to Microfluidics (2005) Chapter 1, pp. 24-69.
Tabeling, P. [Ed.], "Hydrodynamics of Microfluidic Systems", in Introduction to Microfluidics; (2005) Chapter 2, pp. 70-129.
Tabeling, P. [Ed.], Introduction to Microfluidics; (2005) Chapters 5-7, pp. 216-297.
Taylor et al., Fully Automated Sample Preparation for Pathogen Detection Performed in a Microfluidic Cassette, in Micro Total Analysis Systems, Springer (2001), pp. 670-672.
Taylor et al., "Lysing Bacterial Spores by Sonication through a Flexible Interface in a Microfluidic System," Anal. Chem., (2001), 73(3):492-496.
Taylor et al., "Microfluidic Bioanalysis Cartridge with Interchangeable Microchannel Separation Components," (2001), The 11th International Conference on Solid-State Sensors and Actuators, Jun. 10-14, 2001, Munich, Germany; 1214-1247.
Taylor et al., "Disrupting Bacterial Spores and Cells using Ultrasound Applied through a Solid Interface," (2002), 2nd Annual International IEEE-EMBS Special Topic Conference on Microtechnologies in Medicine & Biology, May 2-4, 2002, Madison, Wisconsin; 551-555.
Thorsen et al., "Microfluidic Large-scale integration," Science, (2002), 298:580-584.
Toriello et al., "Multichannel Reverse Transcription-Polymerase Chain Reaction Microdevice for Rapid Gene Expression and Biomarker Analysis," Anal. Chem., (2006) 78(23):7997-8003.
Ugaz et al., "Microfabricated electrophoresis systems for DNA sequencing and genotyping applications," Phil. Trans. R. Soc. Lond. A, (2004), 362:1105-1129.
Ugaz et al., "PCR in Integrated Microfluidic Systems", in Integrated Biochips for DNA Analysis by Liu et al. [Eds]; (2007) Chapter 7, pp. 90-106.
Ullman et al., "Luminescent oxygen channeling assay (LOCI™): sensitive, broadly applicable homogeneous immunoassay method". Clin Chem. (1996) 42(9), 1518-1526.
Vinet et al., "Microarrays and microfluidic devices: miniaturized systems for biological analysis," Microelectronic Engineering, (2002), 61-62:41-47.
Wang et al., "From biochips to laboratory-on-a-chip system", in Genomic Signal Processing and Statistics by Dougherty et al. [Eds]; (2005) Chapter 5, pp. 163-200.
Wang et al., "A disposable microfluidic cassette for DNA amplification and detection", Lab on a Chip (2006) 6(1):46-53.
Wang et al., "Micromachined Flow-through Polimerase Chain Reaction Chip Utilizing Multiple Membrane-activated Micropumps," (2006), MEMS 2006, Jan. 22-26, 2006, Istanbul, Turkey; 374-377.
Woolley A.T., "Integrating Sample Processing and Detection with Microchip Capillary Electrophoresis of DNA", in Integrated Biochips for DNA Analysis by Liu et al. [Eds]; (2007) Chapter 5, pp. 68-77.
Xiang et al., "Real Time PCR on Disposable PDMS Chip with a Miniaturized Thermal Cycler," Biomedical Microdevices, (2005), 7(4):273-279.
Xuan, "Joule heating in electrokinetic flow," Electrophoresis, (2008), 298:33-43.

(56) References Cited

OTHER PUBLICATIONS

Yang et al., "High sensitivity PCR assay in plastic micro reactors," Lab Chip, (2002), 2:179-187.
Yang et al., "An independent, temperature controllable-microelectrode array," Anal. Chem., (2004), 76(5):1537-1543.
Yang et al., "Cost-effective thermal isolation techniques for use on microfabricated DNA amplification and analysis devices," J Micromech Microeng, (2005), 15:221-230.
Yobas et al., Microfluidic Chips for Viral RNA Extraction & Detection, (2005), 2005 IEEE, 49-52.
Yobas et al., "Nucleic Acid Extraction, Amplification, and Detection on Si-Eased Microfluidic Platforms," IEEE Journal of Solid-State Circuits, (2007), 42(8):1803-1813.
Yoon et al., "Precise temperature control and rapid thermal cycling in a micromachined DNA polymer chain reaction chip," J. Micromech. Microeng., (2002), 12:813-823.
Zhang et al, "Temperature analysis of continuous-flow micro-PCR based on FEA," Sensors and Actuators 6, (2002), 82:75-81.
Zhang et al, "Continuous-Flow PCR Microfluidics for Rapid DNA Amplification Using Thin Film Heater with Low Thermal Mass," Analytical Letters, (2007), 40:1672-1685, in 15 pages.
Zhang et al, "Direct Adsorption and Detection of Proteins, Including Ferritin, onto Microlens Array Patterned Bioarrays," J Am Chem Soc., (2007), 129:9252-9253.
Zhang et al, "Micropumps, microvalves, and micromixers within PCR microfluidic chips: Advances and trens," Biotechnology Advances, (2007), 25:483-514.
Zhao et al, "Heat properties of an integrated micro PCR vessel," Proceedings of SPIE, (2001), International Conference on Sensor Technology, 4414:31-34.
Zou et al., "Micro-assembled multi-chamber thermal cycler for low-cost reaction chip thermal multiplexing," Sensors and Actuators A, (2002), 102:114-121.
Zou et al., "Miniaturized Independently Controllable Multichamber Thermal Cycler," IEEE Sensors Journal, (2003), 3(6):774-780.
Petitioner's Reply to Patent Owner's Response to Petition in Inter Partes Review of U.S. Pat. No. 7,998,708 and Exhibit List (Paper 32 in IPR 2019-00488) dated Jan. 31, 2020 (34 pages).
Petitioner's Reply to Patent Owner's Response to Petition in Inter Partes Review of U.S. Pat. No. 8,323,900 and Exhibit List (Paper 32 in IPR 2019-00490) dated Jan. 31, 2020 (35 pages).
Second Declaration of Bruce K. Gale, Ph.D. (Exhibit 1026 in IPR2019-00488 and IPR2019-00490) dated Jan. 31, 2020 (91 pages).
Transcript of Deposition of M. Allen Northrup, Ph.D., (Exhibit 1027 in IPR2019-00488 and IPR2019-00490), taken Dec. 19, 2019 (109 pages).
Patent Owner's Sur-Reply in Inter Partes Review of U.S. Pat. No. 8,323,900 (Paper 42 in IPR2019-00490) dated Mar. 12, 2020 (39 pages).
Patent Owner's Sur-Reply in Inter Partes Review of U.S. Pat. No. 7,998,708 (Paper 43 in IPR 2019-00488) dated Mar. 12, 2020 (41 pages).
Transcript of Second Deposition of Bruce K. Gale, Ph.D., (Exhibit 2068 in IPR2019-00488 and IPR2019-00490), taken Feb. 19, 2020 (352 pages).
Anderson et al., "Microfluidic biochemical analysis system" Proc. 1997 IEEE Int. Conf. Solid-State Sens. Actuat. (1997) pp. 477-480.
Anderson et al., "Advances in Integrated Genetic Analysis" Micro Total Analysis Systems '98 Conference Proceedings, D. Kluwer Academic Publishers (1998) in 6 pages.
Anderson et al., "A Miniature Integrated Device for Automated Multistep Genetic Assays" Nucleic Acids Research (2000) 28(12), i-vi.
BDProbeTec™ ET Neisseria gonorrhoeae Amplified DNA Assay Package Insert, Jul. 2010 (13 pages).
BDProbeTec™ ET System Brochure, Aug. 2010 (9 pages).
Benters et al., "Dendrimer-Activated Solid Supports for Nucleic Acid and Protein Microarrays", ChemBioChem (2001) 2(9): 686-694.
Burns et al., "Microfabricated Structures for Integrated DNA Analysis" Proc. Natl. Acad. Sci. USA (May 1996) 93: 5556-5561.
Devarakonda et al., "The effect of PAMAM dendrimer generation size and surface functional group on the aqueous solubility of nifedipine", Int J Pharma. 284(1-2): 133-140.
Gill et al., "Nucleic Acid Isothermal Amplification Technologies—A Review", Nucleosides Nucleotides Nucleic Acids, (2008) 27(3): 224-243.
Harrison et al., "Capillary Electrophoresis and Sample Injection Systems Integrated on a Planar Glass Chip", Anal. Chem., (1992) 64: 1926-1932.
Hsueh et al., "A microfabricated, electrochemiluminescence cell for the detection of amplified DNA" Proc. 1995 IEEE Int. Conf. Solid-State Sens. Actuators (1995) pp. 768-771.
Hsueh et al., "DNA quantification with an electrochemiluminescence microcell" Proc. 1997 IEEE Int. Conf. Solid-State Sens. Actuators (1997) pp. 175-178.
Jiang et al., "Directing cell migration with asymmetric micropatterns" Proc. Natl. Acad. Sci. USA (2005) 102, 975-978.
Lagally et al., "Monolithic integrated microfluidic DNA amplification and capillary electrophoresis analysis system" Sensors and Actuators B (2000) 63:138-146.
Manz et al., "Design of an open-tubular column liquid chromatograph using silicon chip technology" Sensors and Actuators B (1990) 1:249-255.
Manz et al., "Planar chips technology for miniaturization and integration of separation techniques into monitoring systems: Capillary electrophoresis on a chip" Journal of Chromatography A (1992) 593:253-258.
Northrup et al., "A MEMS-based Miniature DNA Analysis System." Transducers '95—Eurosensors in Proc. 1995 (8th) IEEE Int. Conf. Solid-State Sens. Actuators, pp. 764-767.
Rhee et al., "Drop Mixing in a Microchannel for Lab-on-a-Chip Applications" Langmuir (2008) 24 (2): 590-601.
Rush et al., "Dispersion by Pressure-Driven Flow in Serpentine Microfluidic Channels", Ind Eng Chem Res., (2002) 41: 4652-4662.
Sammarco et al., "Thermocapillary Pumping of Discrete Drops in Microfabricated Analysis Devices" AIChE Journal (1999) 45(2): 350-366.
Taylor et al., "Optimization of the performance of the polymerase chain reaction in silicon-based microstructures" Nucleic Acids Res. (1997) vol. 25, pp. 3164-3168.
Terry et al., "A Gas Chromatographic Air Analyzer Fabricated on a Silicon Wafer" IEEE T Electron Dev (1979) 26:1880-1886.
U.S. Appl. No. 60/491,264, filed Jul. 31, 2003 (41 pages).
U.S. Appl. No. 60/491,269, filed Jul. 31, 2003 (52 pages).
U.S. Appl. No. 60/491,539, filed Aug. 1, 2003 (45 pages).
U.S. Appl. No. 60/553,553, filed Mar. 17, 2004 (49 pages).
U.S. Appl. No. 60/726,066, filed Oct. 11, 2005 (54 pages).
U.S. Appl. No. 60/786,007, filed Mar. 24, 2006 (223 pages).
U.S. Appl. No. 60/859,284, filed Nov. 14, 2006 (114 pages).
Walker et al., "Strand displacement amplification—an isothermal, in vitro DNA amplification technique", Nucleic Acids Res. (1992) 20(7): 1691-1696.
Whitesides G.M., "The origins and the future of microfluidics" Nature (2006) 442(7101):368-373.
Woias P., "Micropumps—past, progress and future prospects" Sensors and Actuators B (2005) 105, 28-38.
Woolley et al., "Functional integration of PCR amplification and capillary electrophoresis in a microfabricated DNA analysis device" Anal. Chem. (1996) vol. 68, pp. 4081-4086.
Wu et al., "Fabrication of Complex Three-dimensional Microchannel Systems in PDMS" J. Am. Chem. Soc. (2003) 125, 554-559.
Zhang et al., "Parallel DNA amplification by convective polymerase chain reaction with various annealing temperatures on a thermal gradient device," Analytical Biochemistry, (2009) 387:102-112.
Record of Oral Hearing in IPR2019-00488 and IPR2019-00490 held Apr. 21, 2020 (80 pages); Petitioner's Demonstratives for Oral Hearing in IPR2019-00488 and IPR2019-00490 held Apr. 21, 2020 (72 pages); Patent Owner's Demonstratives for Oral Hearing in IPR2019-00488 and IPR2019-00490 held Apr. 21, 2020 (88 pages);

(56) References Cited

OTHER PUBLICATIONS

Patent Owner's Objections to Petitioner's Oral Hearing Demonstratives in IPR2019-00488 and IPR2019-00490 dated Apr. 16, 2020 (4 pages).
Judgment/Final Written Decision Determining No Challenged Claims Unpatentable in Inter Partes Review of U.S. Pat. No. 7,998,708 (Paper No. 52 in IPR2019-00488) dated Jul. 14, 2020 (43 pages).
Judgment/Final Written Decision Determining No Challenged Claims Unpatentable in Inter Partes Review of U.S. Pat. No. 8,323,900 (Paper No. 51 in IPR2019-00490) dated Jul. 14, 2020 (43 pages).
Petitioner's Notice of Appeal in Inter Partes Review of U.S. Pat. No. 7,998,708 (Paper No. 54 in IPR2019-00488) dated Sep. 9, 2020 (48 pages).
Petitioner's Notice of Appeal in Inter Partes Review of U.S. Pat. No. 8,323,900 (Paper No. 53 in IPR2019-00490) dated Sep. 9, 2020 (48 pages).
Petition for Inter Partes Review of U.S. Pat. No. 8,273,308 (Paper 2 in IPR2020-01083) dated Jun. 12, 2020 (104 pages).
Petition for Inter Partes Review of U.S. Pat. No. 8,273,308 (Paper 2 in IPR2020-01091) dated Jun. 12, 2020 (105 pages).
Petition for Inter Partes Review of U.S. Pat. No. 8,803,069 (Paper 2 in IPR2020-01095) dated Jun. 12, 2020 (84 pages).
Petition for Inter Partes Review of U.S. Pat. No. 8,803,069 (Paper 3 in IPR2020-01100) dated Jun. 12, 2020 (83 pages).
Petition for Inter Partes Review of U.S. Pat. No. 8,709,787 (Paper 2 in IPR2020-01132) dated Jun. 18, 2020 (96 pages).
Petition for Inter Partes Review of U.S. Pat. No. 8,415,103 (Paper 2 in IPR2020-01133) dated Jun. 18, 2020 (96 pages).
Petition for Inter Partes Review of U.S. Pat. No. 8,709,787 (Paper 2 in IPR2020-01137) dated Jun. 19, 2020 (86 pages).
Petition for Inter Partes Review of U.S. Pat. No. 8,415,103 (Paper 2 in IPR2020-01136) dated Jun. 19, 2020 (85 pages).
Declaration of Mark A. Burns, Ph.D. (Exhibit N1001 in IPR2020-01083, IPR2020-01091, IPR2020-01095 and IPR2020-01100) dated Jun. 12, 2020 (378 pages).
Declaration of Mark A. Burns, Ph.D. (Exhibit N1101 in IPR2020-01132 and IPR2020-01133) dated Jun. 17, 2020 (253 pages).
Declaration of Mark A. Burns, Ph.D. (Exhibit N1201 in IPR2020-01136 and IPR2020-01137) dated Jun. 19, 2020 (205 pages).
Patent Owner's Preliminary Response to Petition for Inter Partes Review of U.S. Pat. No. 8,703,069 (Paper 13 in IPR2020-01095) dated Sep. 17, 2020 (77 pages).
Patent Owner's Preliminary Response to Petition for Inter Partes Review of U.S. Pat. No. 8,273,308 (Paper 13 in IPR2020-01091) dated Sep. 17, 2020 (70 pages).
Patent Owner's Preliminary Response to Petition for Inter Partes Review of U.S. Pat. No. 8,703,069 (Paper 14 in IPR2020-01100) dated Sep. 17, 2020 (59 pages).
Declaration of M. Allen Northrup, Ph.D. in Support of Patent Owner Preliminary Responses in IPR2020-01091, IPR2020-01095 and IPR2020-01100 (Exhibit H2003) dated Sep. 16, 2020 (137 pages).
Patent Owner's Preliminary Response to Petition for Inter Partes Review of U.S. Pat. No. 8,273,308 (Paper 13 in IPR2020-01083) dated Oct. 22, 2020 (88 pages).
Declaration of M. Allen Northrup, Ph.D. in support of Patent Owner Preliminary Responses in IPR2020-01083, IPR2020-01091, IPR2020-01095 and IPR2020-01100 (Exhibit H2003) dated Oct. 21, 2020 (171 pages).
Petition for Inter Partes Review of U.S. Pat. No. 10,625,262 (Paper 2 in IPR2021-00250) dated Nov. 25, 2020 (107 pages).
Petition for Inter Partes Review of U.S. Pat. No. 10,625,261 (Paper 2 in IPR2021 -00251) dated Nov. 25, 2020 (117 pages).
Petition for Inter Partes Review of U.S. Pat. No. 10,632,466 (Paper 2 in IPR2021-00253) dated Nov. 25, 2020 (121 pages).
Declaration of Mark A. Burns, Ph.D. (Exhibit N1001 in IPR2021-00250, IPR2021-00251 and IPR2021-00253) dated Nov. 24, 2020 (311 pages).
Declaration of James L. Mullins, Ph.D. (Exhibit N1029 in IPR2021-00250, IPR2021-00251, and IPR2021-00253) dated Nov. 18, 2020 (54 pages).
Decision Denying Institution of Inter Partes Review of U.S. Pat. No. 8,273,308 (Paper 14 in IPR2020-01091) dated Dec. 4, 2020 (21 pages).
Decision Denying Institution of Inter Partes Review of U.S. Pat. No. 8,703,069 (Paper 14 in IPR2020-01095) dated Dec. 4, 2020 (22 pages).
Decision Denying Institution of Inter Partes Review of U.S. Pat. No. 8,703,069 (Paper 15 in IPR2020-01100) dated Dec. 4, 2020 (19 pages).
Decision Denying Institution of Inter Partes Review of U.S. Pat. No. 8,273,308 (Paper 14 in IPR2020-01083) dated Jan. 7, 2021 (24 pages).
Patent Owner's Preliminary Response to Petition for Inter Partes Review of U.S. Pat. No. 8,415,103 (Paper 20 in IPR2020-01133) dated Jan. 20, 2021 (67 pages).
Patent Owner's Preliminary Response to Petition for Inter Partes Review of U.S. Pat. No. 8,709,787 (Paper 19 in IPR2020-01132) dated Jan. 20, 2021 (78 pages).
Declaration of M. Allen Northrup, Ph.D. in support of Patent Owner Preliminary Responses in IPR2020-01132 and IPR2020-01133 (Exhibit H2016) dated Jan. 20, 2021 (154 pages).
Patent Owner's Preliminary Response to Petition for Inter Partes Review of U.S. Pat. No. 8,415,103 (Paper 19 in IPR2020-01136) dated Jan. 20, 2021 (77 pages).
Patent Owner's Preliminary Response to Petition for Inter Partes Review of U.S. Pat. No. 8,709,787 (Paper 19 in IPR2020-01137) dated Jan. 20, 2021 (69 pages).
Declaration of M. Allen Northrup, Ph.D. in support of Patent Owner Preliminary Responses in IPR2020-01136 and IPR2020-01137 (Exhibit H2016) dated Jan. 20, 2021 (111 pages).
Opening Brief [Corrected] of Appellants Qiagen North American Holdings, Inc. and NeuMoDx Molecular Inc. in Appeals from the USPTO, PTAB, in Nos. IPR2019-00488, IPR2019-00490, IPR2019-01493 and IPR2019-01494 filed Jan. 22, 2021 in U.S. Court of Appeals for the Federal Circuit Case Nos. 20-2249, 20-2250, 20-2273 and 20-2276 (82 pages).
Decision Granting Institution of Inter Partes Review of U.S. Pat. No. 8,709,787 (Paper 20 in IPR2020-01132) dated Apr. 19, 2021 (33 pages).
Decision Denying Institution of Inter Partes Review of U.S. Pat. No. 8,415,103 (Paper 21 in IPR2020-01133) dated Apr. 19, 2021 (24 pages).
Decision Denying Institution of Inter Partes Review of U.S. Pat. No. 8,415,103 (Paper 20 in IPR2020-01136) dated Apr. 19, 2021 (19 pages).
Decision Denying Institution of Inter Partes Review of U.S. Pat. No. 8,709,787 (Paper 20 in IPR2020-01137) dated Apr. 19, 2021 (14 pages).
Patent Owner's Preliminary Response to Petition for Inter Partes Review of U.S. Pat. No. 10,625,262 (Paper 6 in IPR2021-00250) dated Apr. 19, 2021 (71 pages).
Patent Owner's Preliminary Response to Petition for Inter Partes Review of U.S. Pat. No. 10,625,261 (Paper 6 in IPR2021-00251) dated Apr. 19, 2021 (82 pages).
Patent Owner's Preliminary Response to Petition for Inter Partes Review of U.S. Pat. No. 10,632,466 (Paper 6 in IPR2021-00253) dated Apr. 19, 2021 (66 pages).
Declaration of James P. Landers, Ph.D. in support of Patent Owner Preliminary Responses in IPR2021-00250, IPR2021-00251, and IPR2021-00253 (Exhibit H2003) dated Apr. 19, 2021 (189 pages).
Brief for Appellee HandyLab, Inc. in Appeals from the USPTO, PTAB, in Nos. IPR2019-00488, IPR2019-00490, IPR2019-01493 and IPR2019-01494 filed May 24, 2021 in U.S. Court of Appeals for the Federal Circuit Case Nos. 20-2249, 20-2250, 20-2273 and 20-2276 (74 pages).
Reply Brief of Appellants Qiagen North American Holdings, Inc. and NeuMoDx Molecular, Inc. in Appeals from the USPTO, PTAB, in Nos. IPR2019-00488, IPR2019-00490, IPR2019-01493 and IPR2019-01494 filed Jun. 21, 2021 in U.S. Court of Appeals for the Federal Circuit Case Nos. 20-2249, 20-2250, 20-2273 and 20-2276 (44 pages).

(56) References Cited

OTHER PUBLICATIONS

Decision Denying Institution of Inter Partes Review of U.S. Pat. No. 10,625,262 (Paper 7 in IPR2021-00250) dated Jul. 15, 2021 (15 pages).
Decision Denying Institution of Inter Partes Review of U.S. Pat. No. 10,632,466 (Paper 7 in IPR2021-00253) dated Jul. 15, 2021 (22 pages).
Decision Denying Institution of Inter Partes Review of U.S. Pat. No. 10,625,261 (Paper 7 in IPR2021-00251) dated Jul. 15, 2021 (24 pages).
Patent Owner's Response in Inter Partes Review of U.S. Pat. No. 8,709,787 and Exhibit List (Paper 29 in IPR 2020-01132) dated Jul. 15, 2021 (87 pages).
Decision Granting Institution of Inter Partes Review of U.S. Pat. No. 8,415,103 on Rehearing (Paper 23 in IPR2020-01133) dated Aug. 6, 2021 (20 pages).
Decision of U.S. Court of Appeal for the Federal Circuit Affirming Inter Partes Review Final Written Decisions Determining No Challenged Claims of U.S. Pat. Nos. 7,998,708 and 8,323,900 are Unpatentable (IPR2019-00488, IPR2019-00490, IPR2019-01493, and IPR2019-01494) dated Oct. 29, 2021 (12 pages).
Joint Motion to Terminate Inter Partes Review of U.S. Pat. No. 8,709,787 (Paper 37 in IPR 2020-01132) dated Nov. 15, 2021 (8 pages).
Joint Motion to Terminate Inter Partes Review of U.S. Pat. No. 8,415,103 (Paper 35 in IPR 2020-01133) dated Nov. 15, 2021 (8 pages).
First Amended and Supplemental Complaint filed by Becton, Dickinson and Company et al. on Jun. 25, 2020 in U.S. District Court, Delaware, Case #1:19-cv-01126-LPS, Infringement Action involving U.S. Pat. Nos. 7,998,708; 8,273,308; 8,323,900; 8,415,103; 8,703,069; 8,709,787; 10,494,663; 10,364,456; 10,443,088; 10,604,788; 10,625,261; 10,625,262; and U.S. Pat. No. 10,632,466 (55 pages).
Answer to First Amended and Supplemental Complaint filed by NeuModx Molecular, Inc. on Jul. 16, 2020 in U.S. District Court, Delaware, Case #1:19-cv-01126-LPS (42 pages).
Defendant NeuModx's Initial Invalidity Contentions filed Sep. 30, 2020 in U.S. District Court, Delaware, Case #1:19-cv-01126-LPS (47 pages).
Defendant NeuModx's Joint Claim Construction Chart [Exhibit N1023] filed Oct. 21, 2020 in U.S. District Court, Delaware, Case #1:19-cv-01126-LPS (25 pages).
Defendant NeuModx's Amended Answer, Affirmative Defenses, and Counterclaims to Plaintiffs' First Amended and Supplemental Complaint filed Dec. 11, 2020 in U.S. District Court, Delaware, Case #1:19-cv-01126-LPS (43 pages).
Second Amended and Supplemental Complaint filed by Becton, Dickinson and Company et al. on Feb. 25, 2021 in U.S. District Court, Delaware, Case #1:19-cv-01126-LPS (75 pages).
Defendant NeuMoDx's First Supplemental Invalidity Contentions filed Mar. 17, 2021 in U.S. District Court, Delaware, Case #1:19-cv-01126-LPS (55 pages).
Defendant NeuMoDx's Answer, Affirmative Defenses, and Counterclaims to Plaintiffs' Second and Supplemental Complaint filed Mar. 18, 2021 in U.S. District Court, Delaware, Case #1:19-cv-01126-LPS (67 pages).
Plaintiffs' Answer and/or Reply to Defendants' Counterclaims and Counterclaims-In-Reply filed Apr. 22, 2021 in U.S. District Court, Delaware, Case #1:19-cv-01126-LPS (127 pages).
Claim Construction (Markman) Order dated May 10, 2021 in in U.S. District Court, Delaware, Case #1:19-cv-01126-LPS (30 pages).
Stipulation of Dismissal filed by Plaintiffs Becton, Dickinson and Company, Geneohm Sciences Canada, Inc. and HandyLab, Inc. and Defendants NeuMoDx Molecular, Inc., Qiagen GmbH, and Qiagen North American Holdings, Inc. on Nov. 12, 2021 in U.S. District Court, Delaware, Case # 1:19-cv-01226-LPS (3 pages).

\* cited by examiner

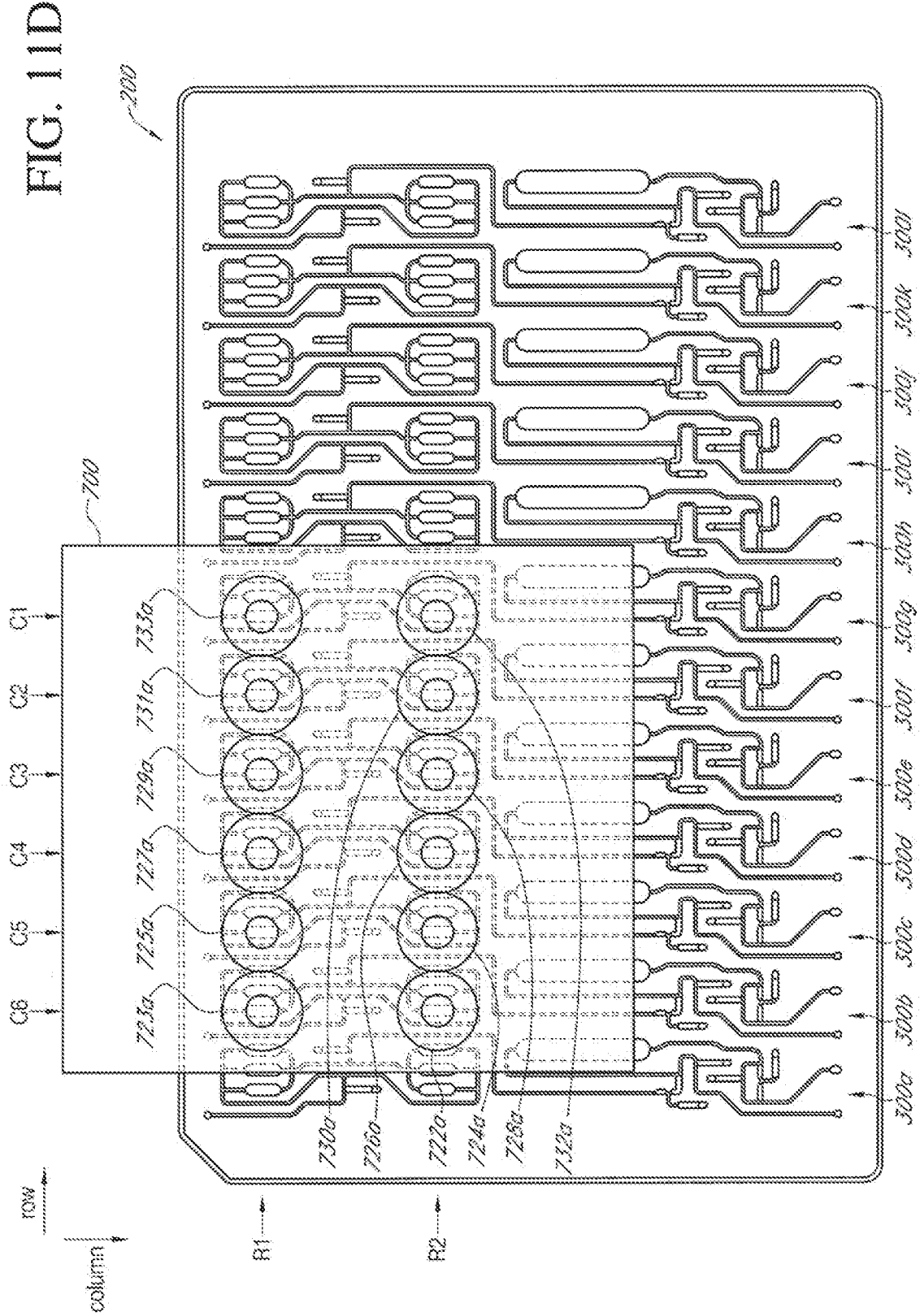

MULTIPLEXED DIAGNOSTIC DETECTION APPARATUS AND METHODS

CLAIM OF PRIORITY

The present application is a continuation of International Application No. PCT/US2012/063091, filed on Nov. 1, 2012, which claims priority to U.S. Provisional Application Ser. No. 61/556,032, filed Nov. 4, 2011. Each of the above applications is hereby incorporated by reference in its entirety.

STATEMENT REGARDING FEDERALLY SPONSORED METHODS

The research leading to the present invention was supported, at least in part, by a grant under U01AI070428 from the National Institutes of Health. Accordingly, the Government may have certain rights in the invention.

TECHNICAL FIELD

The apparatus and methods disclosed herein relate generally to the high-throughput, automated execution of nucleic acid based assays, such as Polymerase Chain Reaction (PCR) in a microfluidic cartridge.

BACKGROUND

The medical diagnostics industry is a critical element of today's healthcare infrastructure. At present, however, in vitro diagnostic analyses, no matter how routine, have become a bottleneck in patient care. There are several reasons for this. First, many diagnostic analyses can only be done with highly specialized equipment that is both expensive and only operable by trained clinicians. Such equipment may be found in only a few locations—often just one in any given urban area. This requires hospitals to send out samples for analyses to these locations, thereby incurring shipping costs and transportation delays, and possibly even sample loss or mishandling. Second, the equipment in question is typically not available "on-demand" but instead runs in batches, thereby delaying the processing time for many samples as they must wait for a machine to reach capacity before they can be run.

Understanding that diagnostic assays on biological samples may break down into several key steps, it is often desirable to automate one or more steps. For example, a biological sample, such as those obtained from a patient, can be used in nucleic acid amplification assays, in order to amplify a target nucleic acid (e.g., DNA, RNA, or the like) of interest. Once amplified, the presence of a target nucleic acid, or amplification product of a target nucleic acid (e.g., a target amplicon) reactor can be detected, wherein the presence of a target nucleic acid and/or target amplicon is used to identify and/or quantify the presence of a target (e.g., a target microorganism or the like). Often, nucleic acid amplification assays involve multiple steps, which can include nucleic acid extraction, nucleic acid amplification, and detection. It is desirable to automate certain steps of these processes.

There is a need for improved methods and devices for carrying out diagnostic assays on multiple biological samples in parallel. The embodiments described herein address this need and can advantageously be used in high throughput and multiplexed amplification and detection.

SUMMARY OF THE INVENTION

Certain embodiments disclosed herein contemplate a microfluidic cartridge having a plurality of sample lanes, each lane comprising a microfluidic network having, in fluid communication with one another, an inlet, an amplification chamber, a first amplification valve upstream of the amplification chamber and a second amplification valve downstream of the amplification chamber, a first amplification gate upstream of the amplification chamber and a second amplification gate downstream of the amplification chamber, a first channel leading from the inlet, via the first amplification valve and first amplification gate, to the amplification chamber, a plurality of detection chambers, a first detection valve upstream of the plurality of detection chambers and a second detection valve downstream of the plurality of detection chambers, and a second channel leading from the amplification chamber, via the second amplification gate and first detection valve, to the plurality of detection chambers.

Certain embodiments can further include a third channel in each of the microfluidic networks, the third channel leading from the amplification chamber, via the second amplification valve, to a first vent. Certain embodiments can further include a fourth channel in each of the microfluidic networks, the fourth channel leading from the plurality of detection chambers, via the second detection valve to a second vent.

Each of the plurality of sample lanes can be configured to amplify one or more polynucleotides independently of the other lanes and the amplification can be conducted by real-time amplification in the amplification chambers. Each of the inlets can be configured to accept a quantity of sample from a pipette tip and the quantity of each sample can be from 0.01-50 µl, e.g., 1-20 µl, such as 0.1 µl, 0.2 µl, 0.3 µl, 0.4 µl, 0.5 µl, 0.6 µl, 0.7 µl, 0.8 µl, 0.9 µl, 1 µl, 2 µl, 3 µl, 4 µl, 5 µl, 6 µl, 7 µl, 8 µl, 9 µl, 10 µl, 11 µl, 12 µl, 13 µl, 14 µl, 15 µl, 16 µl, 17 µl, 18 µl, 19 µl, 20 µl, or more, or any amount in between. The inlets of the respective plurality of sample lanes can be spaced apart from one another to permit simultaneous loading from a multiple-pipette head dispenser. The amplification valves can include a temperature responsive substance that melts upon heating to seal a channel that communicates with the amplification chamber. The detection valves can comprise a temperature responsive substance that melts upon heating in order to seal a channel that communicates with the plurality of detection chambers. The amplification gates can include a temperature responsive substance that melts upon heating to open a channel that communicates with the amplification chamber. The detection gates can comprise a temperature responsive substance that melts upon heating in order to open a channel that communicates with the plurality of detection chambers. The amplification chamber can have a volume of 1-25, e.g., 5-10 µl. The plurality of detection chambers can each have a volume less than the volume of the corresponding amplification chamber, e.g., approximately 1 µl-5 µl. In some embodiments, the microfluidic cartridge of can have 12 sample lanes. In some embodiments, the microfluidic cartridge can include one or more detection windows disposed over the detection chambers.

Certain embodiments disclosed herein contemplate a diagnostic apparatus comprised of the microfluidic cartridge, and which further includes a plurality of separately controllable amplification heat sources thermally coupled to the amplification chambers. The apparatus can further include a plurality of detection heat sources thermally coupled to the detection chambers, wherein each amplification valve and each detection valve comprises a separately controllable valve heat source thermally coupled thereto, and each amplification gate comprises a separately controllable gate heat source thermally coupled thereto.

The apparatus can further include a multiple-pipette head dispenser, wherein the dispenser can be configured to introduce a plurality of samples into the plurality of sample lanes simultaneously. The dispenser can be configured to apply physical pressure to the microfluidic cartridge in order to bring the cartridge and the heaters in thermal communication with each other. The dispenser can be configured to introduce fluidic pressure into the plurality of sample lanes in order to move the plurality of samples.

In some embodiments, the detection heat source for each detection chamber can be individually and separately controllable. In other embodiments, the detection heat sources can also be separately controllable in pairs, in threes, fours, fives, sixes, sevens, eights, nines, tens, elevens, twelves, etc., wherein. In some embodiments, the detection heat sources themselves can also be separately controllable as a group of heat sources associated with the detection chambers of one (or more) sample lane(s).

The apparatus can further include an detector head having plurality of detector pairs, wherein each detector pair is comprised of an LED and a photodiode and each detector pair can be configured to detect the presence of one or more analyte(s), e.g., target nucleic acids of an amplified sample in the detection chambers. Two detector pairs of the detector head can be aligned collinearly and configured to detect the presence of one or more analyte(s) in two detection chambers of the plurality (e.g., six) detection chambers associated with one sample lane.

Certain embodiments of the disclosure include a method of amplifying a target nucleic acid in a sample including providing a microfluidic network, introducing the sample into the microfluidic network, the network comprising an amplification chamber and a plurality of detection chambers downstream of the amplification chamber, isolating the sample in the amplification chamber by closing amplification valves in the microfluidic network upstream and downstream of the amplification chamber, thermal cycling the amplification chamber under amplification conditions to create an amplified sample, wherein the amplified sample comprises a target amplicon when the sample comprises the target nucleic acid, opening an amplification gate upstream of the amplification chamber; and moving the amplified sample downstream to the plurality of detection chambers.

In certain embodiments, isolating the sample in the amplification chamber by closing amplification valves can include heating a temperature responsive substance to seal one or more channels that communicate with the amplification chamber and opening an amplification gate upstream of the amplification chamber can include heating a temperature responsive substance to remove the substance from an upstream channel in communication with the amplification chamber. Moving the amplified sample downstream can include applying fluidic pressure to the network and applying fluidic pressure to the network can include discharging fluid from a pipette tip into an inlet of the microfluidic network. The fluid discharged from the pipette tip may be a gas.

The method of amplifying a target nucleic acid can also include isolating the sample in the plurality of detection chambers by closing detection valves upstream and downstream of the plurality of detection chambers and contacting the amplified sample in one of more of the plurality of detection chambers with a detection probe, wherein the detection probe is specific for the target amplicon. The method can also include detecting the presence of the target amplicon in the sample in at least one of the detection chambers, which can be performed by contacting the amplified sample with a detection probe, wherein the detection probe is specific for the target amplicon. The detection probe can include a fluorescent moiety, and detecting the presence of the target amplicon in the amplified sample can include emitting light from a light source to activate the detection probe, and measuring the fluorescence of the detection probe with a photodiode.

In certain embodiments of the disclosure, the method can also include applying physical pressure to the microfluidic network in order to place the network and one or more heat sources in thermal communication. Applying physical pressure can include applying a force from a pipette head dispenser on the microfluidic network. The method of amplifying a target nucleic acid in a sample can be performed simultaneously on a plurality of networks, the plurality of networks comprising a microfluidic cartridge.

The method can further include amplifying a second target nucleic acid in the sample, wherein the amplified sample can include a second target amplicon when the sample comprises the second target nucleic acid. The method can further include detecting the presence of the target amplicon, the second target amplicon, or both in at least one of the detection chambers. Detecting the presence of the second target amplicon can include contacting the amplified sample with a second detection probe, wherein the second detection probe is specific for the second target amplicon. The second detection probe can be a second fluorescent moiety, and detecting the presence of the second target amplicon in the amplified sample can include emitting light from a light source to activate the second detection probe, and measuring the fluorescence of the second detection probe with a photodiode. The first fluorescent moiety and the second fluorescent moiety can be the same or the first fluorescent moiety and the second fluorescent moiety can be different. The detection probe and the second detection probe can be a capture nucleic acid and second capture nucleic acid, respectively, and the $T_m$ of the detection probe and the second detection probe can be different. The detection probe can further include a quencher moiety. The second detection probe can include a second quencher moiety.

The thermal cycling can be an assay selected from the group consisting of: polymerase chain reaction, ligase chain reaction, nucleic acid sequence-based amplification, self-sustained sequence replication, strand displacement amplification, and branched DNA signal amplification. The thermal cycling can be a multiplex polymerase chain reaction. The thermal cycling of each of the plurality of networks can be independently controlled.

BRIEF DESCRIPTION OF THE DRAWINGS

FIGS. 11A-11D illustrate the movement of the detector head across the microfluidic cartridge.

DETAILED DESCRIPTION OF THE PREFERRED EMBODIMENT

Figure 1A:
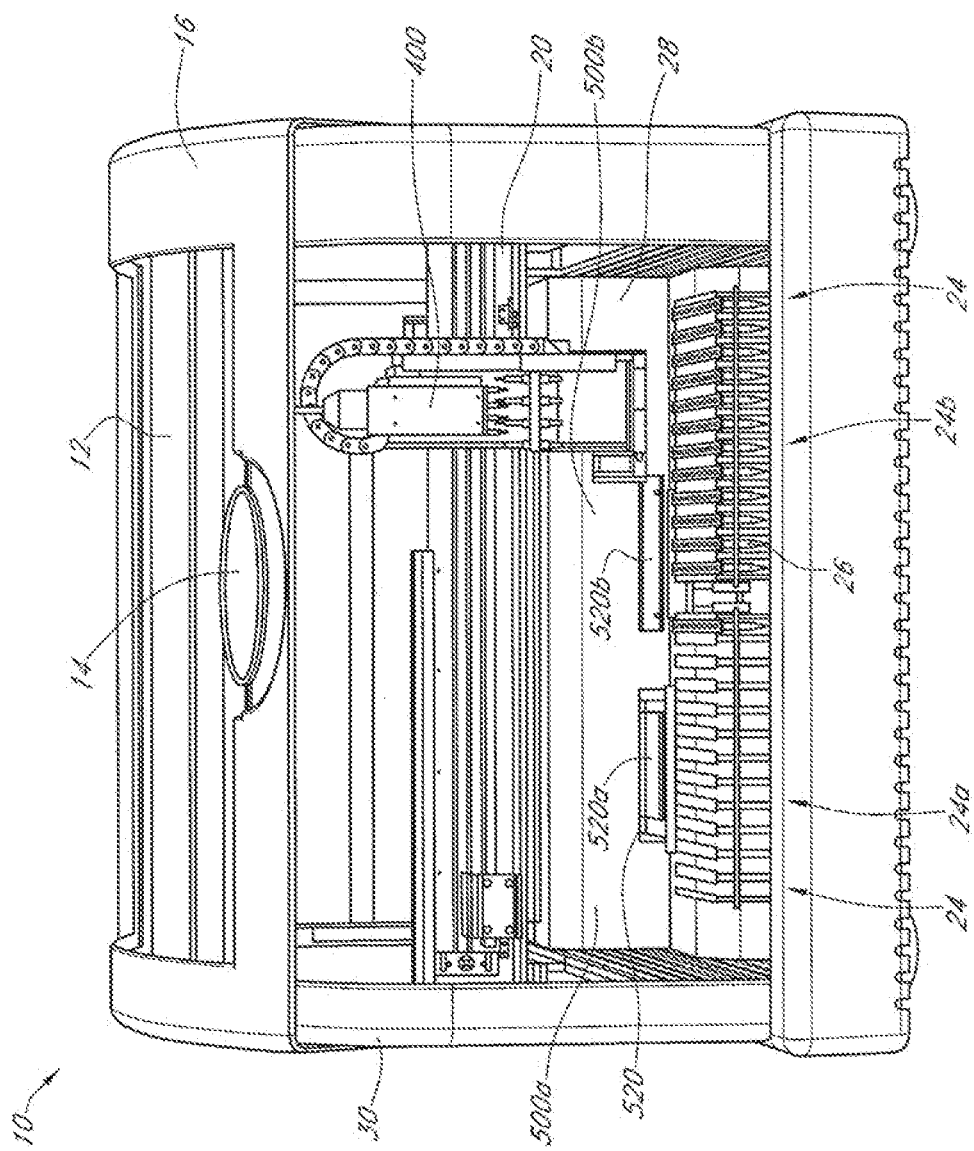
FIG. 1A is a front plan view of a diagnostic apparatus as used in certain of the embodiments.

Before the embodiments are further described, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges and are also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a method" includes a plurality of such methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms are used extensively. The following definitions are provided to facilitate understanding of the invention.

As used herein, the term "microfluidic" refers to volumes of less than 1 ml, preferably less than 0.9 ml, e.g., 0.8 ml, 0.7 ml, 0.6 ml, 0.5 ml, 0.4 ml, 0.3 ml, 0.2 ml, 0.1 ml, 90 µl, 80 µl, 70 µl, 60 µl, 50 µl, 40 µl, 30 µl, 20 µl, 10 µl, 5 µl, 4 µl, 3 µl, 2 µl, 1 µl, 0.9 µl, 0.8 µl, 0.7 µl, 0.6 µl, 0.5 µl, 0.4 µl, 0.3 µl, 0.2 µl, 0.1 µl, or less, e.g., nanoliter volumes in the range of 10-500 nanoliters, such as 100 nanoliters.

As used herein, the term "cartridge" refers to a unit that may be disposable, or reusable in whole or in part, and that is configured to be used in conjunction with some other apparatus that has been suitably and complementarily configured to receive and operate on (such as deliver energy to) the cartridge.

As used herein, the term "TRS", "thermo-responsive substance" or "temperature responsive substance" refers to a substance that changes physical character upon heating, and that is relatively immobile at a first temperature and more mobile at a second temperature. A mass of TRS can be an essentially solid mass or an agglomeration of smaller particles. Examples of TRS's include, but are not limited to a eutectic alloy (e.g., a solder), wax (e.g., an olefin), polymers, plastics, and combinations thereof. A TRS can also be a blend of variety of materials, such as an emulsion of thermoelastic polymer blended with air microbubbles (to enable higher thermal expansion, as well as reversible expansion and contraction), polymer blended with expancel material (offering higher thermal expansion), polymer blended with heat conducting microspheres (offering faster heat conduction and hence, faster melting profiles), or a polymer blended with magnetic microspheres (to permit magnetic actuation of the melted thermoresponsive material).

As used herein, the term "target nucleic acid" refers to a nucleic acid of interest. The term nucleic acid can refer to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

"Nucleic acid amplification assay" refers to any procedure that amplifies target nucleic acids from a template, including but not limited to polymerase chain reaction, e.g., multiplex PCR, ligase chain reaction (LCR), transcription-based amplification systems (TAS), self-sustained sequence replication (3SR), nucleic acid sequence-based amplification (NASBA), strand displacement amplification (SDA) and branched DNA (bDNA) (Persing et al. (1993) Diagnostic Molecular Microbiology: Principles and Applications (American Society for Microbiology, Washington, D.C.).

$T_m$, or "melting temperature" refers to the temperature at which half of a given number of nucleic acid duplexes have separated into single strands—a phenomenon also referred to as "denaturing" or "de-annealing." The melting temperature of a probe or primer—more precisely, the duplex formed by the probe or primer and a complementary single oligonucleotide strand—represents the single most widely used parameter to guide the design of probes and primers in assays involving hybridization. Many commercial software packages are available for this purpose, e.g., OLIGO™, VISUALOMP™, PRIMERSELECT™, ARRAY DESIGNER™, PRIMER3™, and others.

Diagnostic Apparatuses

Provided herein are diagnostic devices, or diagnostic apparatuses, that are configured to test whether an analyte of interest, e.g., a target nucleic acid, is present in a sample. More specifically, the diagnostic devices disclosed herein are configured for the amplification and/or detection of target nucleic acids in a sample, within a microfluidic cartridge.

In accordance with the embodiments disclosed herein, provided is a diagnostic device or diagnostic apparatus that comprises one or more of the following components: a microfluidic cartridge, a plurality of heat sources, a pipette-head dispenser, and an optical module. The components may be integral to the diagnostic device. Alternatively, the components may be removably incorporated into the device. For example, the microfluidic cartridge of the device can represent a removable/disposable component of the device as a whole, whereas the heat sources can be integral to the device.

The diagnostic devices disclosed herein are preferably configured to perform a plurality of nucleic acid amplification reactions in a plurality of microfluidic amplification chambers within a microfluidic cartridge, as well as to detect a plurality of target nucleic acids within a plurality of detection chambers within the microfluidic cartridge.

In some embodiments, the devices are configured to enable thermal cycling (e.g., cycles of heating and cooling) of amplification chambers and/or detection chambers within a microfluidic cartridge. Thermal cycling of the reaction chambers and detection chambers can be used to enable amplification of nucleic acids, e.g., target nucleic acids, as well as detection of nucleic acids, e.g., by observing the melting curves of amplified sample.

A PCR protocol may comprise guidelines for performing the successive annealing and denaturing of the polynucleotides in the reaction chamber prior to detection. Such guidelines, comprising a time profile for heating the chamber, may be referred to as a "protocol." In certain embodiments, the apparatus may comprise an aperture plate which facilitates consistent heating and cooling of various reaction chambers, e.g., amplification chambers and/or detection chambers within a microfluidic cartridge by applying pressure to the cartridge.

Figure 1B:
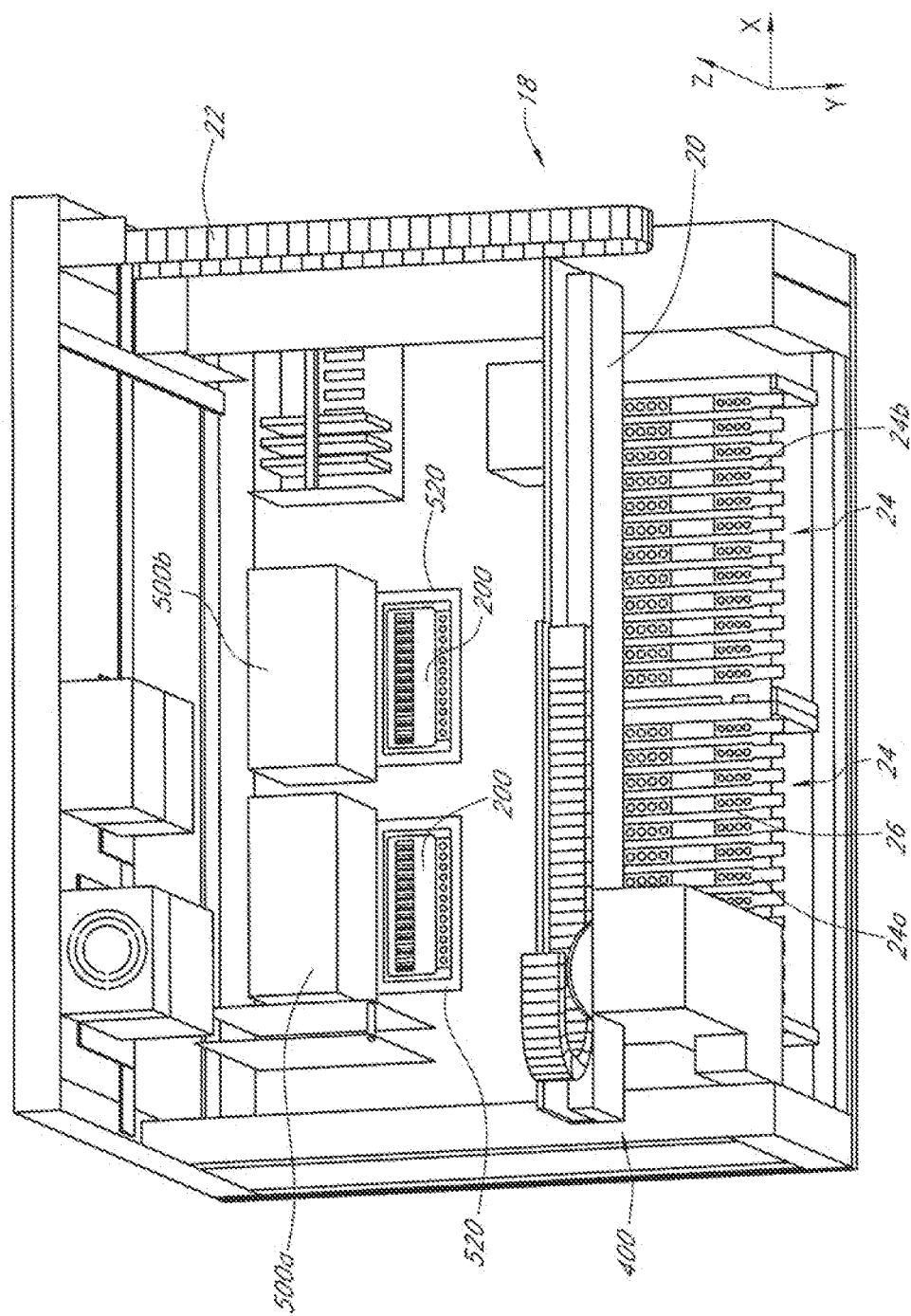
FIG. 1B is a top perspective view of the diagnostic apparatus of FIG. 1A showing certain internal components of the apparatus.

Turning to the figures, FIGS. 1A and 1B show a diagnostic apparatus 10 of certain of the present embodiments. In the embodiment illustrated in FIG. 1A, the diagnostic apparatus includes an apparatus housing 30. The housing 30 may ensure a controlled environment for processing of the microfluidic samples and for preventing undesirable light from entering the detection space. The housing 30 may comprise a cover 16 which includes a handle 14 and a translucent window 12. The cover 16 may be brought down to close the opening in the front of the diagnostic apparatus 10 when the diagnostic apparatus 10 is in operation.

As seen in the embodiments shown in FIGS. 1A and 1B, the diagnostic apparatus 10 may house two specimen racks 24a, 24b in a front portion of the diagnostic apparatus 10. The skilled artisan will appreciate, however, that the depiction of the diagnostic apparatus in FIGS. 1A and 1B is exemplary only, and that in some embodiments, the apparatus can be configured to house more than two specimen racks, e.g., three, four, five, six, seven, eight, nine, ten, or more specimen racks. Preferably, the apparatus is configured to house the same number of specimen racks, e.g., two, as microfluidic cartridges.

In some embodiments, each specimen rack 24a, 24b can include multiple holders 26. The holders 26 can include receptacles for holding diagnostic reagents, such as nucleic acid amplification reagents. The racks 24 may also include specimen tubes (not shown) and mixing tubes (not shown) for preparing diagnostic-ready samples, such as amplification-ready samples. The apparatus 10 may prepare the desired reagents in the racks 24a, 24b using the dispenser 400. Further description of various fluid dispensers may be found in e.g., U.S. Patent Application Publication 2009-0130719 and U.S. Patent Application Publication 2009-0155123, incorporated herein by reference in their entirety. The prepared fluids may then be transferred to a microfluidic cartridge and be inserted into heater/optical modules 500a, 500b for processing and analysis.

In some embodiments, the reaction chambers within the microfluidic cartridge(s) (discussed below) can include one or more reagents, buffers, etc., used in the assays described herein, e.g., amplification and/or detection. For example, in some embodiments, the reaction chambers of the microfluidic cartridge can include, e.g., amplification primers, probes, nucleotides, enzymes such as polymerase, or the like. By way of example, in some embodiments, the reaction chambers can include lyophilized reagents, to which processed biological sample (e.g., a solution of extracted nucleic acids) can be added.

FIG. 1A is a front plan view of the diagnostic apparatus 10 of certain of the embodiments. As shown in FIG. 1A, the diagnostic apparatus 10 can include a fluid dispenser 400, mounted on a lateral rail 20. The lateral rail 20 may be part of a motor-driven gantry 18, which may also include a fore-aft rail 22 (not shown). The fore-aft rail 22 may be connected to the lateral rail 20 and mounted perpendicularly to the lateral rail 20 in the diagnostic apparatus 10.

FIG. 1A further illustrates a cover 28 over the heater/optical modules 500a, 500b. Receiving trays 520a and 520b may be located beneath or within the housing of the heater/optical modules 500a, 500b. Receiving tray 520a is illustrated in an open position, making it available to receive a microfluidic cartridge 200. Receiving tray 520b is illustrated in a closed position. Closing the tray not only places the reagents in the appropriate position for processing, but also further protects the interior of the heater/optical modules from receiving unwanted or stray light. Introduction of stray or unwanted light into the detection area may cause erroneous fluorescent levels, e.g., that include fluorescence derived from light which is not emitted from the reaction chamber.

FIG. 1B is a perspective view of the diagnostic apparatus 10 showing certain of the internal components found in certain of the embodiments. To better illustrate certain features, the apparatus housing 30, the cover 16, and the heater/optical cover 28 found in FIG. 1A are not shown in FIG. 1B. Shown in FIG. 1B is the gantry 18, including the lateral rail 20 and fore-aft rail 22. The fluid dispenser 400 can be mounted on the lateral rail 20 and can slide laterally along the long lateral rail 20. The lateral rail 20 can be connected to the fore-aft rail 22 which itself may move in the fore-aft direction. In this manner the fluid dispenser 400 is available to move in the plane of the x and y axes throughout the diagnostic device 10. As described below, in some embodiments, the fluid dispenser 400 can also to move up and down in the z-plane on the lateral rail 20, thereby giving the dispenser 400 the ability to move in three directional degrees throughout the diagnostic device 10.

Also shown in FIG. 1B are heater/optical modules 500a, 500b. In FIG. 2B, the heater/optical modules are shown without cover 28. The receiving trays 520a and 520b are depicted in the open position and are each holding microfluidic cartridges 200. In some embodiments, the receiving trays can each include a heater substrate 600 (not shown) residing beneath and in thermal communication with, each of the microfluidic cartridges 200. The heater/optical modules 500a, 500b may also each include a detector head 700 (not shown) described in greater detail below.

As will be described in more detail below, the diagnostic apparatus 10 may be configured to conduct real-time analysis on one or more samples. The sample to be tested may first be placed in a specimen tube (not shown) on the rack 24a or 24b. Reagents such as amplification reagents, (e.g., amplification primers, buffers, nucleotides, and the like) and/or detection reagents (e.g., probes and the like) may be located in the holders 26 on the rack 24a inside the diagnostic apparatus 10. The fluid dispenser 400 may mix and prepare the sample for diagnostic testing and may then deliver the prepared sample to the microfluidic cartridge 200 for thermal cycling and target nucleic acid detection in the heater/optical modules 500a, 500b. Alternatively, the fluid dispenser 400 may deliver nucleic acid samples to the reaction chambers of the microfluidic cartridge, wherein the reaction chambers, e.g., amplification chambers or detection, of the microfluidic cartridge already contain reagents for an amplification reaction or detection. Certain details and methods for processing polynucleotides may be found in e.g., U.S. Patent Application Publication 2009-0131650, U.S. Patent Application Publication 2010-0009351, U.S. Patent Application Publication 2009-0134069, all of which are incorporated herein by reference in their entirety.

Figure 1C:
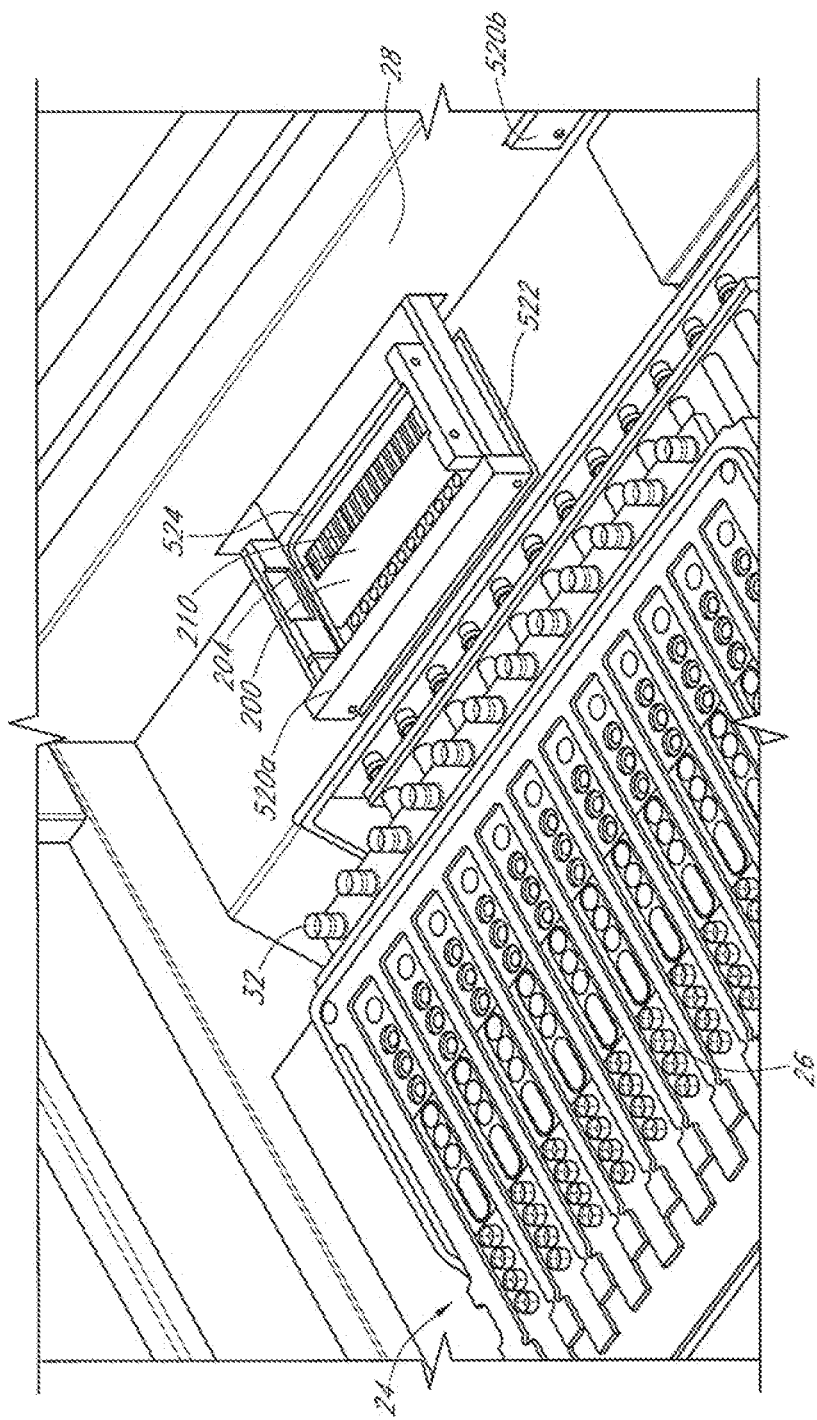
FIG. 1C illustrates an interior view of the diagnostic apparatus of FIGS. 1A and 1B.

FIG. 1C illustrates an interior view of the diagnostic apparatus 10, showing the rack 24a holding a number of sample tubes 32 and reagent holders 26. FIG. 1C also shows a cartridge 200 situated in the receiving tray 520a. The receiving tray 520a is in an open position extending from the heater/optical module 500a which has the cover 28 attached. The receiving tray 520b is in a closed position. Advantageously, in some embodiments the receiving trays 520a, 520b may allow easy placement of the microfluidic cartridge 200, by a user or by an auto-loading device. Such a design may also accommodate multiplexed pipetting of samples using the robotic fluid dispenser 400.

As illustrated in FIG. 1C, a recessed bay 524 can be a portion of the receiving tray 520 that is configured to selectively receive the microfluidic cartridge 200. The cartridge 200 may be aligned in the recessed bay 524 of the receiving tray 520 so that various components of the apparatus 10 that can operate on the microfluidic cartridge 200 (such as, heat sources, detectors, force members, and the like) are positioned to properly operate on the microfluidic cartridge 200 while the cartridge 200 is received in the recessed bay 524 of the receiving tray 520. For example, contact heat sources on the heater substrate 600 (not shown) may be positioned in the recessed bay 524 such that the heat sources can be in thermal communication with distinct locations on the microfluidic cartridge 200.

The cartridge 200 may include a label 204 attached to the top side of the cartridge 200. The label 204 may include a window portion 210 through which the detection chambers may be optically accessible by the detector head as discussed in further detail below, for the detection of target nucleic acids, e.g., target amplicons.

Microfluidic Cartridges

Figure 2:
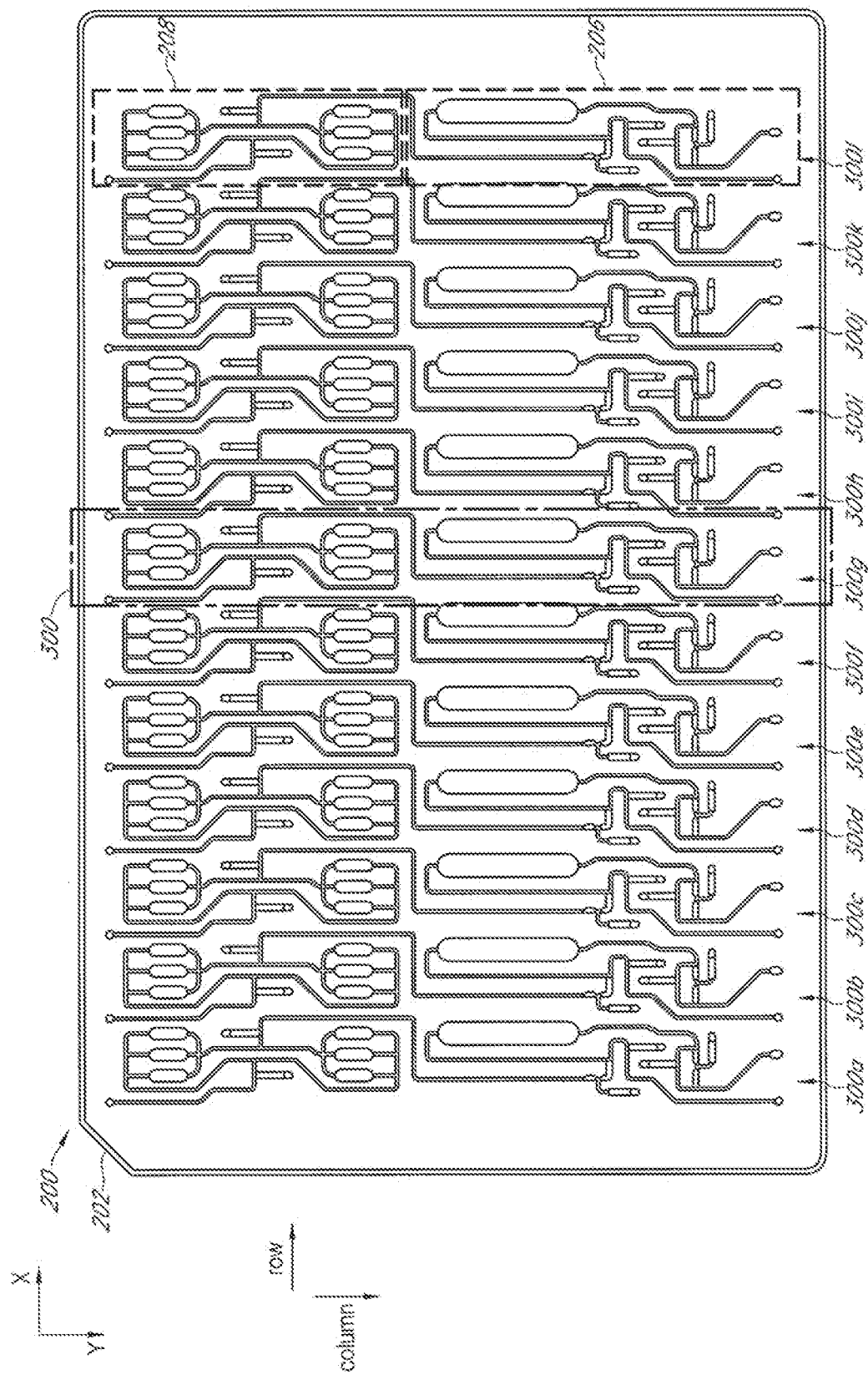
FIG. 2 is a top plan view of a microfluidic cartridge used in certain of the embodiments.

FIG. 2 is a top plan view of a microfluidic cartridge 200. Certain embodiments contemplate that one or more samples may be introduced into the microfluidic cartridge 200 to undergo analysis. The diagnostic analysis may include thermocycling of the sample to effectuate nucleotide amplification, such as by PCR, of one or more target polynucleotides from one or more samples and may include the detection of amplified target nucleic acids in the sample.

The term "cartridge," as used herein, refers to a unit that may be disposable, or reusable in whole or in part, and that can be configured to be used in conjunction with some other apparatus that has been suitably and complementarily configured to receive and operate on (such as deliver heat, light, and the like, to) the cartridge. By microfluidic, as used herein, is meant that volumes of sample, and/or reagent, and/or amplified polynucleotide are from about 0.001 µl to about 999 µl, such as from 1-100 µl, or from 2-25 µl, as defined above. Similarly, as applied to a cartridge, the term microfluidic means that various components and channels of the cartridge, as further described herein, are configured to accept, and/or retain, and/or facilitate passage of microfluidic volumes of sample, reagent, or amplified polynucleotide. Certain embodiments herein can also function with nanoliter volumes (in the range of 10-500 nanoliters, such as 100 nanoliters).

The cartridge 200 may comprise a plurality of sample lanes. The microfluidic cartridge 200 shown in FIG. 2 includes twelve independent sample lanes 300a-l. However, the skilled artisan will appreciate that the cartridge shown in FIG. 2 is exemplary, and that the present embodiments encompass cartridges that have 1, 2, 3, 4, 5, 6, 7, 8, 9, 10, 11, 12, 13, 14, 15, 16, 17, 18, 19, 20, 21, 22, 23, 24, or more, sample lanes. The microfluidic cartridge 200 may can be configured so that sample analyses can be carried out in two or more of the sample lanes in parallel, for example simultaneously, and wherein each sample lane 300a-l may be independently associated with a given sample. The samples to be analyzed in each sample lane 300a-l may be the same as, or different, from one another. Each sample lane 300a-l can be configured to carry out amplification on a sample in which the presence or absence of one or more target polynucleotides can be determined.

As described in more detail below with relation to FIG. 3, each sample lane 300a-l may include a microfluidic network having an inlet, microfluidic valves, microfluidic gates, channels, and reaction chambers, such as one or more amplification chambers, and a plurality of detection chambers. Each sample lane 300a-l can be conceptually divided into a first stage 206 and a second stage 208. The microfluidic cartridge 200 may include a registration member 202, for example, a cutout, which corresponds to a complementary edge 526 in the recessed bay 524 of the receiving tray 520a, 520b of the heater/optical modules 500a, 500b. The pairing of the registration member 202 of the microfluidic cartridge 200 and the complementary edge 526 of the recessed bay 524 allows for secure and correct placement and orientation of the microfluidic cartridge 200 in the receiving tray 520a, 520b.

A microfluidic cartridge 200 may be constructed from a number of layers. Accordingly, one aspect of the present embodiments relates to a microfluidic cartridge that comprises a first, second, third, fourth, and fifth layers wherein one or more layers define a plurality of microfluidic networks, each network having various components configured to carry out amplification and detection on a sample in which the presence or absence of one or more polynucleotides is to be determined. In another embodiment, the microfluidic cartridge 200 can comprise a plurality of lanes, each including a reaction chamber, etched or molded in a single plane, such as in a molded plastic substrate, with each lane being closed by a cover layer, such as an adhesive plastic film layer. Embodiments with 1, 2, 4, 6, 8, 10, 12, 14, 16, 18, 20, 22, 24, 28, 30, or more lanes per cartridge are contemplated. For example, one suitable design is a single cartridge 200 having 12 sample lanes, each lane having an amplification chamber and six detection chambers.

In understanding the relative orientation of the cartridge 200, a sample lane 300 can be considered a column on the cartridge 200, running along a y-axis and multiple lanes 300a-l can be aligned side by side, in the direction of an x-axis. In certain embodiments disclosed herein, the x and y axes designated for the cartridge 200 may correspond to the x and y axes designated for the diagnostic apparatus 10 in FIGS. 1A-C, such that a relative spatial orientation of the cartridge 200 when it is positioned in the diagnostic apparatus 10 is understood.

Figure 3:
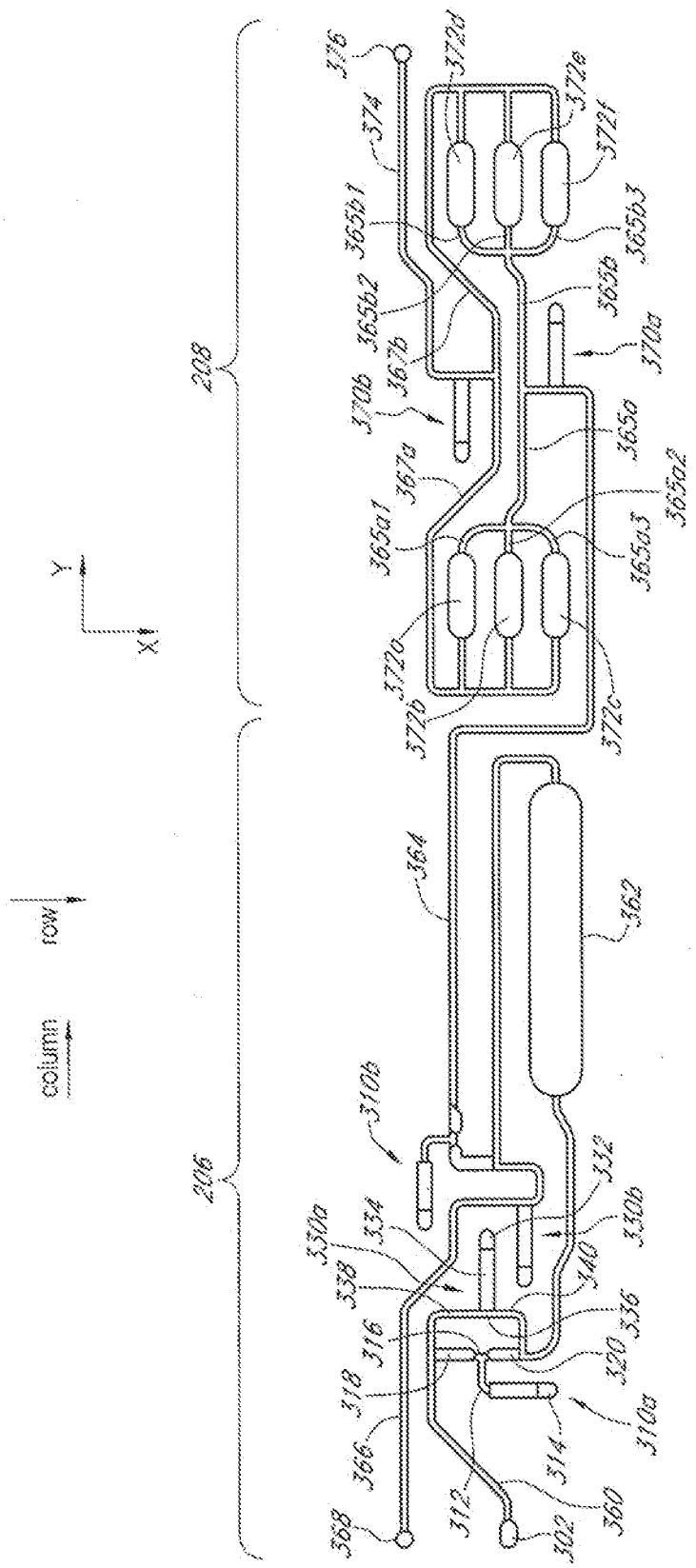
FIG. 3 shows a single sample lane used in certain of the embodiments, the sample lane being part of the microfluidic network of the microfluidic cartridge of FIG. 2.

FIG. 3 shows a single sample lane 300 in a microfluidic cartridge, e.g., microfluidic cartridge 200, shown in FIG. 2. The sample lane 300 comprises a microfluidic network, the microfluidic network including an inlet 302, microfluidic valves 330a, 330b, 370a, and 370b, microfluidic gates 310a and 310b, microfluidic channels 360, 364, 366, and 374, an amplification chamber 362, and six detection chambers 372a-f.

The spatial arrangement of the sample lane shown in FIG. 3 can be maintained, such that the sample lane 300 constitutes a column along the y-axis. In this manner, the sample lane 300 can be comprised of three columns of detection chambers (a first column of detection chambers 372a and 372d; a second column of detection chambers 372b and 372e; and a third column of detection chambers 372c and 372f). Likewise, the sample lane 300 can be comprised of two rows of detection chambers (a bottom row of detection chambers 372a-372c and a top row of detection chambers 372d-372f). Accordingly, in the embodiment shown in FIG. 3, there are six detection chambers within the sample lane 300. The skilled artisan will appreciate, however, that the sample lane shown in FIG. 3 is exemplary, and that the embodiments disclosed herein can have fewer, or more, detection chambers within a sample lane, e.g., 2, 4, 6, 8, 10, 12, 14, 16, or more.

In the microfluidic network of the sample lane 300, the inlet 302 is the point at which a sample is input by the fluid dispenser 400 into the microfluidic network. The various components of the microfluidic network are spatially arranged in the sample lane 300 such that the inlet 302 can be considered the most upstream portion of the microfluidic network, meaning that in the progression of fluidic movement throughout the microfluidic network, all other components can be downstream of the inlet 302. The vent 368 and 376 are the most downstream components of the microfluidic network, meaning that in the progression of fluidic movement throughout the microfluidic network of the sample lane 300, the vents 368 and 376 are the components in the microfluidic network that are reached last as the fluid travels in the varying paths of the microfluidic network.

The inlet 302 can be manufactured to be frustoconical in shape with an appropriate conical angle so that industry-standard pipette tips (e.g., 2 µl, 10 µl, 20 µl, 200 µl, volumes, etc.) fit snugly, entering from the widest point of the inlet. Thus, in certain embodiments, an inlet comprises an inverted frustoconical structure of at least 1 mm height, and having a diameter at its widest point that accepts entry of a pipette tip, of from 1-5 mm. The apparatus herein may be adapted to suit other, later-arising, industry standards for pipette tips not otherwise described herein. Typically the volume of sample accepted via an inlet into a microfluidic network in a sample lane is from 0.1-20 µl, e.g., 5-10 µl. The fluid dispenser 400 can used to appropriately place the pipette tip in the inlet 302 of the sample lane 300. The inlet hole can be designed to fit a pipette tip snugly and to create a good seal around the pipette tip, within the cone of the inlet hole. Once the pipette tip lands within the cone, the conical shape guides the pipette and mechanically seals the combination to provide error free dispensing or withdrawal of fluid into the cartridge 200. However, the cone is designed such that the sealing is reversible to avoid pulling the cartridge 200 away from the recessed bay 524 in the receiving tray 520, when the pipette tips are lifted after completion of the dispensing operations.

As part of the first stage 206, the microfluidic network extends downstream from the inlet 302 along the first channel 360. The first channel 360 extends past, and is in fluid communication with, the amplification gate 310a and the amplification valve 330a. Downstream of the amplification gate 310a and the amplification valve 330a, the first channel can extend to, and be in fluid communication with, the amplification chamber 362. The second channel 364, which can be in fluid communication with the amplification chamber 362, can extend from the amplification chamber 362 through the second amplification gate 310b and through the first detection valve 370a, in the second stage 208 of the sample lane 300. In this manner, the second channel 364 extends from the first stage 206 of the microfluidic network of the sample lane 300 to the second stage 208. In the first stage 206, the third channel 366 is in fluid communication with the second channel 364 and can extend downstream from the second channel 364 at a point upstream of the second amplification gate 310b. The third channel 366 can be in fluid communication with the second amplification valve 330b and can extend from the second channel 364 to the first vent 368, and can be in fluid communication with the first vent 368.

In the second stage 208 of the microfluidic network, the second channel 364 can extend downstream through, and be in fluid communication with, the first detection valve 370a. Extending past the first detection valve 370a, the second channel 364 can split into two subchannels 365a and 365b, both of which are in fluid communication with the second channel 364. The subchannels 365a, 365b can each split again into additional subchannels 365a1-3 and 365b1-3, respectively. Subchannels 365a1-3 can extend through, and can be in fluid communication with, the detection chambers 372a-c, respectively. Likewise, subchannels 365b1-3 can extend through, and be in fluid communication with, the detection chambers 372d-f. Extending from detection chambers 372a-c, subchannels 365a1-3 can connect together again downstream of the detection chambers 372a-c as subchannel 367a. Extending from detection chambers 372d-f, subchannels 365b1-3 can connect together again downstream of the detection chambers 372d-f as subchannel 367b. Further downstream, subchannels 367a and 367b can connect together to form a fourth channel 374, which can extend to, and be in fluid communication with, the second vent 376. Along the fourth channel 374, upstream of the second vent 376, can be positioned a second detection valve 370b in fluid communication with the fourth channel 374. The vents 368 and 376 may be configured to drain excess sample from the microfluidic network and prevent a user from introducing any excess amount of liquid into the microfluidic cartridge 200.

The amplification chamber 362 can have a volume of about 5-10 µl, and particular embodiments of the amplification chamber 362 have a volume of about 8 µl. For amplification chambers of about 8 µl, the input volume of the sample can be approximately 10 µl. Sample input volumes may be greater than the volume of the amplification chamber 362 in order to account for sample volumes located in the channels and detection chambers 372a-f. Excess volume may also be drained from the microfluidic network through the vents 368 and 376.

In certain embodiments, the detection chambers 372a-f can each have a volume of about 1 µl. In some embodiments, the detection chambers 372a-f are of a volume equal to each other. In some embodiments, the detection chambers 372a-f may be of varying volumes. The detection chambers 372a-f may individually be of a volume less than the volume of the amplification chamber 362. In some embodiments, the detection chambers 372a-f may collectively be of a volume less than the volume of the amplification chamber 362.

In some embodiments, the inside walls of the channels in the amplification chamber 362 and detection chambers 372a-f can be made very smooth and polished to a shiny finish (for example, using a polish such as SPI A1, SPI A2, SPI A3, SPI B1, or SPI B2) during manufacture. The amplification chamber 362 and detection chambers 372a-f may be polished in order to minimize any microscopic air trapping in the surface of the chambers, which may cause bubbling during thermocycling. The presence of bubbles, particularly in the detection chambers 372a-f might cause a false reading. Furthermore, the amplification 362 and detection chambers 372a-f can be made shallow such that the temperature gradient across the depths of the chambers is minimized.

Figure 4A:
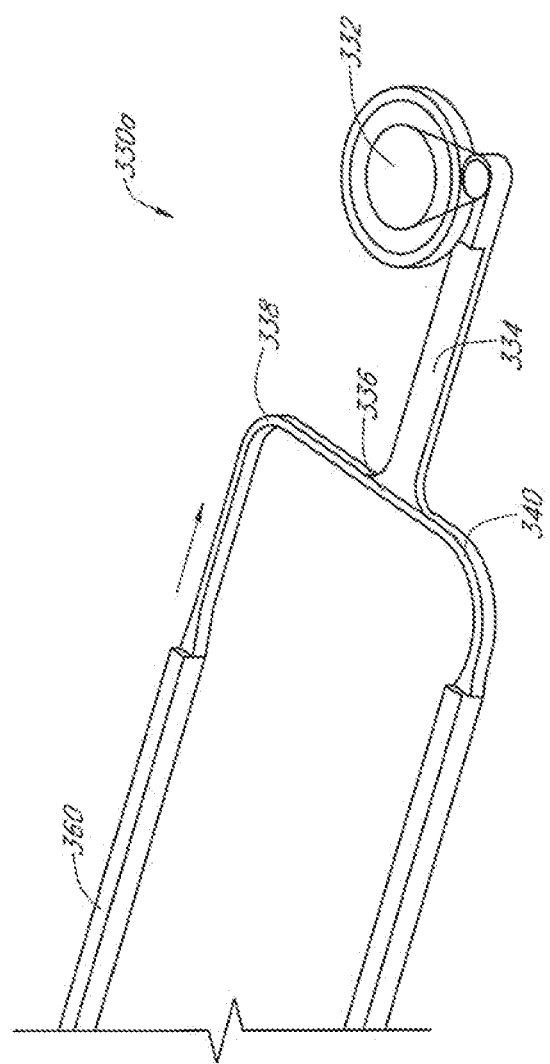
FIG. 4A is a representation of a valve used in certain of the embodiments of the microfluidic network of FIG. 3.

Turning now to FIG. 4A, FIG. 4A is a representation of an exemplary amplification valve, e.g., the first amplification valve 330a, shown in the microfluidic network of FIG. 3. A valve is a component of the microfluidic network that can be set in an initial open state, and thus, when open, allowing a sample containing polynucleotides to pass along a channel from a position on one side of the valve (e.g., upstream of the valve) to a position on the other side of the valve (e.g., downstream of the valve). It is noted that the other valves in the microfluidic network (such as, the second amplification valve 330b and the first and second detection valves 370a and 370b) can be provided with the same structure and can operate in a manner similar to the first amplification valve 330a, as described herein.

As shown in FIG. 4A, the valve 330a can include a valve loading port 332, a valve loading channel 334, and a valve junction 336. The valve junction 336 is the point where the valve loading channel 334 of the first amplification valve 330a intersects the first channel 360. Sections of the first channel 360 shown in FIG. 4A are, in spatial relation to the first amplification valve 330a, an upstream side 338 of the first channel 360 and a downstream side 340 of the first channel 360.

Figure 4C:
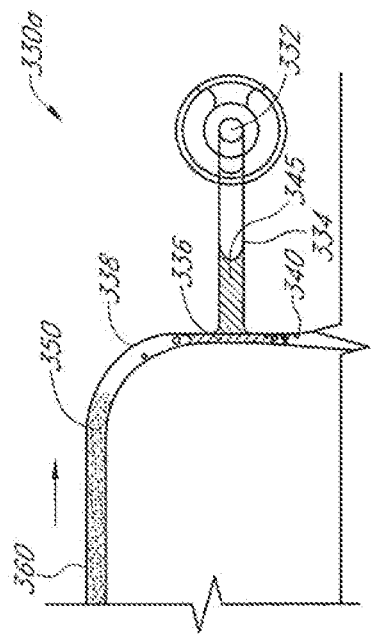
FIG. 4C shows the valve of FIG. 4A in a closed state.
Figure 4B:
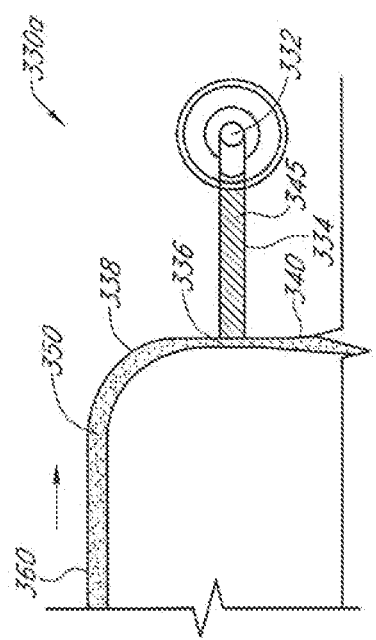
FIG. 4B shows the valve of FIG. 4A in an open state.

As shown in FIGS. 4B and 4C, the valve 330a may include one or more masses of a thermally responsive substance (TRS) 345 that is substantially immobile in the valve loading channel 334 at a first temperature and more mobile at a second temperature. A mass of TRS can be an essentially solid mass or an agglomeration of smaller particles that cooperate to obstruct the passage upon actuation. Examples of TRS's 345 include a eutectic alloy (e.g., a solder), wax (e.g., an olefin), polymers, plastics, and combinations thereof.

The TRS 345 can be deposited into the loading port 332 machined in the microfluidic substrate of the microfluidic cartridge 200. The loading port 332 of the microfluidic cartridge 200 can be dimensioned in such a way that a droplet of TRS can be accurately propelled to the bottom of the loading port 332 using, for example, compressed air. The microfluidic cartridge 200 can be maintained at a temperature above the melting point of the TRS thereby permitting the TRS to stay in a molten state immediately after it is dispensed. After the drop falls to the bottom of the loading port 332, the molten TRS 345 is drawn into the valve loading channel 334 by capillary action. The amount of TRS 345 that is dispensed into the loading port 332 can be approximately equal to the volume of the valve loading channel 334. The valve loading channel 334 can be structured so that even though the TRS 345 dispensed into the loading port 332 may vary between a minimum and a maximum dispensed amount, the TRS always fills up to, and stops at, the valve junction 336 because the junction 336 provides a higher cross section than that of the loading channel 334 and thus reduces the capillary forces. When the microfluidic cartridge 200 is cooled to a first temperature, the mass of immobile TRS is situated in the valve loading channel 334, not blocking the first channel 360 at the valve junction 336.

FIG. 4B shows the first amplification valve 330a in the initial open state, which permits the sample 350 to travel through the first channel 360 from the upstream side 338 of the valve 330a to the downstream side 340 of the valve 330a. Upon actuation, e.g., by application of heat to the first amplification valve 330a, the valve 330a can transition from an open state to a closed state.

FIG. 4C shows the first amplification valve 330a in a closed state, such that upon heating, at least a portion of the TRS 345 has moved from the loading channel 334 into the valve junction 336. The valve 330a operates by heating the TRS and air trapped in the loading port 332. The expansion of the heated air in the loading port 332 forces the mobile TRS 345 forward in a manner so that it moves into the valve junction 336. As the TRS 345 once again cools and solidifies it becomes immobile again and can thereby block the passage of the sample 350 in the first channel 360, preventing that portion of the sample 350 from traveling from the upstream side 338 of the valve 330a to the downstream side 340 of the valve 330a.

Figure 5:
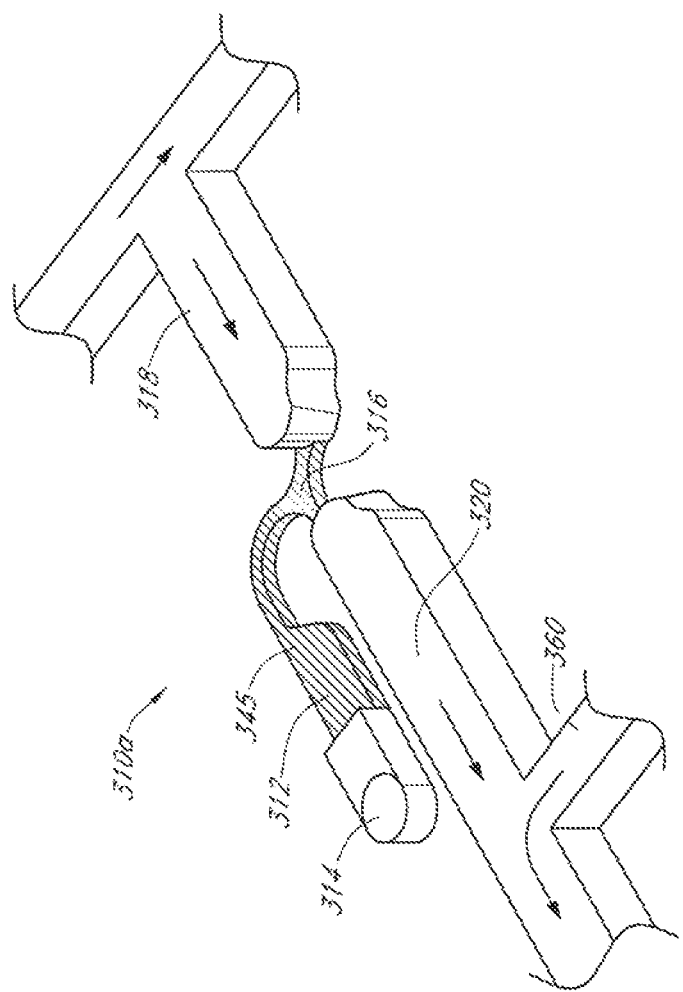
FIG. 5 is a representation of a gate used in certain embodiments of the microfluidic network of FIG. 3.

FIG. 5 is a representation of an exemplary amplification gate, e.g., the first amplification gate 310a, shown in the microfluidic network of FIG. 3. A gate is a component of a microfluidic network that, unlike a valve, can be set in an initially closed state, meaning that the gate can initially act to prevent a sample from passing to the downstream portion of the channel with which the gate is in fluid communication. Upon opening, the amplification gate 310a can then allow the passage of the sample to the downstream portion of the channel. It is noted that the second gate 310b of the microfluidic network can be provided with the same structure and can operate in a manner similar to the first amplification gate 310a, as described herein.

As shown in FIG. 5, the gate 310a can be comprised of a loading port 314, a gate loading channel 312, and a gate junction 316. The gate junction 316 is the point where the gate loading channel 312 of the first amplification gate 310a intersects with the first channel 360. Shown in FIG. 5 are the upstream portion 318 and the downstream portion 320 of the first channel 360.

A mass of TRS 345 can be deposited into the loading port 314 and passed into the gate loading channel 312. The loading port 314 and the gate loading channel 312 can be dimensioned in such a way that the deposited TRS 345 does not become immobilized in the gate loading channel 312, but extends into the gate junction 316. In some embodiments, the gate junction 316 can be narrower (e.g., approximately 150 μm wide and 100 μm deep) than the upstream 318 and downstream 320 portions of the first channel 360 with which it is in fluid communication. An upstream side 318 as well as a downstream side 320 of the gate junction 316 can be made wide (e.g., approximately 500 μm) and deep (e.g., approximately 500 μm) to help ensure the wax stops at the gate junction 316.

During operation of the diagnostic apparatus 10, a heater may be positioned external to the cartridge 200 and may be in thermal communication with the gate 310a. At the required time during operation of the diagnostic apparatus, the external heater may be used to melt the TRS 345 in gate 310a. The melted TRS 345 may be pushed downstream by upstream fluidic pressure and may move downstream along with the sample 350. The amount of TRS 345 melted and moved out of the gate junction 316 may be minimized for optimal gate 310 opening.

In various embodiments, the gate 310a can be configured to minimize the effective area or footprint of the gate within the network, such as by being bent as shown in FIG. 3 and FIG. 5. Minimizing the effective area or footprint of the gate within the network can increase the density of a given microfluidic network and can thereby reduce the cost per part, provide for a more compact network, and minimize network channel length or volume.

Fluid Dispensers

Figure 6:
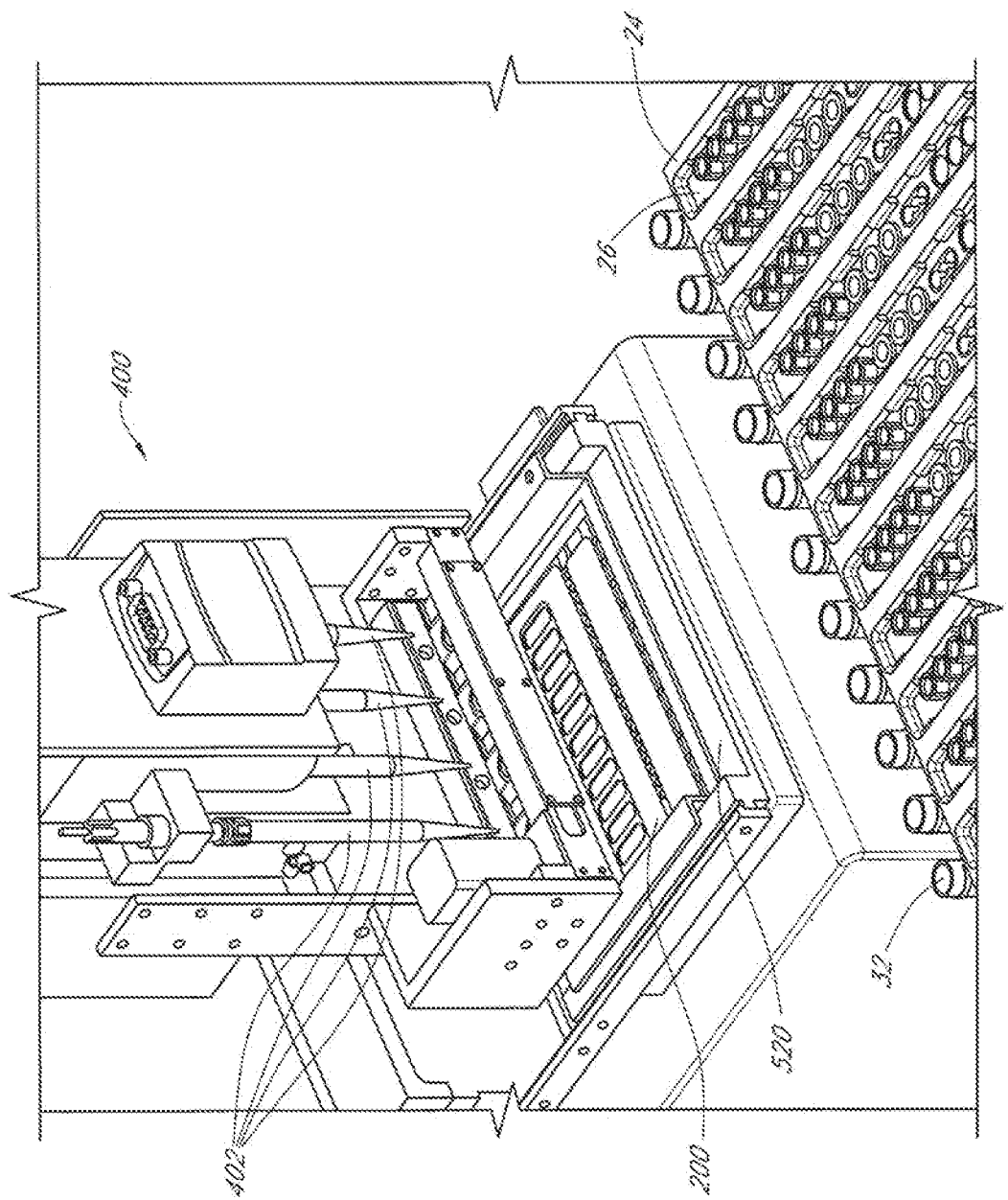
FIG. 6 shows an interior view of the diagnostic apparatus with the fluid dispenser positioned over the cartridge.

As mentioned above, the devices disclosed herein can include fluid dispensers. Turning to FIG. 6, shown is an interior view of the diagnostic apparatus 10 with the fluid dispenser 400 positioned over the cartridge 200. The microfluidic cartridge 200 is configured to receive sample(s) via the one or more inlets 302, delivered by a fluid dispenser 400. A liquid dispenser 400 for use with the diagnostic apparatus 10 herein is described in U.S. patent application Ser. No. 12/212,403, filed Sep. 17, 2008, and incorporated herein by reference in its entirety.

In various embodiments, preparation of an amplification-ready sample in the diagnostic apparatus 10 can include one or more of the following steps: contacting a polynucleotide sample from the sample tube 32 with an amplification reagent mixture in one or more of the containers in the holder 26, the reagent mixture comprising a polymerase enzyme and a plurality of nucleotides (in some embodiments, the amplification reagent mixture can further include a positive control polynucleotide and a fluorogenic hybridization probe selective for at least a portion of the portion); in some embodiments, the amplification reagent mixture can be in the form of one or more lyophilized pellets, as stored in a receptacle on a holder, and the method can further include reconstituting the pellet with liquid to create an amplification reagent mixture solution. Various, such as one or more, of the liquid transfer operations associated with the foregoing steps can be accomplished by the automated fluid dispenser 400, having multiple pipette tips 402, under control of a microprocessor (not shown). As discussed below, in some embodiments, reagents, buffers, etc. used in the preparation of an amplification-ready sample are disposed within the microfluidic cartridge itself, e.g., within the amplification chamber. The dispenser can introduce the sample into the microfluidic network, where the sample is mixed with reagents, etc., within the network.

The fluid dispenser 400 can be configured to dispense a solution (e.g., of a prepared sample, amplification reagents, and probes, etc.) into the microfluidic cartridge 200. The fluid dispenser 400 can be configured to travel from a first set of positions above the rack 24 and holders 26 having various containers that hold reagents, etc., to a second set of positions above the cartridge 200, where pipette tips 402 can be inserted into the inlets 302 of the microfluidic cartridge 200. The cartridge 200 can be positioned in the receiving tray 520. The second set of positions is depicted schematically in FIG. 6. The fluid dispenser 400 can travel between the first set of positions and the second set of positions by motion in two orthogonal directions in a horizontal plane along the lateral rail 20 (x-axis, of FIG. 1B) and fore-aft rail 22 (y-axis) of the gantry 18 and in a vertical direction (z-axis) to reach the holders 26 and the cartridge 200. Multiple, e.g., 4, pipette tips 402 can dispense fluid into inlets 302 of the microfluidic cartridge 200.

In some embodiments, the fluid dispenser 400 can be configured to accept or dispense, in a single operation, an amount of 1.0 ml of fluid or less, such as an amount of fluid in the range 10 nl-1 ml. Specifically, the fluid dispenser 400 can accept and dispense, in a single operation, an amount of about 5-15 μl of the sample. When transferring a sample containing extracted nucleic acid from a pipette tip 402 to an inlet 302 on the microfluidic cartridge 200, for example, using the fluid dispenser 400, a volume of air or other gas can also be introduced into the microfluidic network of the sample lanes 300 to provide propulsion or downstream movement to the sample. The volume of air or gas introduced into the microfluidic network can be between about 0.5 ml and about 5 ml, but depending on the volume of the pipette tip 402 and the volume of air or gas required for movement of the sample within the microfluidic network.

Heater/Optical Modules

Figure 7A:
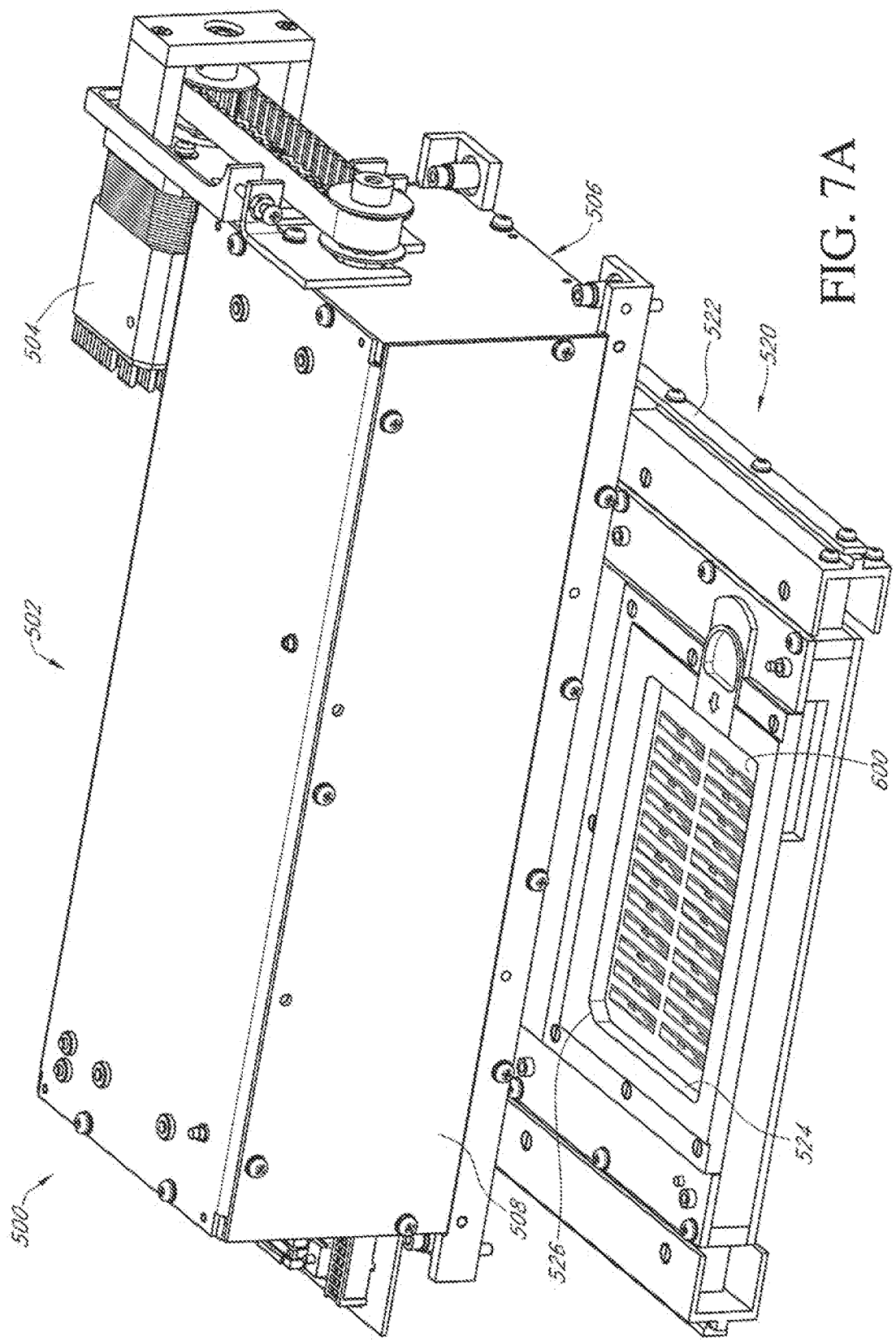
FIG. 7A illustrates an exterior view of the heater/optical module.
Figure 7B:
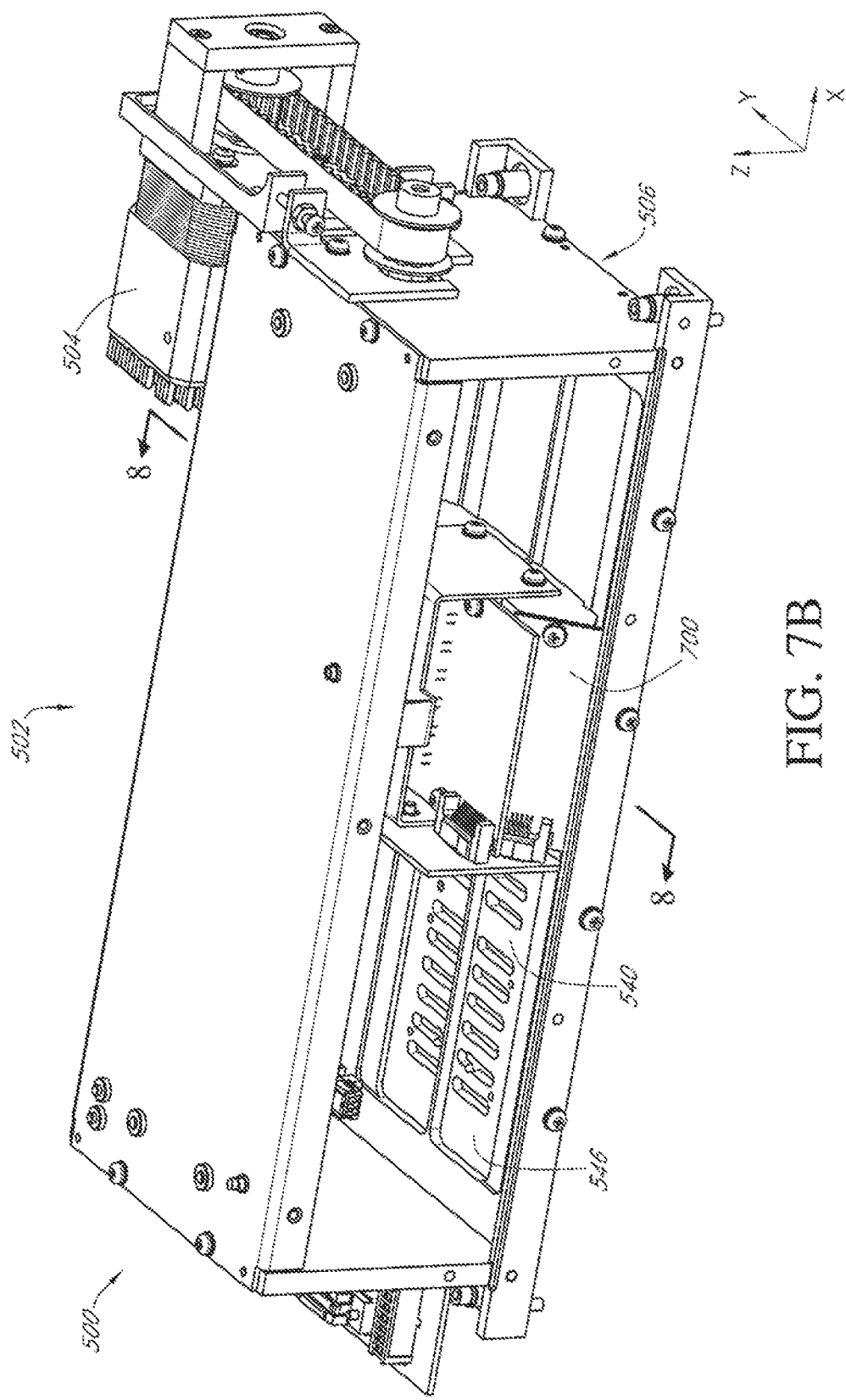
FIG. 7B illustrates an isometric view of the optical unit of the heater/optical module of FIG. 7A, the optical unit having the side cover removed.
Figure 7C:
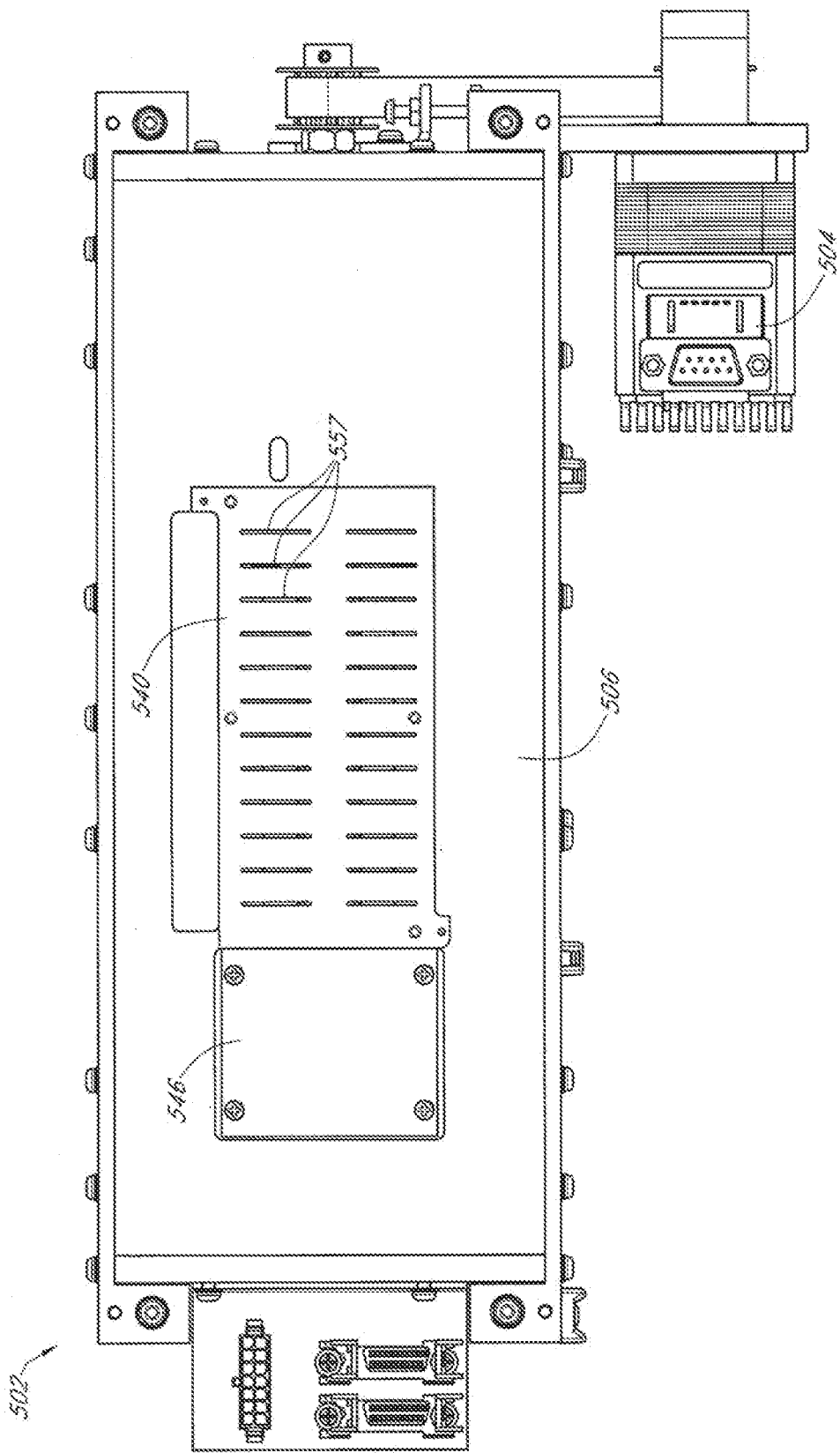
FIG. 7C illustrates a bottom view of the optical module of FIG. 7A.

FIGS. 7A-C illustrate the heater/optical module 500 of the detection apparatus 10 found in certain embodiments. The heater/optical module 500 may comprise an optical unit 502 and a receiving tray 520 or a portion of the receiving tray. FIG. 7A shows one embodiment of the enclosed optical unit 502 having a motor 504 externally attached thereto for driving movement of a detector head 700. The detector head 700 may be housed inside the optical module 502. FIG. 7A illustrates the empty receiving tray 520 coupled to a bottom side 506 of the optical unit 502. The receiving tray 520 and the optical unit 502 together comprise the heater/optical module 500. The receiving tray 520 may receive a cartridge 200 in a recessed bay 524, the cartridge 200 itself receiving samples upon which amplification and detection can be performed. For example, the recessed bay 524 can have an edge 526 which is complementary in shape to the registration member 202 on the microfluidic cartridge 200 so that the microfluidic cartridge 200 is selectively received in, e.g., a single orientation. The registration member 202 can be, for example, a cut-out on an edge of the cartridge 200 or one or more notches that are made on one or more of the sides. By selectively receiving the cartridge 200, the recessed bay 524 can help a user to position the cartridge 200 so that the optical module 502 can properly operate on the cartridge 200. In this way, error-free alignment of the cartridges 200 can be achieved.

After receiving the samples, the receiving tray 520 may be moved (e.g., mechanically or manually) on rails 522 to a position underneath the optical unit 502. In some embodiments, the receiving tray 520 may comprise an auto-loading device, which automatically aligns the cartridge once positioned beneath the optical module 502. In some embodiments, the recessed bay 524 of the receiving tray 520 may contain a heater substrate 600 which can be in thermal or physical communication with the cartridge 200 to activate certain cartridge components and conduct the thermal cycling necessary for nucleotide amplification and detection. In some embodiments, the receiving tray 520 may subsequently be raised to place the cartridge 200 in thermal and/or physical contact with the optical unit 502, such as in contact with an aperture plate 540 on the bottom side 506 of the optical unit 502.

FIG. 7B illustrates an embodiment of the optical unit 502 with a front panel 508 removed to show the interior of the optical unit 502. Shown in FIG. 7B is the detector head 700. As described in detail below, movement of the detector head 700 may be driven by the motor 504 to move laterally across the interior of the optical unit 502 to provide optical scanning and detection on the cartridge 200 when the cartridge 200 is positioned below the optical module 502 in the receiving tray 520. Shown in FIG. 7B is an aperture plate 540, positioned at the bottom side 506 of the optical unit 502.

FIG. 7C provides a bottom plan view of the optical unit 502. Shown in FIG. 7C is the aperture plate 540 and a normalizer plate 546 attached to the bottom side 506 of the optical module 502. The normalizer plate 546 may be used to calibrate the light source-photodetector pairs of the detector head 700. The normalizer plate 546 preferably comprises one or more components having known, standardized optical characteristics, and is configured to calibrate, standardize, and/or confirm proper operation of the detector head 700 and associated detector pairs and optical unit 502 circuitry. In some embodiments, prior to the start of the detection process, the detector head 700 can be positioned over the normalizer plate 546 and calibrated using the known properties of the normalizer plate 546. The specific light sources in the detector head 700 can be activated to shine light on corresponding portions of the normalizer plate 546. The light can be reflected back from the normalizer plate 546 to the detector (e.g. photodiode) associated with the light source of the detector pair. The light transmission received by the light detector can be recorded and compared with the known value of the optical characteristics of the normalizer plate 546. If the recorded values and known values do not correlate, corrective action may be taken, such as including an offset in the measurements or notifying the user of the error. In some embodiments, the normalizer plate 546 may be made of optically-transparent material such as polycarbonate mixed with a highly fluorescent dye, or other standardized chromophore or fluorophore. In one embodiment, the normalizer plate includes a standardized chromophore or fluorophore for each channel or color for detection by the detector head 700.

As shown in FIG. 7C, the aperture plate 540 contains apertures 557. The dimensions of apertures 557 are such that the detector's light sources and photodetectors may have access to (optically excite or view) the contents in the cartridge 200's detection chambers when the detector is moved to a plurality of positions within optical unit 502. For example, when a light source-photodetector pair of the detector 700 is located in a position over a particular aperture 557, light may travel from the light source and reach the detection chamber in the cartridge 200 through the aperture 557. The fluorescing reagents in the detection chamber may then be visible to the photodetector via the aperture 557.

Figure 8:
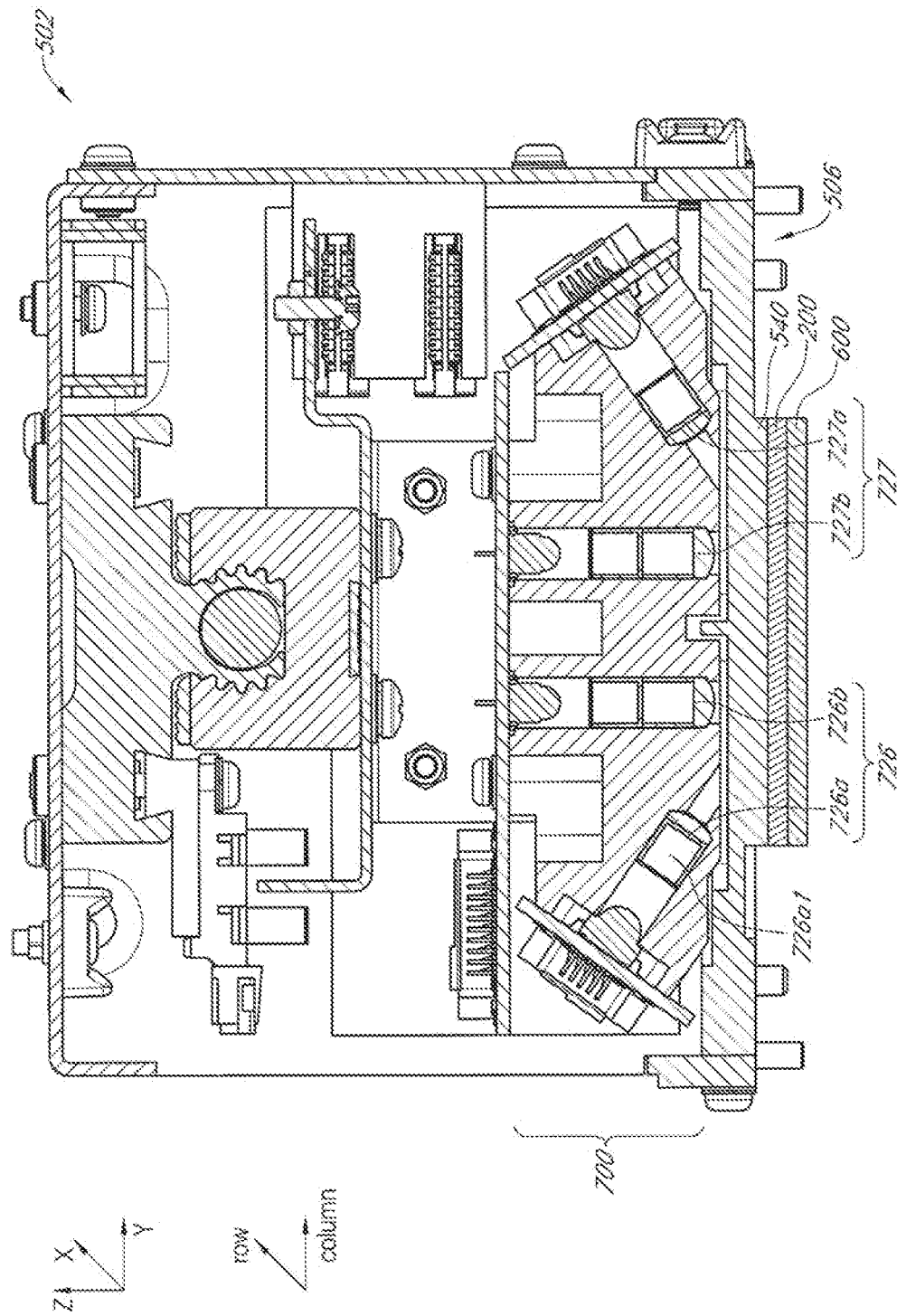
FIG. 8 illustrates a cross-sectional view of the detector head used within the optical unit, the cross-sectional view taken along line 8 of FIG. 7B.

FIG. 8 illustrates a cross-section of the detector head 700 taken along line 8 of FIG. 7B. The detector head 700 may be configured to optically excite and/or monitor fluorescence emitted in connection with detection of target polynucleotides present in the reaction chambers in the cartridge 200, such as the amplification chambers 362 and/or detection chambers 372a-f. Note that a positive result (presence of a target amplicon) may be indicated by increased fluorescence or decreased fluorescence, depending on assay design. For example, when the assay involves a fluorophore and a quencher, the quencher may quench fluorescence when the target is present, or in other assay designs, when the target is absent.

The device may comprise a plurality of detector pairs, e.g., 2, 3, 4, 5, 6, 7, 8, 9, 10, 11, 12, 13, 14, 15, 16, 17, 18, 19, 20, 21, 22, 23, 24, or more, such as the light source-photodetector pair 726. Each detector pair 726 can be comprised of a light source 726a, such as a light-emitting diode (LED), and a corresponding light detector 726b, such as a photodiode. The light source 726a may selectively emit light in an absorption band of a fluorescent moiety, and the light detector 726b may selectively detect light in an emission band of a fluorescent moiety.

In certain embodiments the light source 726a may comprise a bandpass-filtered diode that selectively emits light in the absorption band of the fluorescent probe. Light detector 726b may comprise a bandpass filtered photodiode that selectively detects light in the emission band of the fluorescent probe. In certain embodiments, a filter 726a1, such as a bandpass filter may be applied to the light source 726a's light. The light from the light source 726a passes through a filter before passing through the sample in the reaction chambers. In certain embodiments, the optical path-length for the light from the reaction chamber to the light detector 726b may be very small. The incident light from light source 726a generates fluorescence in the reaction chambers. Light from the reaction chamber then travels to the light detector 726b. Certain embodiments seek to mitigate any undesired light from entering the detector and thereby adversely affecting the light signal from the reaction chamber.

For the sake of explanation, a collection of cartridges or detector pairs along the length (x-axis) of the cartridge are referred to as a "row" and those along the width (y-axis) are referred to as a "column." In some embodiments, two or more detector pairs, for example detector pairs 726 and 727 in FIG. 8, may be arranged side by side collinearly in the detector head 700 as a column. In some embodiments, each one of the plurality of detector pairs, or a column of detector pairs, may be arranged along the length of the detector head 700 in rows. For example, behind the detector pairs 726 and 727 illustrated in FIG. 8 may be another column of detector pairs arranged in a similar or the same orientation. Certain embodiments contemplate six or more columns of such detector pairs, having two or more detector pairs in each column. For example, in some embodiments, there would be 12 detector pairs in total (two rows and six columns) with two detector pairs per column, permitting simultaneous detection of samples within 12 separate detection chambers.

Each light source, such as, for example, light source 726a, may be configured to produce light of a wavelength specific to a specific fluorescent moiety contained in a reaction chamber, e.g. a detection chamber. Each light detector, such as for example 726b, may be configured to detect the light emitted from the fluorescent moieties associated with the light produced by the light emitter in the detector pair. The detector pairs may be configured to independently detect a plurality of fluorescent moieties having different fluorescent emission spectra, wherein in each reaction chamber (e.g., detection chamber), emission from each fluorescent moiety can be tracked and correlated to the presence or absence of one particular target polynucleotide. Although folded light paths can be used, one embodiment utilizes a detector and emitter pair where each is in direct optical contact with the reaction (detection) chamber, preferably simultaneously in such contact. Optionally, the photodetector and light source of a detector pair are aligned with the reaction chamber along lines that substantially intersect at an acute angle at the reaction chamber. The angle can be, for example, between about 5 and 70 degrees, preferably between about 8 and 60 degrees, more preferably between about 10 and 50 degrees.

FIG. 8 also illustrates the plating arrangement found in certain embodiments of the diagnostic apparatus 10's heater optical/module 500 and the associated receiving tray 520 and heater substrate 600 of the cartridge 200. When the cartridge 200 is brought within proximity of the aperture layer 540 of the optical module 502, the heater substrate 600, the cartridge 200, and aperture layer 540 may be situated as depicted in the embodiment of FIG. 8. For simplicity sake, not shown in FIG. 8 is the receiving tray 520, in which the heater substrate 600 may be housed. As discussed above, the cartridge 200 may comprise a plurality of reaction chambers, which may be located so as to be thermally controlled separately from one another, or in groups. As discussed above, the heater substrate 600 may comprise a plurality of heaters. The aperture plate 540 may provide pressure to the cartridge 200 as a force member (not shown) pushes the receiving tray 520 upwards, in order to facilitate heating and cooling by heater substrate 600.

In certain embodiments, the receiving tray 520 places the cartridge 200 in proximity to the heater substrate 600 or aperture layer 540, but does not mechanically couple and/or thereby place the layers in contact with one another. In this manner, the cartridge 200 may be thermally, but not mechanically, coupled to the heater substrate 600. In other embodiments, the receiving tray 520 places the heater substrate 600 in both mechanical and thermal contact with the cartridge 200 and the cartridge 200 in mechanical contact with the aperture layer 540. In various embodiments, the apparatus may include one or more force members (not shown) that are configured to apply pressure to the receiving tray 520 in order to thermally couple the heat sources in the heater substrate 600 to the microfluidic cartridge 200 positioned in the receiving tray 520. The application of pressure may be important to ensure consistent thermal contact between the heater substrate and the reaction chambers, gates, and valves, etc., in the microfluidic cartridge 200. When the receiving tray 520 is in a closed position, thereby being positioned under the aperture plate 540 of the optical unit 502, the force member, such as a motor assembly, positioned below the receiving tray 520 may begin traveling upwards towards the bottom side 506 of the optical unit 502, thereby bringing the receiving tray 520 closer to the optical unit 502. As the receiving tray 520 travels upwards towards the optical unit 502, the cartridge 200 may begin to come in contact with the bottom surface 506 of the aperture plate 540. The cartridge 200 may continue traveling upward until a sufficient pressure is received on the cartridge 200. The aperture plate 540 may be configured to apply an equal pressure across all points of the top of the cartridge 200 and thus, may press the cartridge 200 against the heater substrate 600 with uniform pressure. The aperture plate 540 may be selected to possess properties which facilitate this operation. For example, the material selection of the aperture plate 540 may provide very little deflection of the cartridge 200, when the cartridge 200 is pressed against the aperture plate 540.

The application of uniform pressure of the cartridge 200 against the heater substrate 600 may allow for uniform heating for each of the components of the cartridge 200 when desirable. Although uniform pressure and contact may be obtained between the heaters in the heater substrate 600 and the components (valves, gates, chambers, etc.) of the microfluidic networks in the cartridge 200, the heaters are not necessarily activated simultaneously. Thus, in certain embodiments, application of even pressure does not necessarily result in equal heating of different components of the cartridge 200. In some embodiments, both the activation of a specific heater in the heater substrate 600 along with the pressure applied by the aperture plate 540 to the cartridge 200 activate a particular component of cartridge 200.

Figure 9:
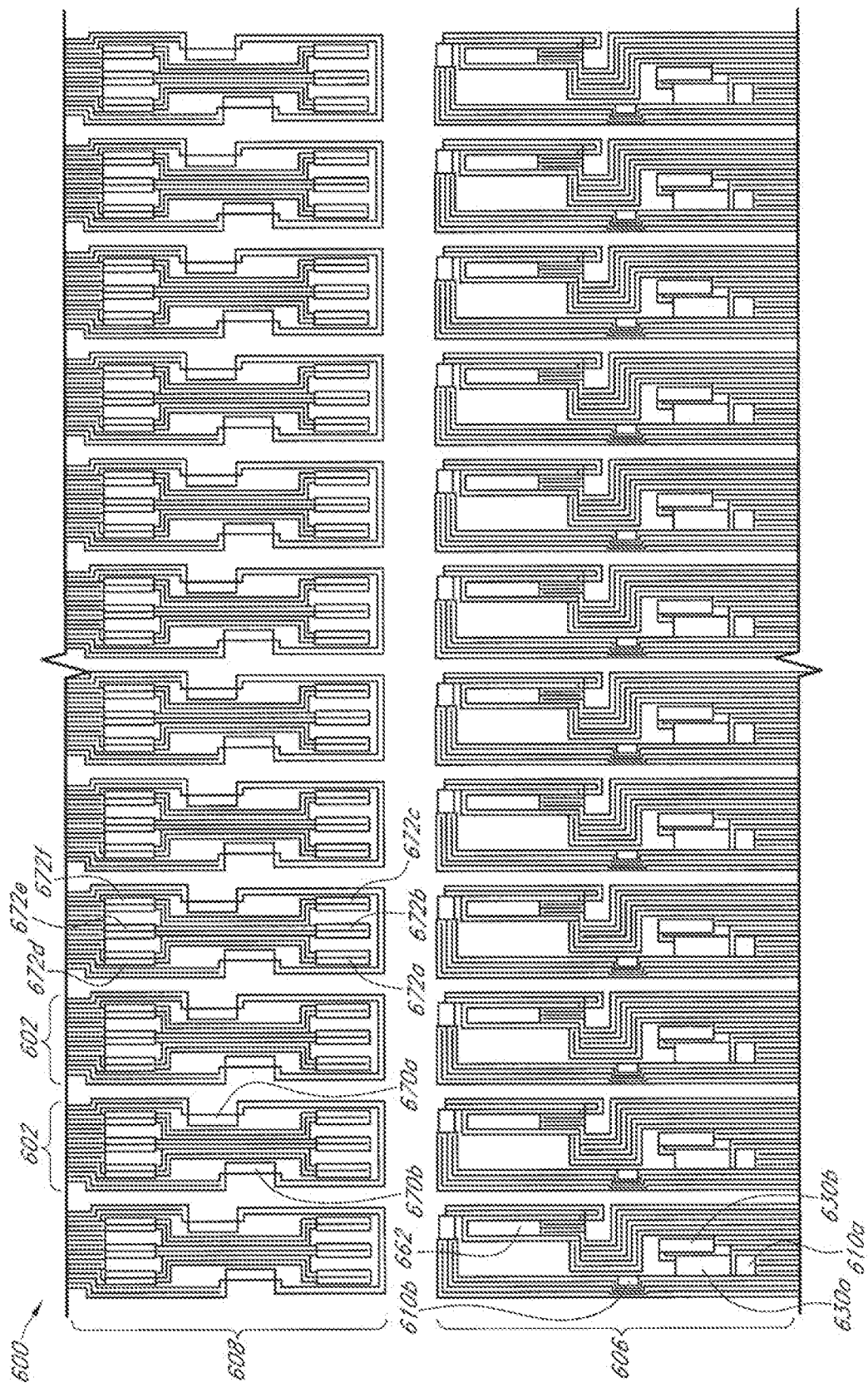
FIG. 9 illustrates a top plan view of a heater substrate.

FIG. 9 shows a top plan view of an exemplary heater substrate 600, which can be positioned in the bottom of the recessed bay 524 of the receiving tray 520. In various embodiments, the components of the microfluidic network in the sample lane 300 of the cartridge 200 can be heated by thermally coupling them with the heaters in the heater substrate 600. For example, the heater substrate can be positioned to heat (and/or cool) reaction chambers such as amplification chambers or detection chambers within the microfluidic cartridge 200. More specifically, the heater substrate 600 can be configured to thermally cycle a sample mixture comprising amplification reagents and an amplification-ready polynucleotide, thereby creating the conditions suitable for creating amplicons from the amplification-ready sample. The heater substrate 600 can also be configured to thermally cycle a sample mixture in the detection chambers, e.g., in order to perform melt-curve analyses or the like.

In preferred embodiments, each heater in the heater substrate 600 can be a contact heater, such as a resistive heater (or network thereof), a radiator, a fluidic heat exchanger and a Peltier device, or the like. The contact heat source can be configured in the recessed bay 524 to be thermally coupled to one or more distinct locations of the microfluidic cartridge 200 received in the receiving tray 520, whereby the distinct locations are selectively heated (and/or cooled). The contact heat sources can each be configured in the heater substrate 600 to be independently thermally coupled to a different distinct location in a microfluidic cartridge 200 received in the receiving tray 520, whereby the distinct locations are independently heated. The contact heat sources can be configured to be in direct physical contact with distinct locations of a microfluidic cartridge 200 received in the receiving tray 520.

As illustrated in FIG. 9, the heater substrate 600 can include one or more heater lanes 602, the number of which can correspond to the number of sample lanes 300 in the microfluidic cartridge 200. In some embodiments, the heater substrate 600 can include 12 heater lanes 602 to correspond to the 12 sample lanes 300 that may be in the microfluidic cartridge 200.

The heaters in a heater lane 602 may be divided conceptually into first stage heaters 606 and second stage heaters 608, to correspond to the first stage 206 and second stage 208 of the microfluidic cartridge 200. Among the heaters in the first stage 606 may be a first amplification gate heater 610a, a second amplification gate heater 610b, a first amplification valve heater 630a, a second amplification valve heater 630b, and an amplification chamber heater 662. Included in the second stage heaters 608 may be a first detection valve heater 670a, a second detection valve heater 670b, and detection chamber heaters 672a-f.

When the microfluidic cartridge 200 is placed in the recessed bay 524 of the receiving tray 520, the various components (e.g., reaction chambers, valves, and gates) of the microfluidic networks in the sample lanes 300 of the cartridge 200 are aligned adjacent to, and above, the corresponding heaters in the heater substrate 600, and consequently can be in thermal contact with the corresponding heaters in the heater substrate 600. When the microfluidic cartridge 200 is placed in the recessed bay 524, the heaters of the heater substrate 600 may be in physical contact with the respective components. For example, the first amplification gate heater 610a can be aligned adjacent to the first amplification gate 310a; the second amplification gate heater 610b can be aligned adjacent to the second amplification gate 310b; the first amplification valve heater 630a can be aligned adjacent to the first amplification valve 330a; the second amplification valve heater 630b can be aligned adjacent to the second amplification valve 330b; and the amplification chamber heater 662 can be aligned adjacent to the amplification chamber 362. Similarly, the first detection valve heater 670a may be aligned adjacent to the first detection valve 370a; the second detection valve heater 670b may be aligned adjacent to the second detection valve 370b; and the detection chamber heaters 672a-f may be aligned adjacent to the respective detection chambers 372a-f.

In some embodiments, multiple heaters can be configured to simultaneously and uniformly activate to heat their respective corresponding cartridge components of the microfluidic network in the microfluidic cartridge 200. Each heater can be independently controlled by a processor and/or control circuitry used in conjunction with the apparatus 10 described herein. Generally, the heating of microfluidic components (gates, valves, chambers, etc.) in the microfluidic cartridge 200, is controlled by passing currents through suitably configured micro-fabricated heaters, as illustrated in FIG. 9. Under control of suitable circuitry, the lanes 300 of a multi-lane cartridge can then be heated independently, and thereby controlled independently, of one another. Furthermore, as is described in more detail below, the individual valves 330a, 330b, 370a, 370b, gates 310a, 310b, amplification chamber 362, and detection chambers 372a-f, in a sample lane 300 can be heated independently, and thereby controlled independently, of one another within a given sample lane 300. This can lead to a greater energy efficiency and control of the apparatus 10, because not all heaters are heating at the same time, and a given heater is receiving current for only that fraction of the time when it is required to heat.

The heater substrate 600 may also include one or more heat sensors. In order to reduce the number of sensors or heaters required to control the heaters in a heater lane 602, the heaters may be used to sense temperature as well as provide heat, and thereby obviate the need to have a separate dedicated sensor for each heater. For example, the impedance and/or resistance of some materials change with the surrounding temperature. Accordingly, the resistance of the heater/sensors may be used as an indication of temperature when the sensors are not being actively heated.

In some embodiments, the heaters in the heater substrate 600 may be designed to have sufficient wattage to allow the heaters to be grouped in series or in parallel to reduce the number of electronically-controllable elements, thereby reducing the burden on the associated electronic circuitry. Heaters that are grouped together in this manner would be operated under synchronized and substantially simultaneous control.

In some embodiments, the first and second amplification valve heaters 630a, 630b can be grouped and configured to operate under synchronized control. In some embodiments, the first and second amplification gate heaters 610a, 610b can be grouped and configured to operate under synchronized control. In some embodiments, the first and second amplification valve heaters 630a, 630b and the amplification chamber heater 662 can be grouped and configured to operate under synchronized control. In some embodiments, the first and second detection valve heaters 670a, 670b can be grouped and configured to operate under synchronized control. In some embodiments, the detection chamber heaters 672a-f can be grouped and configured to operate under synchronized control. In some embodiments, the first and second detection valve heaters 670a, 670b and the detection chamber heaters 672a-f can be grouped and configured to operate under synchronized control. In some embodiments, the first stage heaters 606 can be grouped and configured to operate under synchronized control. In some embodiments, the second stage heaters 608 can be grouped and configured to operate under synchronized control.

In some embodiments, different combinations of the detection chamber heaters 672a-f can be grouped and configured to operate under synchronized control. For example, the detection chamber heaters on the same side of the second stage heaters 608 can be grouped and configured to operate under synchronized control. For example, in some embodiments, detection chamber heaters 672a-c can be grouped and configured to operate under synchronized control. For example, in some embodiments, detection chamber heaters 672d-f can be grouped and configured to operate under synchronized control.

In some embodiments, the detection chamber heaters on opposite sides of the second stage heaters can be grouped and configured to operate under synchronized control. For example, in some embodiments, the detection chamber heaters in a column, such as detection chamber heaters 672a and 672d, can be grouped and configured to operate under synchronized control. Similar grouping and configuring can be applied to heater groups including detection chamber heaters 672b and 672e and to heater groups including detection chamber heaters 672c and 672f. The detection heaters 672a-f can be configured to operate individually and independently or they can be configured to operate in groups of two (pairs), three (thirds), four, five or six, etc., or the like.

In some embodiments, the heating in the heater substrate 600 can be controlled by periodically turning the current on and off to a respective heater with varying pulse width modulation (PWM), wherein pulse width modulation refers to the on-time/off-time ratio for the current. The current can be supplied by connecting a micro fabricated heater to a high voltage source (for example, 30V), which can be gated by the PWM signal. In some embodiments, the device includes 48 PWM signal generators. In some embodiments there will be two PWM signal generators associated with each reaction chamber. Operation of a PWM generator includes generating a signal with a chosen, programmable period (the end count) and granularity. For instance, the signal can be 4000 µs (micro-seconds) with a granularity of 1 µs, in which case the PWM generator can maintain a counter beginning at zero and advancing in increments of 1 μs until it reaches 4000 μs, when it returns to zero. Thus, the amount of heat produced can be adjusted by adjusting the end count. A high end count corresponds to a greater length of time during which the micro fabricated heater receives current and therefore a greater amount of heat produced.

In various embodiments, the operation of a PWM generator can also include a programmable start count in addition to the aforementioned end count and granularity. In such embodiments, multiple PWM generators can produce signals that can be selectively non-overlapping (e.g., by multiplexing the on-time of the various heaters) such that the current capacity of the high voltage power is not exceeded.

Multiple heaters can be controlled by different PWM signal generators with varying start and end counts. The heaters can be divided into banks, whereby a bank defines a group of heaters of the same start count.

Methods of Detecting Target Nucleic Acids

In another aspect, provided herein are methods of detecting an analyte, e.g., a target nucleic acid from a sample, using the devices disclosed herein. The devices disclosed herein can advantageously be used to simultaneously analyze a single sample or multiple samples, for a plurality of target polynucleotides. Specifically, the "two-stage" design of the microfluidic cartridge enables for the testing and detection of many more targets than, for example, was previously possible in microfluidic cartridges that have a "one stage" design, where amplification and detection occur in the same chamber.

As used herein, the term "sample" can refer to a clinical specimen or sample from one or any number of sources, including, but not limited to, bodily fluids (including, but not limited to, blood, urine, serum, lymph, saliva, anal and vaginal secretions, perspiration, peritoneal fluid, pleural fluid, effusions, ascites, and purulent secretions, lavage fluids, drained fluids, brush cytology specimens, biopsy tissue, explanted medical devices, infected catheters, pus, biofilms and semen) of virtually any organism, with mammalian samples, particularly human samples, and environmental samples (including, but not limited to, air, agricultural, water and soil samples) finding use in the invention. In addition, samples can be taken from food processing, which can include both input samples (e.g. grains, milk or animal carcasses), samples in intermediate steps of processing, as well as finished food ready for the consumer.

The microfluidic network in each sample lane 300 shown in FIG. 3 is advantageously configured to carry out amplification, such as by PCR, on an amplification-ready sample, such as one containing nucleic acids extracted that have been from a sample. Several methods of nucleic acid extraction useful in the embodiments disclosed herein are known in the art. Exemplary discussions of nucleic acid extraction can be found, for example, in U.S. patent application Ser. No. 12/172,214, filed Jul. 11, 2008, U.S. patent application Ser. No. 12/172,208, filed Jul. 11, 2008, and U.S. patent application Ser. No. 12/281,247, filed Nov. 16, 2005, all of which are incorporated herein by reference in their entirety.

An amplification-ready sample can be prepared by mixing the sample nucleic acids (e.g., extracted sample nucleic acids) with amplification reagents. In some embodiments, the mixing is not performed within the microfluidic network of a microfluidic cartridge. For example, in some embodiments, an amplification-ready sample is prepared by mixing sample nucleic acids and amplification reagents within a container in a reagent holder 26. In other embodiments, the amplification-ready sample is prepared within the microfluidic network, e.g., the sample nucleic acids are mixed amplification reagents within a mixing chamber of the microfluidic network. Regardless of whether the mixture of sample nucleic acids and reagents occurs within the microfluidic network or outside of the microfluidic network, e.g., in a container in a reagent holder 26, the sample nucleic acids are introduced into the microfluidic network via an inlet port 302. Dispensing of the sample (whether amplification-ready or not) into the microfluidic network can be achieved either manually, or, for example, by an automated dispenser 400.

As discussed above, an amplification-ready sample is prepared by mixing nucleic acids from the sample to be analyzed with amplification reagents to create an amplification-ready sample. For example, an amplification-ready sample may include an amplification reagent mixture comprising a polymerase enzyme, a positive control nucleic acid, a fluorescent moiety specific for the positive control nucleic acids, and a plurality of nucleotides, and at least one fluorescent moiety that is selective for a target polynucleotide sequence.

Amplification

In some embodiments, the sample to be analyzed is dispensed within the microfluidic network via inlet port 302 and moved through to amplification chamber 362 as described elsewhere herein. The amplification-ready sample is isolated within the amplification chamber 362 by closing the amplification valves 330*a*, 330*b* in the microfluidic network upstream and downstream of the amplification chamber 362, respectively. In some embodiments, this is achieved by heating a TRS 345 to seal one or more channels (e.g., the first and second channels 360, 364 that communicate with the amplification chamber 362. Once isolated in the amplification chamber 362, the device may be activated to thermal cycle the amplification-ready sample within the amplification chamber 362 as described elsewhere herein, to generate an amplified sample. Specifically, as described elsewhere herein, the amplification chamber 362 of the microfluidic network is in thermal communication with, or thermally coupled to, an external heat source (e.g, the heater substrate 600). Thermal cycling of the amplification-ready sample creates an amplified sample, which, when target nucleic acids are present in the sample under analysis, includes amplicons of the target nucleic acids, i.e., target amplicons.

In some embodiments, the sample or specimen is contacted with a set of amplification primers under standard PCR conditions. For a review of PCR technology, including standard PCR conditions, applied to clinical microbiology, see DNA Methods in Clinical Microbiology, Singleton P., published by Dordrecht; Boston: Kluwer Academic, (2000) Molecular Cloning to Genetic Engineering White, B.A. Ed. in *Methods in Molecular Biology* 67: Humana Press, Totowa (1997) and "PCR Methods and Applications", from 1991 to 1995 (Cold Spring Harbor Laboratory Press). Non-limiting examples of "PCR conditions" include the conditions disclosed in the references cited herein, such as, for example, 50 mM KCl, 10 mM Tris-HCl (pH 9.0), 0.1% Triton X-100, 2.5 mM $MgCl_2$, with an annealing temperature of 72° C.; or 4 mM $MgCl_2$, 100 mM Tris, pH 8.3, 10 mM KCl, 5 mM $(NH_4)_2SO_4$, 0.15 mg BSA, 4% Trehalose, with an annealing temperature of 59° C., or 50 mM KCl, 10 mM Tris-HCl (pH 9.0), 0.1% Triton X-100, 2.5 mM $MgCl_2$, with an annealing temperature of 55° C., or the like.

In some embodiments, the amplification-ready sample is amplified within the amplification chamber 362 by the polymerase chain reaction (PCR). Generally, in PCR, a target polynucleotide sequence is amplified by reaction with at least one oligonucleotide primer or pair of oligonucleotide primers. In embodiments wherein the sample nucleic acids are amplified by PCR, the amplification ready sample minimally comprises template nucleic acid (except in the case of a negative control as described below) and oligonucleotide primers and/or probes in combination with suitable buffers, salts, and the like, and an appropriate concentration of a nucleic acid polymerase. As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template until synthesis terminates. An appropriate concentration includes one that catalyzes this reaction in the presently described methods. Known DNA polymerases useful in the methods disclosed herein include, for example, *E. coli* DNA polymerase I, T7 DNA polymerase, Thermus thermophilus (Tth) DNA polymerase, Bacillus stearothermophilus DNA polymerase, Thermococcus litoralis DNA polymerase, Thermus aquaticus (Taq) DNA polymerase Pyrococcusfuriosus (Pfu) DNA polymerase, and the like.

In addition to the above components, the reaction mixture of the present methods includes primers, probes, and deoxyribonucleoside triphosphates (dNTPs). Usually the reaction mixture will further comprise four different types of dNTPs corresponding to the four naturally occurring nucleoside bases, i.e., dATP, dTTP, dCTP, and dGTP. In some of the embodiments disclosed herein, each dNTP will typically be present in an amount ranging from about 10 to 5000 µM, usually from about 20 to 1000 µM, about 100 to 800 µM, or about 300 to 600 µM.

As used herein, the terms "primer" and "probe" include, but are not limited to oligonucleotides or nucleic acids. The terms "primer" and "probe" encompass molecules that are analogs of nucleotides, as well as nucleotides. Nucleotides and polynucleotides, as used herein shall be generic to polydeoxyribonucleotides (containing 2-deoxy-D-ribose), to polyribonucleotides (containing D-ribose), to any other type of polynucleotide which is an N- or C-glycoside of a purine or pyrimidine base, and to other polymers containing nonnucleotidic backbones, for example, polyamide (e.g., peptide nucleic acids (PNAs)) and polymorpholino (commercially available from the Anti-Virals, Inc., Corvallis, Oreg., as NEUGENE™ polymers), and other synthetic sequence-specific nucleic acid polymers providing that the polymers contain nucleobases in a configuration which allows for base pairing and base stacking, such as is found in DNA and RNA.

In some embodiments, the "primers" or "probes" disclosed herein can contain locked nucleic acids (LNA). "Locked nucleic acids" (LNAs) are ribonucleotides which contain a methylene bridge which joins the 2' oxygen of the ribose with the 4' carbon (see FIG. 27). Braasch D. A. and Corey, D. R. (2001), Locked nucleic acids (LNA); fine-tuning the recognition of DNA and RNA. Chem. Biol. 8, 1-7, provide an overview of LNAs. This article is herein explicitly incorporated by reference in its entirety. LNAs are available commercially, for example, from the company Proligo, Boulder, Colo., USA. Phosphorothioates are also known to the person skilled in the art and may be ordered, for example, from MWG-Biotech AG, Ebersberg, Germany. Accordingly, in some embodiments, the "primers" or "probes" disclosed herein can include 1, 2, 3, 4, 5, 6, 7, 8, 9,10, or more LNAs.

The terms nucleotide and polynucleotide include, for example, 3'-deoxy-2',5'-DNA, oligodeoxyribonucleotide N3'→P5' phosphoramidates, 2'-O-alkyl-substituted RNA, double- and single-stranded DNA, as well as double- and single-stranded RNA, DNA:RNA hybrids, and hybrids between PNAs and DNA or RNA. The terms also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with a halogen, an aliphatic group, or are functionalized as ethers, amines, or the like. Other modifications to nucleotides or polynucleotides involve rearranging, appending, substituting for, or otherwise altering functional groups on the purine or pyrimidine base which form hydrogen bonds to a respective complementary pyrimidine or purine. The resultant modified nucleotide or polynucleotide may form a base pair with other such modified nucleotidic units but not with A, T, C, G or U. For example, guanosine (2-amino-6-oxy-9-beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described U.S. Pat. No. 5,780,610 to Collins et al. The non-natural base pairs referred to as κ and π, may be synthesized by the method described in Piccirilli et al. (1990) Nature 343:33-37 for the synthesis of 2,6-diaminopyrimidine and its complement (1-methylpyrazolo[4,3]-pyrimidine-5,7-(4H,6H)-dione. Other such modified nucleotidic units which form unique base pairs have been described in Leach et al. (1992) J. Am. Chem. Soc. 114:3675-3683 and Switzer et al., supra, or will be apparent to those of ordinary skill in the art.

The primers and/or probes are preferably between 10 and 45 nucleotides in length. For example, the primers and or probes can be at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length. Primers and/or probes can be provided in any suitable form, included bound to a solid support, liquid, and lyophilized, for example. In some embodiments, the primers and/or probes include oligonucleotides that hybridize to a target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under stringent conditions or standard PCR conditions as discussed below. As used herein, the term "standard PCR conditions" include, for example, any of the PCR conditions disclosed herein, or known in the art, as described in, for example, PCR 1: A Practical Approach, M. J. McPherson, P. Quirke, and G. R. Taylor, Ed., (c) 2001, Oxford University Press, Oxford, England, and PCR Protocols: Current Methods and Applications, B. White, Ed., (c) 1993, Humana Press, Totowa, N.J.

As used herein, the term "substantially complementary" refers to the complementarity between two nucleic acids, e.g., the complementary region of the capture probe and the target sequence, and/or between the linker sequence of the capture probe and the complementary region of the competitor nucleic acid. The complementarity need not be perfect; there may be any number of base pair mismatches that between the two nucleic acids. However, if the number of mutations is so great that no hybridization can occur under even the least stringent of hybridization conditions, the sequence is not a substantially complementary sequence. When two sequences are referred to as "substantially complementary" herein, it is meant that the sequences are sufficiently complementary to the each other to hybridize under the selected reaction conditions. The relationship of nucleic acid complementarity and stringency of hybridization sufficient to achieve specificity is well known in the art and described further below in reference to sequence identity, melting temperature and hybridization conditions. Therefore, substantially complementary sequences can be used in any of the detection methods described herein. Such probes can be, for example, perfectly complementary or can contain from 1 to many mismatches so long as the hybridization conditions are sufficient to allow, for example discrimination between a target sequence and a non-target sequence. Accordingly, substantially complementary sequences can refer to sequences ranging in percent identity from 100, 99, 98, 97, 96, 95, 94, 93, 92, 91, 90, 89, 85, 80, 75 or less, or any number in between, compared to the reference sequence.

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The amplification-ready sample prepared in the first step of the methods of the embodiments disclosed herein further includes an aqueous buffer medium that includes a source of monovalent ions, a source of divalent cations, and a buffering agent. Any convenient source of monovalent ions, such as potassium chloride, potassium acetate, ammonium acetate, potassium glutamate, ammonium chloride, ammonium sulfate, and the like may be employed. The divalent cation may be magnesium, manganese, zinc, and the like, where the cation will typically be magnesium. Any convenient source of magnesium cation may be employed, including magnesium chloride, magnesium acetate, and the like. The amount of magnesium present in the buffer may range from 0.5 to 10 mM, and can range from about 1 to about 6 mM, or about 3 to about 5 mM. Representative buffering agents or salts that may be present in the buffer include Tris, Tricine, HEPES, MOPS, and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, for example, about pH 6.0, 6.5, 7.0, 7.5, 8.0, 8.5, 9.0, or 9.5. Other agents that may be present in the buffer medium include chelating agents, such as EDTA, EGTA, and the like. In some embodiments, the reaction mixture can include BSA, or the like.

In preparing the reaction mixture, the various constituent components may be combined in any convenient order. For example, the buffer may be combined with primer, polymerase, and then template nucleic acid, or all of the various constituent components may be combined at the same time to produce the reaction mixture.

Alternatively, commercially available premixed reagents can be utilized in the methods disclosed herein according to the manufacturer's instructions, or modified to improve reaction conditions (e.g., modification of buffer concentration, cation concentration, or dNTP concentration, as necessary), including, for example, TAQMAN® Universal PCR Master Mix (Applied Biosystems), OMNIMIX® or SMARTMIX® (Cepheid), IQ™ Supermix (Bio-Rad Laboratories), LIGHTCYCLER® FastStart (Roche Applied Science, Indianapolis, Ind.), or BRILLIANT® QPCR Master Mix (Stratagene, La Jolla, Calif.). In some embodiments, the reagents can be premixed and disposed within reaction chambers, e.g., amplification chambers and/or detection chambers, of the systems disclosed herein. In some embodiments, reagents can be lyophilized and predisposed within vessels in a reagent rack, or the like.

Following preparation of the reaction mixture, the reaction mixture can be subjected to primer extension reaction conditions ("conditions sufficient to provide polymerase-based nucleic acid amplification products"), i.e., conditions that permit for polymerase-mediated primer extension by addition of nucleotides to the end of the primer molecule using the template strand as a template. In many embodiments, the primer extension reaction conditions are amplification conditions, which conditions include a plurality of reaction cycles, where each reaction cycle comprises: (1) a denaturation step, (2) an annealing step, and (3) a polymerization step. In some embodiments, the reaction cycles do not include a specific amount of time allotted for annealing, but rather combine annealing and polymerization steps. The number of reaction cycles will vary depending on the application being performed, but will usually be at least 15, more usually at least 20, and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double-stranded or hybridized nucleic acid present in the reaction mixture to dissociate. For denaturation, the temperature of the reaction mixture will usually be raised to, and maintained at, a temperature ranging from about 85 to 100° C., usually from about 90 to 98° C., and more usually from about 93 to 96° C., for a period of time ranging from about 3 to 120 sec, usually from about 3 sec.

Following denaturation, the reaction mixture can be subjected to conditions sufficient for primer annealing to template nucleic acid present in the mixture (if present), and for polymerization of nucleotides to the primer ends in a manner such that the primer is extended in a 5' to 3' direction using the nucleic acid to which it is hybridized as a template, i.e., conditions sufficient for enzymatic production of primer extension product. In this embodiment, the annealing and extension processes occur in the same step. The temperature to which the reaction mixture is lowered to achieve these conditions will usually be chosen to provide optimal efficiency and specificity, and will generally range from about 50 to 75° C., usually from about 55 to 70° C., and more usually from about 60 to 68° C., more particularly around 60° C. Annealing conditions will be maintained for a period of time ranging from about 15 sec to 30 min, usually from about 20 sec to 5 min, or about 30 sec to 1 minute, or about 30 seconds.

This step can optionally comprise one of each of an annealing step and an extension step with variation and optimization of the temperature and length of time for each step. In a two-step annealing and extension, the annealing step is allowed to proceed as above. Following annealing of primer to template nucleic acid, the reaction mixture will be further subjected to conditions sufficient to provide for polymerization of nucleotides to the primer ends as above. To achieve polymerization conditions, the temperature of the reaction mixture will typically be raised to or maintained at a temperature ranging from about 65 to 75° C., usually from about 67 to 73° C. and maintained for a period of time ranging from about 15 sec to 20 min, usually from about 30 sec to 5 min.

In some embodiments, the cycling can include a 15-minute initial denaturation at 95° C., which is performed only once, followed by a denaturation step at 95° C. for 1 second, and an annealing/elongation step at 60° C. for 25 seconds. This two-step cycle can be repeated multiple times, e.g., about 45 times. In some embodiments, a final elongation step can be added at 72° C. for 10 minutes.

In some embodiments, the cycling can include a 15-minute initial denaturation step at 95° C., is followed by multiple cycles (e.g., about 45 cycles) of: denaturation at 95° C. for 1 second, annealing at 60° C. for 9 seconds and elongation at 72° C. for 9 seconds. A final elongation step can be added of 72° C. for 10 minutes.

The person skilled in the art of nucleic acid amplification knows the existence of other rapid amplification procedures such as ligase chain reaction (LCR), transcription-based amplification systems (TAS), self-sustained sequence replication (3SR), nucleic acid sequence-based amplification (NASBA), strand displacement amplification (SDA) and branched DNA (bDNA) (Persing et al. (1993) Diagnostic Molecular Microbiology: Principles and Applications (American Society for Microbiology, Washington, D.C.). The scope of the embodiments disclosed herein is not limited to the use of amplification by PCR, but rather includes the use of any rapid nucleic acid amplification methods or any other procedures described herein that can be readily carried out on the systems disclosed herein.

Detection

Following amplification, the amplified sample is then moved within the microfluidic network to one or more detection chamber 372*a-f*. In some embodiments, equal amounts of the amplified are moved to a plurality of detection chambers. For example, in some embodiments, equal volumes of the amplified sample are transferred into 2, 4, 6, 8, 10, 12, or more, detection chambers. Movement of the amplified sample within the microfluidic network is described elsewhere herein, and can comprise opening an amplification gate 310*a* upstream from the amplification chamber 362. In some embodiments, the amplification gate 310*a* comprises a TRS, and opening the gate comprises applying heat to the TRS. In some embodiments, heating a TRS within the amplification gate 310*a* removes the TRS from an upstream channel, e.g., the first channel 360, in communication with the amplification chamber 362.

Fluidic pressure, e.g., pressure from discharging fluid or gas into the network, can be applied to the network, in order to facilitate movement of the amplified sample within the microfluidic networks. For example, the application of a fluidic pressure can be achieved by discharging a fluid (e.g., a gas or liquid), from a pipette into an inlet of the microfluidic network that resides upstream from the sample, thereby forcing the sample downstream within the microfluidic network. Once the amplified sample is transferred into the detection chambers 372*a-f*, the amplified sample is isolated within the detection chambers 372*a-f* of the microfluidic network. In some embodiments, isolating the amplified sample within the detection chambers 372*a-f* can comprise closing detection valves 370*a*, 370*b* located upstream and downstream of the detection chambers 372*a-f*. In some embodiments, the detection valves 370*a*, 370*b* located upstream and downstream of the detection chamber(s) comprise a TRS, and are closed by heating the TRS to seal the upstream and downstream channels, respectively, that are in communication with the detection chambers 370*a*, 370*b*.

Once isolated inside the detection chambers 372*a-f*, the amplified sample can be contacted with, or mixed with a fluorescent moiety that is specific for the target nucleic acid and target amplicon, to create a detection mixture. In some embodiments, the fluorescent moiety can comprise an oligonucleotide probe operably coupled to a fluorescent moiety that is complementary to, or substantially complementary to, a nucleotide sequence within the target amplicon. In some embodiments, the term "specific for," in reference to oligonucleotides and probes, refers to an oligonucleotide or probe that hybridizes exclusively or only to a cognate target sequence, under standard PCR/annealing conditions as described elsewhere herein.

In some embodiments, the microfluidic cartridges 200 can include oligonucleotide probes, e.g., in a lyophilized form, in the detection chambers 372a-f. In some embodiments, oligonucleotide probes can be added to the microfluidic network after the sample to be analyzed has been introduced into the microfluidic cartridge. In some embodiments, probes in the form of lyophilized beads can be placed in the detection chambers 372a-f of the cartridge 200 during the cartridge manufacturing process. In this embodiment, the lyophilized beads are larger in diameter than the diameters of the subchannels 365a1-365a3 and 365b1-365b3 leading into the detection chambers 372a-f and subchannels 367a, 367b leading out of the detection chambers 372a-f. In this manner, the lyophilized beads are blocked from leaving the detection chambers 372a-f after final manufacture of the cartridge 200 and remain in the detection chambers 372a-f during transportation and use.

In some embodiments, the probes are inserted into the detection chambers 372a-f during the manufacture of the cartridge 200 using a drying process. In this embodiment, an amount of probe in liquid solution is added to each of the detection chamber 372a-f; then the liquid is dried, evaporating the solvent and leaving the dried-on probe in each of the detection chambers 372a-f. Whether the probe used is a lyophilized bead or is dried-on, an excess amount of the probe can be placed in the detection chambers 372a-f to compensate for a portion that may dissolve in the sample 350 that passes through the detection chambers 372a-f and enters the subchannels 367a, 367b and the fourth channel 374.

The skilled artisan will appreciate that several probe technologies are useful in the embodiments described herein. By way of example, the embodiments disclosed herein can be used with TAQMAN™ probes, molecular beacon probes, SCORPION™ probes, Sunrise probes, and the like.

TaqMan™ assays are homogenous assays for detecting polynucleotides (see U.S. Pat. No. 5,723,591). In TAQMAN™ assays, two amplification primers flank a central TAQMAN™ probe oligonucleotide. The probe oligonucleotide contains a fluorophore and quencher. During the polymerization step of the amplification process, the 5' nuclease activity of the polymerase cleaves the probe oligonucleotide, causing the fluorophore moiety to become physically separated from the quencher, which increases fluorescence emission. As more amplicon is created, the intensity of emission at the novel wavelength increases.

Molecular beacons are an alternative to TAQMAN™ probes for the detection of polynucleotides (see U.S. Pat. Nos. 6,277,607; 6,150,097; and 6,037,130). Molecular beacons are oligonucleotide hairpins which undergo a conformational change upon binding to a perfectly matched template. The conformational change of the oligonucleotide increases the physical distance between a fluorophore moiety and a quencher moiety present on the oligonucleotide. This increase in physical distance causes the effect of the quencher to be diminished, thereby increasing the signal derived from the fluorophore.

Another method of detection useful in the embodiments disclosed herein includes the "adjacent probes method." In this method, PCR is used to amplify the target sequence in the presence of two nucleic acid probes that hybridize to adjacent regions of the target sequence. One of the probes is labeled with an acceptor fluorophore and the other probe labeled with a donor fluorophore of a fluorescence energy transfer pair. Upon hybridization of the two probes with the target sequence, the donor fluorophore interacts with the acceptor fluorophore to generate a detectable signal. The sample is then excited with light at a wavelength absorbed by the donor fluorophore and the fluorescent emission from the fluorescence energy transfer pair is detected for the determination of that target amount. The "adjacent probes method" is disclosed, e.g., in U.S. Pat. No. 6,174,670B1.

Another method useful in the embodiments disclosed herein include the use of "sunrise primers." Sunrise primers utilize a hairpin structure similar to molecular beacons, but in contrast to molecular beacons, are attached to a target binding sequence which serves as a primer. When the primer's complementary strand is synthesized, the hairpin structure is disrupted, thereby eliminating quenching. These primers detect amplified product and do not require the use of a polymerase with a 5' exonuclease activity. Sunrise primers are described by Nazarenko et al. (Nucleic Acids Res. 25:2516-21 (1997) and in U.S. Pat. No. 5,866,336).

Yet another method useful in the embodiments disclosed herein include the use of SCORPION™ probes. SCORPION™ probes combine a primer with an added hairpin structure, similar to Sunrise primers. However, the hairpin structure of SCORPION™ probes is not opened by synthesis of the complementary strand, but by hybridization of part of the hairpin structure with a portion of the target which is downstream from the portion which hybridizes to the primer.

DzyNA-PCR is another method useful in the embodiments disclosed herein, that involves the use of a primer containing the antisense sequence of a DNAzyme, which is an oligonucleotide capable of cleaving specific RNA phosphodiester bonds. The primer binds to a target sequence and drives an amplification reaction producing an amplicon which contains the active DNAzyme. The active DNAzyme then cleaves a generic reporter substrate in the reaction mixture. The reporter substrate contains a fluorophore-quencher pair, and cleavage of the substrate produces a fluorescence signal which increases with the amplification of the target sequence. DzyNA-PCR is described in Todd et al., Clin. Chem. 46:625-30 (2000), and in U.S. Pat. No. 6,140,055.

Still other embodiments disclosed herein include the use of a "Q-PNA probe," that is a quenchere-labeled peptide nucleic acid, in conjunction with a fluorophore-labeled oligonucleotide primer. The Q-PNA hybridizes to a tag sequence at the 5' end of the primer. The use of Q-PNA probes is described in Fiandaca et al. Genome Research. 11:609-613 (2001).

Li et al. describes a double stranded probe having a quencher and fluorophore on opposite oligonucleotide strands. Li et al. Nucleic Acids Research. 30: 1-9. When not bound to the target, the strands hybridize to each other and the probe is quenched. However, when a target is present at least one strand hybridizes to the target resulting in a fluorescent signal.

Fluorescent Moieties

As discussed above, some embodiments, disclosed herein include contacting the an amplified sample with a fluorescent moiety, e.g., a fluourescent moiety that is operably coupled to an oligonucleotide that is specific for a polynucleotide sequence found within the target amplicon. Several fluorescent moieties useful in the embodiments disclosed herein are known in the art. By way of example, fluorophore labels and moieties useful in the embodiments and probes disclosed herein include, but are not limited to, dyes of the fluorescein family, the carboxyrhodamine family, the cyanine family, and the rhodamine family. Other families of dyes that can be used in the invention include, e.g., polyhalofluorescein-family dyes, hexachlorofluorescein-family dyes, coumarin-family dyes, oxazine-family dyes, thiazine-family dyes, squaraine-family dyes, chelated lanthanide-family dyes, the family of dyes available under the trade designation Alexa Fluor J, from Molecular Probes, and the family of dyes available under the trade designation Bodipy J, from Invitrogen (Carlsbad, Calif.). Dyes of the fluorescein family include, e.g., 6-carboxyfluorescein (FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), 2'-chloro-7'-phenyl-1,4-dichloro-6-carboxyfluorescein (VIC), 6-carboxy-X-rhodamine (ROX), and 2',4',5',7'-tetrachloro-5-carboxy-fluorescein (ZOE). Dyes of the carboxyrhodamine family include tetramethyl-6-carboxyrhodamine (TAMRA), tetrapropano-6-carboxyrhodamine (ROX), Texas Red, R110, and R6G. Dyes of the cyanine family include Cy2, Cy3, Cy3.5, Cy5, Cy5.5, and Cy7. Fluorophores are readily available commercially from, for instance, Perkin-Elmer (Foster City, Calif.), Molecular Probes, Inc. (Eugene, Oreg.), and Amersham GE Healthcare (Piscataway, N.J.).

As discussed above, in some embodiments, probes used in the methods disclosed herein can comprise a quencher. Quenchers may be fluorescent quenchers or non-fluorescent quenchers. Fluorescent quenchers include, but are not limited to, TAMRA, ROX, DABCYL, DABSYL, cyanine dyes including nitrothiazole blue (NTB), anthraquinone, malachite green, nitrothiazole, and nitroimidazole compounds. Exemplary non-fluorescent quenchers that dissipate energy absorbed from a fluorophore include those available under the trade designation Black Hole™ from Biosearch Technologies, Inc. (Novato, Calif.), those available under the trade designation Eclipse™. Dark, from Epoch Biosciences (Bothell, Wash.), those available under the trade designation Qx1J, from Anaspec, Inc. (San Jose, Calif.), and those available under the trade designation Iowa Black™ from Integrated DNA Technologies (Coralville, Iowa).

Typically, a fluorophore and a quencher are used together, and may be on the same or different oligonucleotides. When paired together, a fluorophore and fluorescent quencher can be referred to as a donor fluorophore and acceptor fluorophore, respectively. A number of convenient fluorophore/quencher pairs are known in the art (see, for example, Glazer et al, Current Opinion in Biotechnology, 1997; 8:94-102; Tyagi et al., 1998, Nat. Biotechnol., 16:49-53) and are readily available commercially from, for instance, Molecular Probes (Junction City, Oreg.), and Applied Biosystems (Foster City, Calif.). Examples of donor fluorophores that can be used with various acceptor fluorophores include, but are not limited to, fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2-,2'-disulfonic acid derivatives. Acceptor fluorophores typically depend upon the donor fluorophore used. Examples of acceptor fluorophores include, but are not limited to, LC-Red 640, LC-Red 705, CyS, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorophores are readily available commercially from, for instance, Molecular Probes or Sigma Chemical Co. (St. Louis, Mo.).

In some embodiments, after the amplification reaction has been mixed with the probe(s), the detection reaction is subjected to a detection thermocycling reaction. The detection thermocycling can involve heating the detection reaction so as to denature the double-stranded polynucleotides, followed by continuously ramping the temperature up or down over a set period of time and analyzing melting and reannealing curves. The use of fluorescence melting curves to monitor hybridization has been described, e.g., in L. E. Morrison & L. M. Stols, Sensitive fluorescence-based thermodynamic and kinetic measurements of DNA hybridization in solution, 32 Biochemistry 3095-3104, 1993), U.S. Pat. No. 6,174,670, and in U.S. Pat. No. 6,140,054 the entire contents of which are each herein incorporated by reference.

In some embodiments, the detection comprises illuminating the detection reaction with a wavelength of light for eliciting fluorescence by the fluorescent moiety, and continuously monitoring, as a function of temperature, the fluorescence emitted. In some embodiments, more than one fluorescent moiety, e.g., 2, 3, 4, 5, 6, or more, wherein each fluorescent moiety is specific for a different nucleic acid sequence present in a target amplicon, can be mixed with the amplified sample in the detection chambers 372a-f. The use of more than one fluorescent moiety, wherein each fluorescent moiety is specific for a different nucleic acid sequence, enables the specific hybridization to (and thus detection of) more than one target nucleic acid sequence sequence, whether the different target nucleic acid sequences are present within a single amplicon, or whether the different target nucleic acid sequences are located within different amplicons, e.g., different amplicons generated by a multiplex PCR reaction in the amplification stage of the reaction.

In some embodiments, different oligonucleotide probes that are substantially complementary to different target nucleic acid sequences (within a single amplicon, or in different amplicons), and that are each operably coupled to a single fluorescent moiety can be used to detect multiple target sequences (e.g., different loci within a single amplicon or different amplicons) in a single detection reaction. For example, different oligonucleotides, preferably that have distinct $T_m$'s can each be operably coupled to a single type of fluorescent moiety. Because each different oligonucleotide probe has a distinct $T_m$, the presence of the target nucleotide sequence within an amplicon(s) can be monitored by measuring the fluorescence emission as a function of temperature at a single emission wavelength. By way of example, in some embodiments, each detection chamber 372a-f can contain oligonucleotide probes that comprise two, three, four, or more different nucleic acid sequences, each having distinct $T_m$'s, and each oligonucleotide being operably coupled to the same type of fluorescent moiety.

Alternatively, a single detection reaction can include a number of oligonucleotide different probes, each of which has a different oligonucleotide sequence, wherein each different oligonucleotide sequence is be operably coupled to different type of fluorescent moiety. This way, the each different probe within the detection reaction can be distinguished from other probes based on the distinguishable emission spectra of the fluorescent moieties. Preferably, the emission spectra of the different fluorescent moieties do not overlap, or do not have significant overlap, such that the different fluorescent moieties can be readily distinguished.

In some embodiments, the protocol used in the detection chambers 372a-f can include subjecting the detection reaction to an initial cycle to melt double stranded nucleic acids including any target amplicons, and lowering the temperature to allow the annealing of one or more oligonucleotide probes to anneal to complementary (or substantially complementary) sequences of the single stranded amplicon DNA, to form a duplex. By way of example, in some embodiments, the detection reaction can be heated in order to ensure complete denaturation of double stranded nucleic acids in the detection mixture, including denaturation of target amplicon sequences. By way of example only, the detection reaction can be heated to about 90-100° C. for a period of time, e.g., about 15 sec to about 1 min. Following denaturation, the temperature of the detection mixture is lowered to allow annealing of probe(s) to target sequence(s). By way of example only, the annealing step can include cooling the detection reaction to about 45° C. for a period of time, e.g., for about 15 seconds to a minute, or longer, or any period of time in between, e.g., 30 sec.

After the annealing step, the temperature of the detection mixture can be slowly raised within the detection chamber 372a-f, while continuously observing a fluorescence signal, in order to monitor (and record) the dissociation of, or melting of, the duplex formed by the probe and amplicon sequence. Specifically, the temperature of the detection mixture can incrementally ramped from the annealing temperature to a second temperature (e.g., the denaturation temperature). For example, in some embodiments, the detection reaction is ramped from the annealing temperature (or a first temperature that is lower than the $T_m$ of any probe in the detection mixture), to the second temperature in increments of 0.05° C., 0.1° C., 0.2° C., 0.3° C., 0.4° C., 0.5° C., 0.6° C., 1.0° C., 1.5° C., 2.0° C., 2.5° C., 3.0° C., 3.5° C., 4.0° C., 4.5° C., 5.0° C., or greater, or any increment in between. Using the devices disclosed herein, the fluorescence signal emitted at each temperature increment is measured using the heater/detector module disclosed herein. In some embodiments, the ramping from annealing temperature to the second temperature (e.g., melting temperature), is referred to as a "melt protocol." The change in fluorescence caused by the dissociation of a fluorescent probe from a cognate target sequence throughout the course of the melt protocol can be monitored over time/temperature during the melt protocol, and can be used to determine the presence and/or amount of a target sequence.

In some embodiments, the heating of the detection chambers 372a-f can be synchronized and staggered in order to achieve a desired detector cycle time. For example, in some embodiments, the total time for melt protocol/detection is less than 30 minutes, e.g., between about 8-27 minutes, 10-26 minutes, 15-25 minutes, 20-25 minutes, or the like. By way of example, in some embodiments, the melt protocol takes about 22-25 minutes. In some embodiments, each of the detection chambers 372a-f within a sample lane 300 is subjected to the same melt protocol. In some embodiments, some of the detection chambers 372a-f within a sample lane 300 are subjected to different melt protocols.

In some embodiments, more than one probe with a single species of fluorescent moiety can be used in the same detection chamber, wherein each probe comprises a different oligonucleotide sequence, and wherein each probe has a different $T_m$. For example, in some embodiments, two, three, four, or more, different probes with the same species of fluorescent moiety can be used in the same detection chamber, in order to detect two, three, four, or more, different target nucleic acid sequences.

Accordingly, in some embodiments, each lane 300 can be used to detect numerous target nucleic acid sequences. By way of example only, in some embodiments, 108 different target nucleic acid sequences can be detected in each of the lanes. Specifically, each detection chamber 372a-f can include multiple different probes, e.g., eighteen different probes, wherein the probes comprise eighteen different oligonucleotide sequences specific for eighteen different target nucleic acid sequences, and wherein the probes collectively comprise six different types of fluorescent moieties (i.e., three different oligonucleotide sequences having distinct $T_m$'s can be coupled to a single type of fluorescent moiety). In this way, six different fluorescent moieties times three different oligonucleotide probes/each moiety times six different detection chambers, can be used to detect 108 different target nucleic acids.

FIGS. 10A-D provide representations of the microfluidic network of the sample lane 300, such as the sample lanes 300 located in the cartridge 200. FIGS. 10A-D illustrate the movement of a sample 350 as the sample 350 is processed in the microfluidic network, as it undergoes thermocycling and detection in the amplification chamber 362 and detection chambers 372a-f.

Figure 10A:
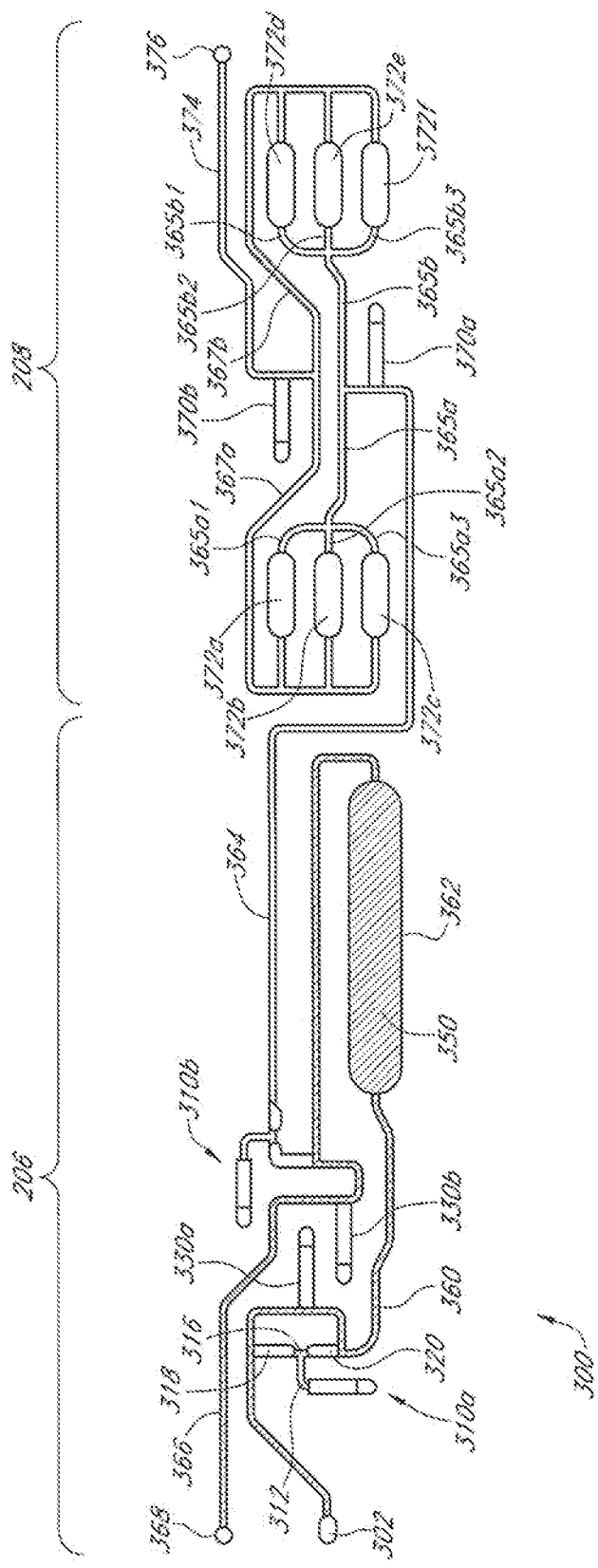
FIGS. 10A-10D illustrate the movement of fluid in the sample lane of a microfluidic cartridge.

Before introducing the sample 350 into the sample lane 300, the cartridge 200 can be positioned to receive the sample 350 from the fluid dispenser 400. Referring to FIG. 1C, the receiving tray 520a may be opened, with the cartridge 200 positioned in the recessed bay 524 of the receiving tray 520a. The fluid dispenser 400 can withdraw the prepared sample 350 from the process tube 32 in the rack 24 into a pipette 402 of the fluid dispenser 400 and carry the sample 350 in the pipette 402 to a position approximate to the cartridge 200 in the receiving tray 520. The fluid dispenser 400 can position the pipette tip 402 in the inlet 302. The fluid dispenser 400 can then dispense a volume of the sample 350 from the pipette tip 402 into the sample lane 300 through the inlet 302 of the sample lane 300. The volume of the sample 350 introduced into the inlet 302 can be, for example, approximately 10 µl. FIG. 10A illustrates the state of sample processing within the microfluidic network following introduction of the sample 350 into the sample lane 300 through the inlet 302 of the sample lane 300.

In some embodiments, prior to introduction of the sample 350 into the sample lane 300, the first and second amplification gates 310a, b of the sample lane 300 can be in a closed state, such that the TRS (e.g., wax) 345 is positioned in the first channel 360 to obstruct passage of the sample 350 through the gates 310a, 310b. In some embodiment, prior to introduction of the sample 350 into the sample lane 300, the first and second amplification valves 330a, 330b of the sample lane 300 can be in an open state, such that the TRS 345 is maintained in the wax loading channel 334, and therefore is not blocking passage of the sample 350 in the first channel 360 near the valves 330a, b. Thus, when the sample 350 is introduced into the microfluidic network, the sample 350 can bypass the closed amplification gate 310a (including the upstream 318 and downstream 320 sides of the amplification gate 310a) by following the route of the first channel 360 past the open first amplification valve 330a in the first channel 360. In this manner, the sample 350 can travel from the inlet 302, through the first channel 360, into the amplification chamber 362, thereby filling the amplification chamber 362 to capacity. In some embodiments the amplification chamber has a volumetric capacity of 8 µl. The volume of the sample 350 initially introduced into the sample 350 may be of a volume in excess of the volume of the amplification chamber 362. Any volume of the sample 350 in excess of the volume of the amplification chamber 362 can exit the amplification chamber 362 at a downstream side of the amplification chamber 362 and may enter the second channel 364.

The second channel 364 can extend from the amplification chamber 362 past the second amplification gate 310b into the second stage 208 of the microfluidic network of the sample lane 300. Because the second amplification gate 310b may be initially closed when the sample 350 is introduced into the sample lane 300, the sample 350 can be blocked by the second amplification gate 310b in the second channel 364 and diverted into the third channel 366. In the third channel 366, the sample can move past the second amplification valve 330b to the first vent 368. Any volume of the sample 350 in the third channel in excess of the volume of the third channel 366 can be drained and removed from the microfluidic network through the first vent 368.

In some embodiments, upon introduction of the sample 350 into the microfluidic network, the pipette tip 402 of the liquid dispenser 400 can be removed from the inlet 302 and the receiving tray 520 can be closed, thereby sliding the receiving tray 520 under the optical module 502. The force member (not shown) can then elevate the receiving tray 520 upward toward the bottom side 506 of the optical module 502 in order to press the cartridge 200 against the aperture plate 540 of the optical module 502. Pressing the cartridge 200 upward against the aperture plate 540 can cause the cartridge 200 to experience a physical pressure against the aperture plate 540. The physical pressure applied to the cartridge 200 by the aperture plate 540 can also cause the cartridge 200 to likewise apply a downward pressure against the heater substrate 600 in the receiving tray 520. The pressure applied to the cartridge 200 on its top side by the aperture plate 540 and on its bottom side by the heater substrate 600 can be applied in a substantially uniform manner throughout the cartridge 200 such that all portion of the cartridge 200 in the recessed bay 524 of the receiving tray 520 can experiencing the same degree of pressure.

Figure 10B:
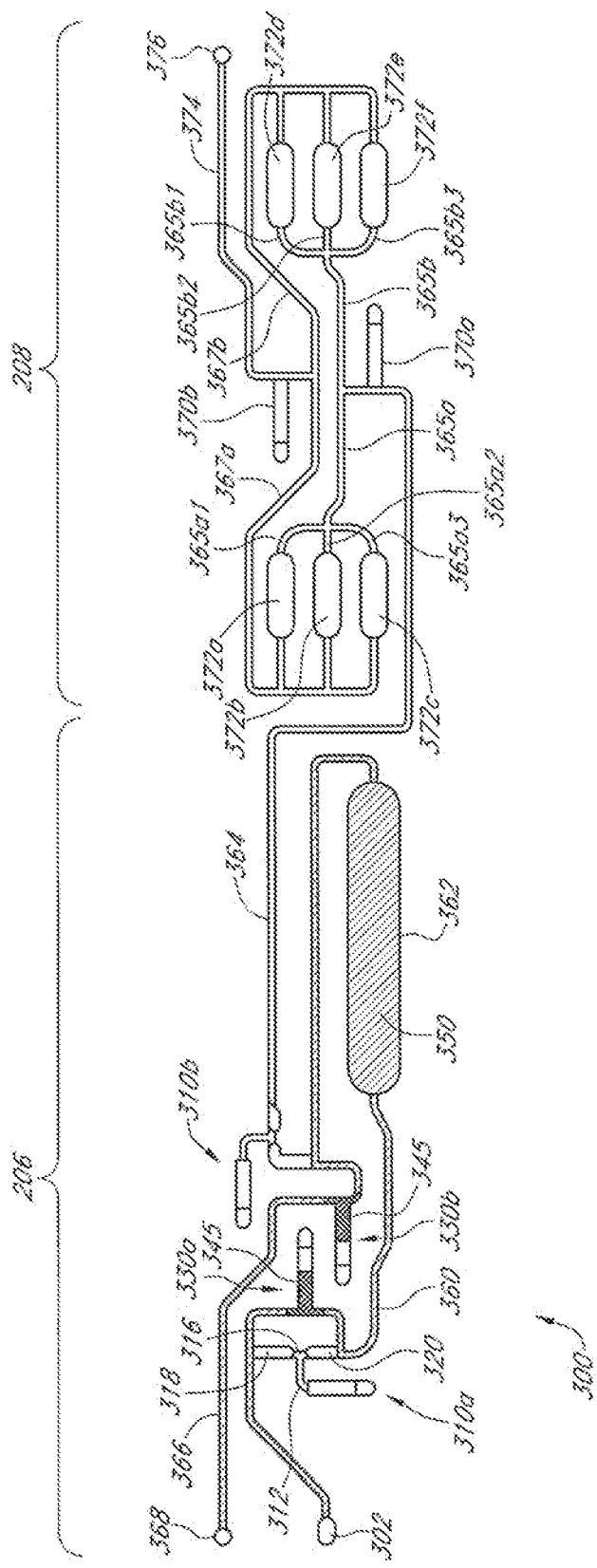

With the cartridge 200 positioned in the recessed bay 524 of the receiving tray 520, the various heaters of the heater substrate 600 can be in physical and/or thermal contact with the corresponding components (e.g., valves and gates) of the sample lanes 300 in cartridge 200. After the sample 350 is introduced into the sample lane 300 through the inlet 302 and the sample 350 is positioned in the first stage 206 of the sample lane 300, as shown in FIG. 10A, and physical pressure is applied between the cartridge 200 and the heater substrate 600, the first and second amplification valve heaters 630a, 630b can be turned on by sending the necessary electronic signals to the heaters. As illustrated in FIG. 10B, activating the first and second amplification valve heaters 630a, 630b, while bringing the activated heaters into physical and/or thermal contact with the first and second amplification valves 330a, 330b, can cause the TRS (e.g., wax) 345 in the first and second amplification valves 330a, 330b to melt and become mobile. As described in relation to FIGS. 4A-C, the mobile TRS 345 can then be expelled from the loading channel 334 by, for example, the expansion of the heated air in the valve loading port 332 of each of the first and second amplification valves 330a, b. The TRS 345 may then enter the first and second channels 360 and 364 at the valve junctions 336 of the respective valves 330a, b. The first and second amplification valve heaters 630a, b can then be turned off and the TRS 345 may cool, solidify, and become immobile in the valve junctions 336, thereby closing the first and second amplification valves 330a, 330b and sealing the first and second channels 360, 364 to prevent further movement of the sample 350 in either the upstream or downstream direction in the first stage 206 of the sample lane 300. Thus, at this stage of the sample processing, the first and second amplification valves 330a, b and the first and second amplification gates 310a, b are in a closed position, thereby isolating the sample 350 in the first stage 206 of the sample lane 300. A majority portion of the isolated sample 350 is contained in the amplification chamber 362. Thus, the sample 345 is isolated in the first stage 206 of the microfluidic network, being specifically isolated in the amplification chamber 362 in order to undergo thermocycling to amplify target polynucleotides present in the sample 350 by, for example, PCR.

Figure 10C:
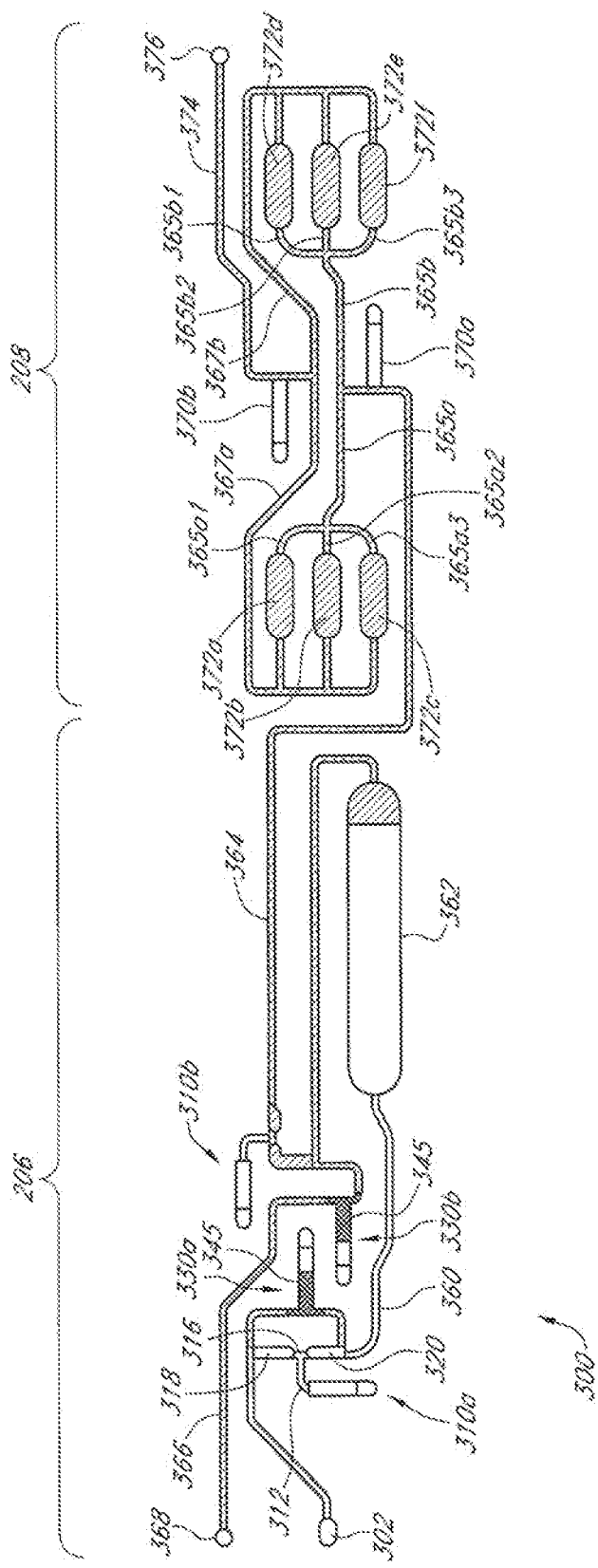

After completion of the amplification protocol in the amplification chamber 362, the amplified sample 350 can then be moved to the second stage 208 of the microfluidic network in the sample lane 300. Movement of the sample 350 from the first stage 206 into the detection chambers 372a-f of the second stage 208 is illustrated in FIG. 10C. To effectuate the movement of the sample 350 out of the first stage 206 and into the second stage 208, the initially-closed second amplification gate 310b can be opened and a motive force can be applied to the sample 350 to propel the sample 350 through the second channel 364 to the detection chambers 372a-f.

Prior to, and as a part of, advancing the sample 350 from the first stage 206 of the sample lane 300 to the second stage 208 of the sample lane 300, the receiving tray 520 can be opened in order to allow the fluid dispenser 400 to act on the cartridge 200. For each sample lane 300 being processed simultaneously in the cartridge 200, a pipette tip 402 of the fluid dispenser 400 can again be positioned in the inlet 302 of the sample lane 300. The actions of the fluid dispenser 400 on the cartridge 200 can be two-fold. The fluid dispenser 400 can be used to supply both physical pressure and air pressure to the cartridge 200.

When the receiving tray 520 is open and the cartridge 200 is no longer in a position under the aperture plate 540, the cartridge 200 is no longer receiving pressure from the aperture plate 540 to press it against the heater substrate 600. When receiving tray 520 is open and when the pipette tip 402 is inserted into the inlet 302 of a sample lane 300, the fluid dispenser can be activated to press the pipette tip 402 into the inlet 302 with additional pressure in order to press the cartridge 200 against the heater substrate 600. Thus, at this stage of the sample processing, the physical pressure between the cartridge 200 and the heater substrate 600 is provided by the physical pressure of the fluid dispenser 400 in pressing the pipette into the inlet 302.

When a pipette 402 is inserted into the inlet 302, the fluid dispenser 400 can introduce air or another gas into the microfluidic network of the sample lane 300 through the inlet 302, thus supplying an air pressure to the microfluidic network. As represented in FIG. 10C, the air pressure supplied to the microfluidic network can push on the portion of the sample 350 located in the first channel 360, which is isolated upstream of the first amplification gate 310a and first amplification valve 330a, both of which are in a closed position at this stage of the sample processing. Concurrent with dispensing the air or gas into the microfluidic network, the fluid dispenser 400 can be lowered to force the pipette tips 402 against the inlet 302 to supply the additional physical pressure on the cartridge 302, thereby keeping the first and second amplification gates 310a, b in physical contact with the respective amplification gate heaters 610a, b. The first and second amplification gate heaters 610a, b can then be activated in order to supply heat to the first and second amplification gates 310a, 310b. The heat from the amplification gate heaters 610a, 610b can melt the TRS 345 at the gate junctions 316 of the first and second amplification gates 310a, 310b in the first and second channels 360, 364, thus causing the TRS 345 to become mobile. The air pressure supplied to the sample 350 in the first channel 360 by the fluid dispenser 360 provides a force to the now-mobile TRS 345 at gate junction 316 of the first amplification gate 310a. The air pressure from the fluid dispenser 400 is sufficient to dislodge the mobile TRS 345 in the first amplification gate 310a in order to begin to move the TRS 345 downstream through the first channel 360. When the TRS 345 in the first amplification gate 310a is dislodged, the pressure against the sample 350 is then propagated downstream to the melted and mobile TRS 345 in the junction 316 of the second amplification gate 310b, thus also dislodging the TRS 345 in the second amplification gate 310b. With the TRS 345 removed from the junctions 316 of the first and second amplification gates 310a, b, the air pressure supplied by the fluid dispenser 400 is able to propel the majority of the sample 350 downstream into the second stage 208 of the sample lane 300. The TRS 345 dislodged from the first and second amplification gates 310a, 310b can move downstream along with the sample 350 as the sample 350 comes to occupy the detection chambers 372a-f. Any sample 350 volume in excess of the volume of the detection chambers 372a-f can continue travel beyond the detection chambers 372a-f into the subchannels 367a, 367b downstream of the detection chambers 372a-f. Additional excess sample 350 volume beyond the capacity of the detection chambers 372a-f can also travel downstream of the detection chambers 372a-f, through the subchannels 367a, 367b and past the second detection valve 370b, into the fourth channel 374. Additional excess sample 350 can be drained from the microfluidic network through the second vent 376 downstream of, and in fluid communication with, the fourth channel 374. Any TRS 345 in the detection chambers 372a-f downstream of the first and second amplification gates 310a, 310b does not interfere with any thermocycling or detection processes conducted in the detection chambers 372a-f.

As the sample 350 is moved into the detection chambers 372a-f as described above, the sample 350 comes into contact with the probes that were initially placed in the detection chambers 372a-f prior to use or during manufacture of the cartridge 200. Upon entry of the sample into the detection chambers 372a-f, the probes are dissolved into the sample 350 solution and bind to the polynucleotides in the sample 350 as described herein. Because an excess portion of the sample 350 will pass through the detection chambers 372a-f into the subchannels 367a, 367b and fourth channel 374, an excess amount of the probe can also initially be placed into the detection chambers 372a-f to compensate for the portion that may lost as it is absorbed by and passes downstream with the excess portion of the sample 350.

It is noted that the first and second amplification valves 330a, 330b can remain closed when the first and second amplification gates 310a, 310b are opened. This is possible because when the first and second amplification gate heaters 610a, 610b are activated to heat up the TRS 645 in the gate junctions 316, the first and second amplification valve heaters 630a, 630b are not activated, thus leaving the TRS in the valve junctions 336 in a solidified state. Furthermore, the closed first and second amplification valves 330a, b are sufficiently stable to not open again when the air pressure is applied by the fluid dispenser 400, in part because the valve junctions 336 are wider than the gate junctions 316 and thus can hold a greater quantity of TRS 345, the greater quantity of TRS 345 being more difficult to dislodge from the valve junction 336. Thus, closing the initially-open first and second amplification valves 330a, 330b is the mechanism by which the sample 350 becomes isolated in the amplification chamber 362. Conversely, opening the initially-closed first and second amplification gates 310a, 310b (along with supplying the air pressure) is the mechanism by which the sample 350 is moved from the first stage 206 of the sample lane 300 to the second stage 208 of the sample lane 300.

FIG. 10C shows that the sample 350 is located primarily in the second stage 208 of the sample lane 300 after the sample 350 has been displaced from the first stage 206 of the sample lane 300. At this point in the sample processing, the pipette tips 402 of the liquid dispenser 400 can be removed from the inlet 302 and the receiving tray 520 can once again be closed, thereby sliding the receiving tray 520 under the optical module 502 of the heater/optical unit 500. The force member is again used to apply upward pressure on the receiving tray 520, wherein the heater substrate 600 applies pressure against the cartridge 200 and the cartridge 200 likewise applies pressure against the aperture plate 540. When physical pressure is applied between the cartridge 200 and the heater substrate 600 and the aperture plate 540, the first and second detection valve heaters 670a, b can also be activated by sending the necessary electronic signals to the heaters.

Figure 10D:
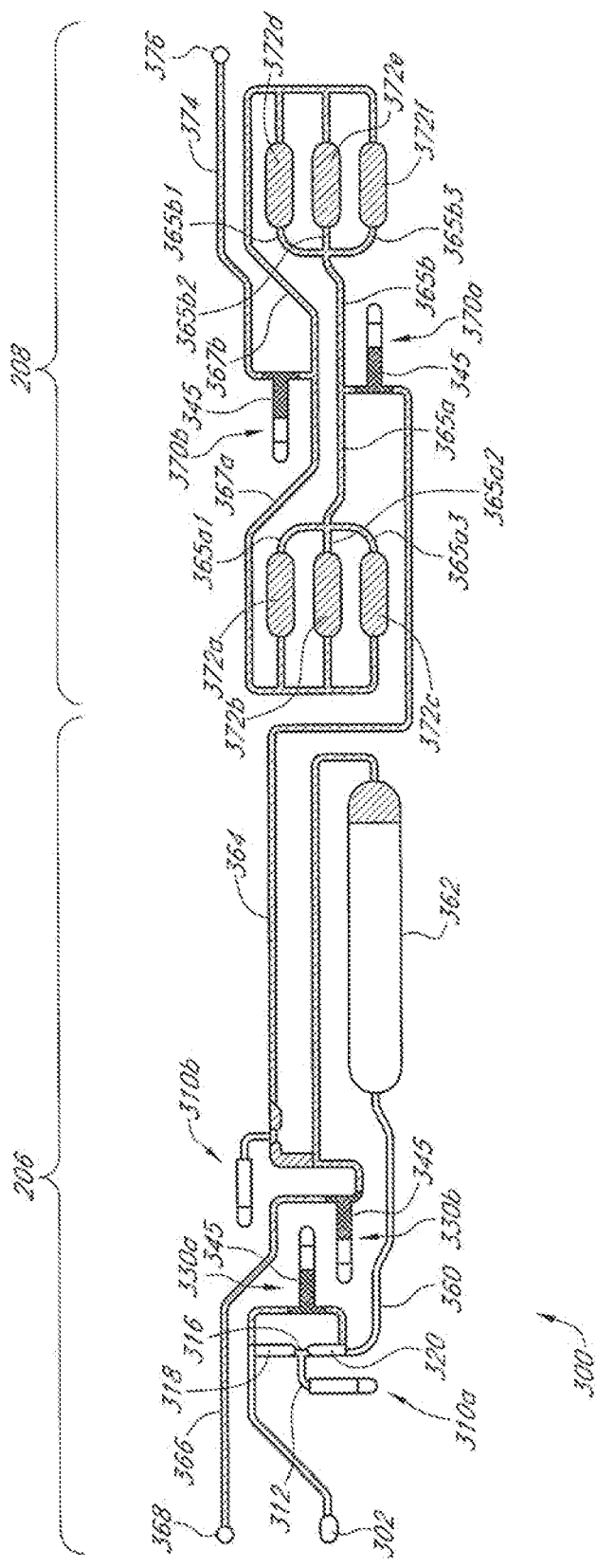

As illustrated in FIG. 10D, activating the first and second detection valve heaters 670a, 670b while bringing the heaters in physical and/or thermal contact with the first and second detection valves 370a, b, can cause the TRS (e.g., wax) 345 in the first and second detection valves 370a, b to melt and become mobile. The mobile TRS 345 can then be expelled from the loading channel 334 by, for example, the expansion of the heated air in the valve loading port 332 of each of the first and second detection valves 370a, b. The TRS 345 may then enter the second and fourth channels 364, 374 at the valve junctions 336 of the respective valves 370a, b. The first and second detection valve heaters 670a, 670b are then turned off and the TRS 345 may cool, solidify, and become immobile in the valve junctions 336, thereby closing the first and second detection valves 370a, 370b and sealing the second and fourth channels 364, 374 to prevent further movement of the sample 350 in either the upstream or downstream direction in the second stage 208 of the sample lane 300. Thus, the first and second detection valves 370a, 370b are now closed, isolating a majority portion of the sample 350 in the detection chambers 372a-f of the second stage 208 of the sample lane 300. The sample 350 is isolated in the detection chambers 372a-f in order to undergo a thermocycling procedure for analyte detection, as described elsewhere herein.

Following processing of the sample 350 in the amplification chamber 362 and deposition of the amplified samples in detection chambers 372a-f of the sample lane 300, the detector head 700 in the optical module 502 can conduct a detection procedure on the sample 350 in the detection chambers 372a-f to determine if specific analyte amplicons are present in the sample 350.

Referring again to FIG. 7B, the detector head 700 is housed in the optical unit 502 of the heater/optical module 500. As shown in FIG. 8, the detector head 700 is able to project light from the light sources 726a, 727a through the apertures 557 of the aperture plate 540 into the cartridge 200 and detect any fluorescence emitted from the detection chambers 372a-f in the cartridge 200 using the light detectors 726b, 727b.

FIGS. 11A-11D illustrate the movement of the detector head 700 in the optical unit 500 above the microfluidic cartridge 200 during the analyte detection procedure. In the embodiment shown in FIGS. 11A-11D, the detector head 700 is comprised of two rows and six columns of detector pairs, each column being comprised of two detector pairs. Labels 722a-733a represent the light sources of the detector pairs 722-733 in the detector head 700.

Figure 11A:
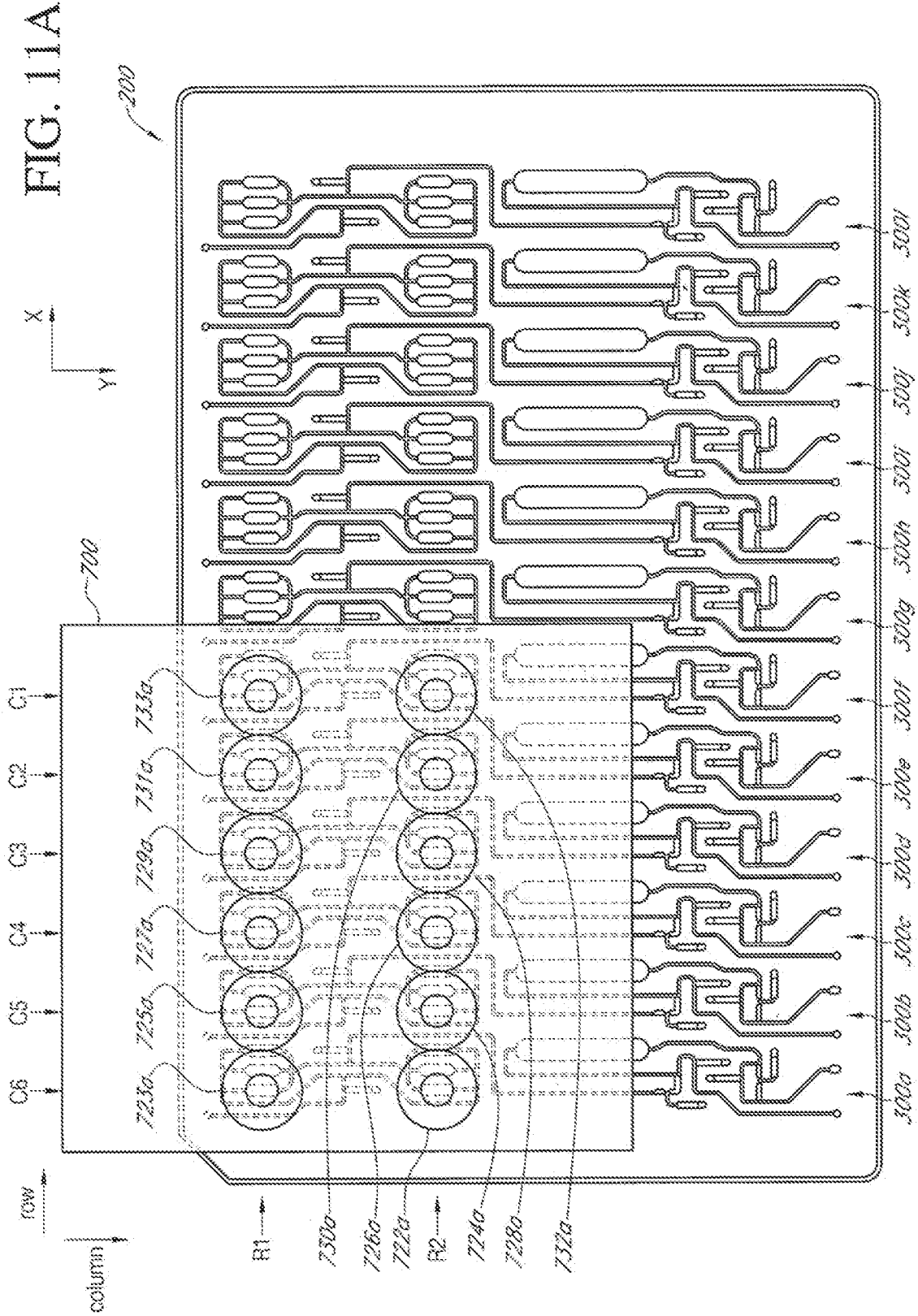

FIG. 11A shows the detector head 700 in a position above the cartridge 200, such that the detector head 700 has already advanced partially along the length (x-axis) of the cartridge 200. Previously to the positioning shown in FIG. 11A, following calibration of the detector head 700 using the normalizer plate 546, the detector head 700 may begin the detection procedure at a position such that a first column C1 of detector pairs 732, 733 is located over the first column of detection chambers 372a, 372d in the sample lane 300a. With the column C1 positioned over detection chambers 372a, 372d of sample lane 300a, the light sources 732a and 733a may emit light into the detection chambers 372a, 372d, respectively. The light detectors 732b and 733b will detect the light emitted from the detection chambers 372a, 372d to determine the presence or absence of one or more analyte polynucleotide amplicons in the sample 350. Following light emission and detection at the first column of detection chambers, detection chambers 372a, 372d, of sample lane 300a, the detector head 700 may advance lengthwise (along the x-axis) over the cartridge 200. The detector head 700 may advance to place the column C1 of detector pairs 732, 733 over the second column of detection chambers, detection chambers 372b, 372e, of sample lane 300a. The column C1 of detector pairs 732, 733 may then conduct analyte detection on the detection chambers 372b, 372e, and then advance to the third column of detection chambers, detection chambers 372c, 372f, of the sample lane 300a. After conducting analyte detection on all the detection chambers of sample lane 300a, the detector head 700 may be advanced to position the column C1 of detector pairs 732, 733 over the first column of detection chambers 372a, 372d in the sample lane 300b. When the column C1 of detector pairs 732, 733 is positioned over a column of detection chambers in the sample lane 300b, the column C2 of detector pairs 730, 731 can be positioned over the corresponding first column of detection chambers 372a, 372d in the sample lane 300a. The detector head 700 can continue advance lengthwise (along the x-axis) across the cartridge 200, thereby positioning each column C1-C6 of detector pairs over each column of detection chambers in each of the sample lanes 300a-300l of the cartridge 200. The wavelength of light produced and detected by each detector pair 722-733 may be different, thereby allowing for detection of a plurality of different polynucleotide markers using different fluorophore probes associated with the different markers.

Figure 11B:
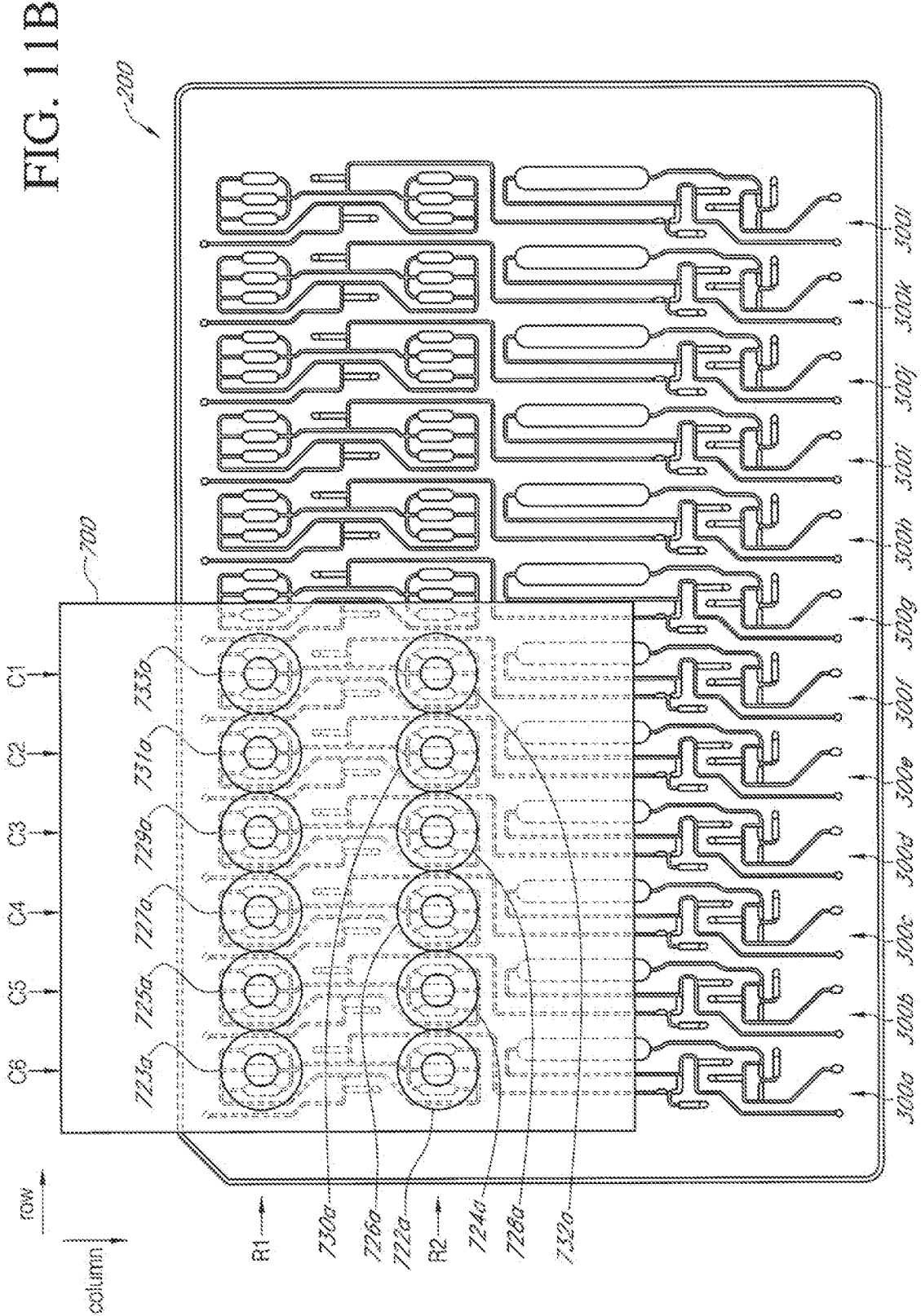
Figure 11C:
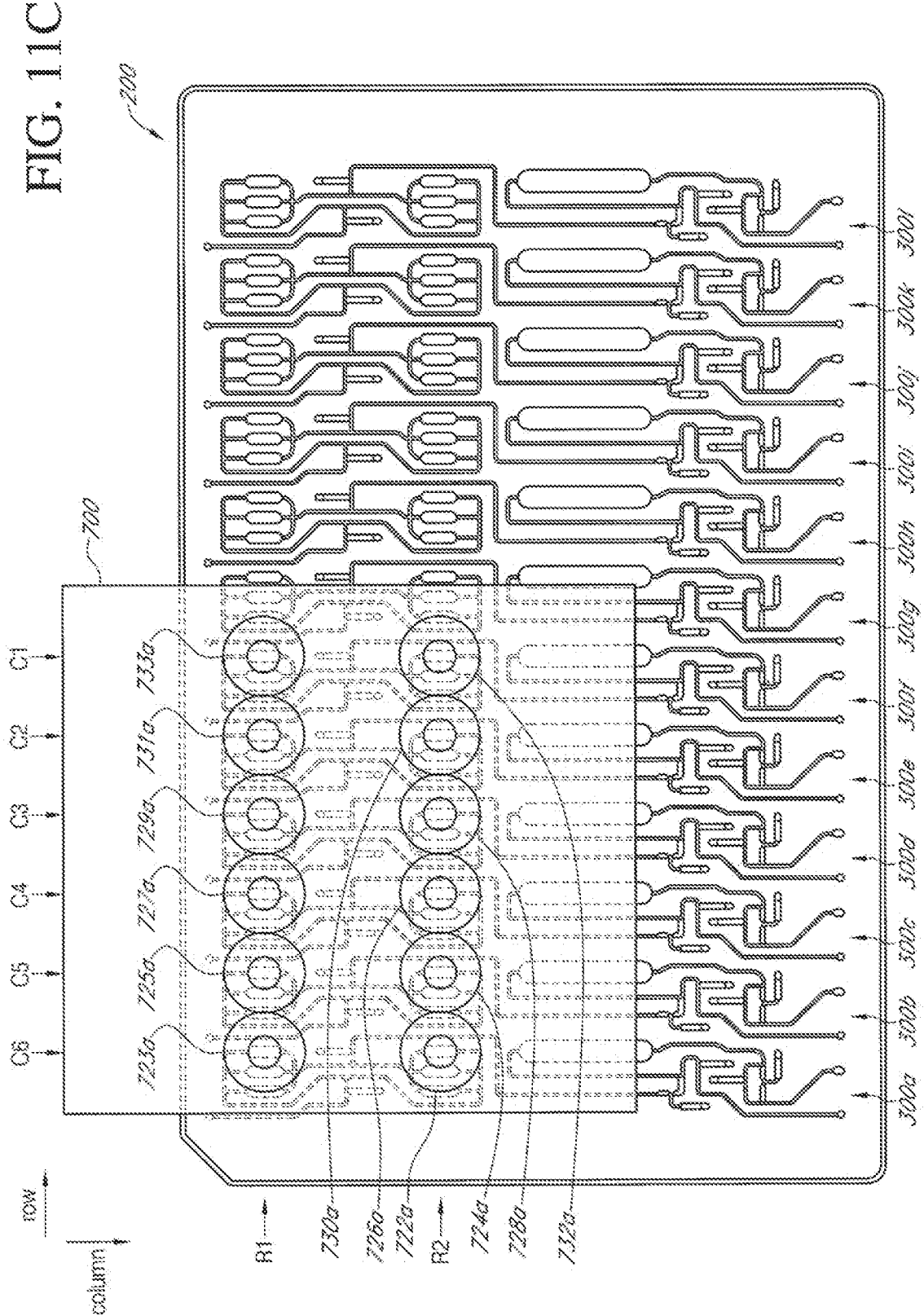

FIG. 11A shows the detector head 700 positioned over the cartridge 200 so that the column C1 of detector pairs is positioned over the first column of detection chambers 372a, 372d of sample lane 300f. Likewise, each of the other columns C2-C6 is positioned over the first column of detection chambers 372a, 372d in each of the sample lanes 300f-300a, respectively. FIG. 11B shows the advancement of the detector head 700 across the cartridge 200 so that each of the columns C1-C6 of detector pairs is positioned over the second column of detection chambers 372b, 372e in each of the sample lanes 300f-300a, respectively. FIG. 11C shows the advancement of the detector head 700 across the cartridge 200 so that each of the columns C1-C6 of detector pairs is positioned over the third column of detection chambers 372c, 372f in each of the sample lanes 300f-300a, respectively.

FIG. 11D shows the continued advancement of the detector head 700 across the cartridge 200 so that each of the columns C1-C6 of detector pairs is again positioned over the first column of the detection chambers in the sample lanes. FIG. 11D shows the detector head 700 positioned over the cartridge 200 so that each of the columns C1-C6 of detector pairs is positioned over the first column of detection chambers 372a, 372d in each of the sample lanes 300b-300g, respectively. With the detector head 700 positioned as shown in FIG. 11D, the detector head 700 has completed the detection procedure in the six detection chambers 372a-f of sample lane 300a. At this point, each detection chamber 372a-f of sample lane 300a has been optically scanned by six detector pairs. More specifically, detection chambers 372d-f in the top group of detection chambers in the sample lane 300a has been optically scanned by detector pairs 733, 731, 729, 727, 725, and 723 of row R1 of the detector head 700; detection chambers 372a-c in the bottom group of detection chambers in the sample lane 300a has been optically scanned by detector pairs 732, 730, 728, 726, 724, and 722 of row R2 of the detector head 700. The detector head 700 may continue to advance across the cartridge 200 until each of the detection chambers 372a-f in each of the sample lanes 300a-300l has been optically scanned by the detector head 700.

Because of the arrangement of the detection chambers 372a-f into rows and columns, each sample 350 in a sample lane 300 may undergo multiplexed amplicon detection. For example, each detection chamber 372a-f can be optically scanned by six different detector pairs, the detection chambers 372a-c being scanned by detector pairs in row R1 and the detection chambers 372d-f being scanned by detector pairs in row R2 of the detector head 700. In certain embodiments, the detector pairs in each column can be configured to emit and detect light of the same wavelength (color) as each other, but wherein the wavelength is different than the light emitted and detected by the detector pairs in the other columns. Each column of detector pairs may emit and detect a unique wavelength of light, and as such the detector 700 may emit and detect light of six different wavelengths. Accordingly, each detection chamber 372a-f in each of the sample lanes 300a-l may be optically scanned by six different wavelengths of light. Alternatively, the detector pairs individually in each column C1-C6 may emit and detect a unique wavelength of light. Thus, the detector may emit and detect light of 12 different wavelengths, a different length emitted and detected by each detector pair 722-733.

Each of the detection chambers 372a-f in each of the sample lanes 300a-l may be pre-loaded with fluorescence probes, each of which can be associated with a certain wavelength (color); each probe also specifically binds to (e.g., under stringent conditions), a particular sequence to be detected (e.g., a target amplicon, a positive control sequence, or the like). When the sample 350 is moved into the detection chambers 372a-f (as shown in FIG. 10C), one or more of the probes present in the detection chamber 372*a-f* may bind with the analyte associated with the probe, if the analyte is indeed present in the sample 350. Each of the detection chambers 372*a-f* may be pre-loaded with six different probes. Thus, the detection chambers 372*a-f* of each sample lane 300 may contain a total of 36 different probes. Furthermore, each probe may undergo three melts in the detection chamber. Accordingly, each sample lane 300 can perform detection on up to 108 analytes.

The detection data obtained from the detector head 700 can be recorded and associated with the samples 350 in the sample lanes 300*a-l*. Following completion of the detection procedure, the sample 350 may remain isolated in the detection chambers 372*a-f* in the second stage 208 of the sample lanes 300*a-l*. After the detection procedure is complete, the receiving tray 520 may be opened again and the cartridge 200 may be removed, in a manual or automated fashion, from the recessed bay 524 of the receiving tray 520. The cartridge 200 may be discarded.

The above description discloses several methods and systems of the embodiments disclosed herein. The embodiments disclosed herein are susceptible to modifications in the methods and materials, as well as alterations in the fabrication methods and equipment. Such modifications will become apparent to those skilled in the art from a consideration of this disclosure or practice of the invention disclosed herein. Consequently, it is not intended that the embodiments disclosed herein be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A microfluidic cartridge comprising:
  a plurality of sample lanes, each lane comprising a microfluidic network having:
    an inlet;
    a single amplification chamber, wherein the single amplification chamber is configured to be heated in which polynucleotides in a sample are amplified within the single amplification chamber;
    a first amplification valve upstream of the single amplification chamber;
    a second amplification valve downstream of the single amplification chamber;
    a first channel fluidically transmitting the sample from the inlet, via the first amplification valve, to the single amplification chamber;
    a plurality of detection chambers downstream of the single amplification chamber;
    a first detection valve downstream of the single amplification chamber and upstream of the plurality of detection chambers, wherein the first detection valve is spatially separated from the second amplification valve;
    a second detection valve downstream of the plurality of detection chambers, wherein the only entrance to the plurality of detection chambers is through the first detection valve and the only exit from the plurality of detection chambers is through the second detection valve; and
    a second channel fluidically transmitting the sample from the single amplification chamber, via the first detection valve, to two or more subchannels, each subchannel connecting to one of the plurality of detection chambers, wherein the two or more subchannels are configured to allow filling of two or more detection chambers of the plurality of detection chambers with the sample from the single amplification chamber, and wherein the second amplification valve is closed when the sample is transmitted from the single amplification chamber to the plurality of detection chambers downstream of the single amplification chamber.

2. The microfluidic cartridge of claim 1, further comprising a third channel in each of the microfluidic networks, the third channel leading from the single amplification chamber, via the second amplification valve, to a first vent.

3. The microfluidic cartridge of claim 2, further comprising a fourth channel in each of the microfluidic networks, the fourth channel leading from the plurality of detection chambers, via the second detection valve to a second vent.

4. The microfluidic cartridge of claim 1, wherein the amplification valves comprise a temperature responsive substance that melts upon heating to seal one of at least the first and second channels in fluid communication with the single amplification chamber.

5. The microfluidic cartridge of claim 1, wherein the detection valves comprise a temperature responsive substance that melts upon heating to seal the second channel that communicates with the plurality of detection chambers.

6. The microfluidic cartridge of claim 1, wherein the single amplification chamber has a volume of 5-10 µl.

7. The microfluidic cartridge of claim 1, wherein the plurality of detection chambers each has a volume of approximately 1 µl.

8. The microfluidic cartridge of claim 1, further comprising one or more fluorescence detection windows.

9. A microfluidic cartridge comprising:
  a plurality of sample lanes, each lane comprised of a microfluidic network having a first and a second stage connected by a microfluidic channel,
  the first stage comprising:
    an inlet;
    a single amplification chamber in fluid communication with the inlet, wherein the single amplification chamber is configured to be heated to amplify polynucleotides in a sample;
    a first amplification valve upstream of the single amplification chamber;
    a second amplification valve downstream of the single amplification chamber;
  the second stage downstream to the first stage comprising:
    a plurality of detection chambers; and
    a first detection valve downstream of the single amplification chamber and upstream of the plurality of detection chambers, wherein the first detection valve is spatially separated from the second amplification valve;
    a second detection valve downstream of the plurality of detection chambers, the first detection valve and the second detection valve configured to isolate the sample within the plurality of detection chambers, the sample fluidically transmitted from the single amplification chamber to the plurality of detection chambers, wherein the second amplification valve is closed when the sample is fluidically transmitted from the single amplification chamber to the plurality of detection chambers downstream of the single amplification chamber, wherein the plurality of detection chambers are disposed between the first detection valve and the second detection valve.

10. The cartridge of claim 9, further comprising a first amplification gate upstream of the single amplification chamber and a second amplification gate downstream of the single amplification chamber, wherein the first and second amplification gates are in an initially closed position prior to introduction of a sample.

11. The cartridge of claim 9, wherein the first and second amplification valves are in an initially open position prior to introduction of a sample.

12. The cartridge of claim 9, further comprising a first vent and a second vent.

13. The cartridge of claim 9, wherein the first and second stages of each microfluidic network are in the same horizontal plane.

14. The cartridge of claim 9, wherein a liquidic volume of the first stage is greater than a liquidic volume of the second stage.

15. A multiplexed microfluidic cartridge comprising:
a plurality of sample lanes, each lane comprised of a microfluidic network having:
one isolatable amplification chamber in which polynucleotides in a sample are amplified, wherein the one isolatable amplification chamber is configured to be heated to amplify polynucleotides in the sample; and
a plurality of isolatable detection chambers downstream of the one isolatable amplification chamber, the plurality of detection chambers isolated by a first detection valve downstream of the one isolatable amplification chamber and upstream of the plurality of detection chambers and a second detection valve downstream of the plurality of detection chambers;
each detection chamber in fluid communication with the one isolatable amplification chamber such that each detection chamber receives a divisible portion of the sample from the one isolatable amplification chamber;
wherein the one isolatable amplification chamber and the plurality of detection chambers are connected via a microfluidic channel, the microfluidic channel configured to allow filling of two or more detection chambers of the plurality of detection chambers with a motive force applied to the sample to propel the sample to the two or more detection chambers, and wherein a valve isolating the one isolatable amplification chamber from the microfluidic channel is closed when the sample is propelled to the two or more detection chambers downstream of the one isolatable amplification chamber.

16. The multiplexed microfluidic cartridge of claim 15, wherein each microfluidic network comprises one isolatable amplification chamber and six detection chambers.

17. The multiplexed microfluidic cartridge of claim 15, wherein each of the plurality of detection chambers in the microfluidic network is of equal volume.

18. The multiplexed microfluidic cartridge of claim 17, wherein each detection chamber has a volume of approximately 1 μl.

19. The multiplexed microfluidic cartridge of claim 15, wherein the one isolatable amplification chamber has a volume of approximately 5-10 μl.

20. The microfluidic cartridge of claim 15, wherein a collective volume of the plurality of detection chambers is less than a volume of the one isolatable amplification chamber.

21. The microfluidic cartridge of claim 1, wherein each sample lane forms a column in the microfluidic cartridge, and the plurality of detection chambers are arranged in at least a first bank forming a first row within the column and a second bank forming a second row within the column.

22. The microfluidic cartridge of claim 9, wherein each sample lane forms a column in the microfluidic cartridge, and the plurality of detection chambers are arranged in at least a first bank forming a first row within the column and a second bank forming a second row within the column.

23. The multiplexed microfluidic cartridge of claim 15, wherein each sample lane forms a column in the microfluidic cartridge, and the plurality of detection chambers are arranged in at least a first bank forming a first row within the column and a second bank forming a second row within the column.

* * * * *